(12) United States Patent
Hallahan et al.

(10) Patent No.: US 9,340,581 B2
(45) Date of Patent: May 17, 2016

(54) LIGANDS TO RADIATION-INDUCED MOLECULES

(71) Applicants: Dennis E. Hallahan, St. Louis, MO (US); Shimian Qu, Brentwood, TN (US); Zhaozhong Han, Franklin, TN (US)

(72) Inventors: Dennis E. Hallahan, St. Louis, MO (US); Shimian Qu, Brentwood, TN (US); Zhaozhong Han, Franklin, TN (US)

(73) Assignee: WASHINGTON UNIVERSITY, St. Louis, MO (US)

( * ) Notice: Subject to any disclaimer, the term of this patent is extended or adjusted under 35 U.S.C. 154(b) by 146 days.

(21) Appl. No.: 14/308,419

(22) Filed: Jun. 18, 2014

(65) Prior Publication Data

US 2014/0369929 A1 Dec. 18, 2014

Related U.S. Application Data

(60) Continuation of application No. 13/766,310, filed on Feb. 13, 2013, now Pat. No. 8,765,097, which is a division of application No. 13/018,747, filed on Feb. 1, 2011, now Pat. No. 8,388,932, which is a division of application No. 11/183,325, filed on Jul. 15, 2005, now Pat. No. 7,906,102, which is a continuation-in-part of application No. 10/259,087, filed on Sep. 27, 2002, now Pat. No. 7,402,392.

(60) Provisional application No. 60/328,123, filed on Oct. 3, 2001.

(51) Int. Cl.

| A61K 51/00 | (2006.01) |
|---|---|
| A61K 36/14 | (2006.01) |
| C07K 7/08 | (2006.01) |
| A61K 41/00 | (2006.01) |
| A61K 51/08 | (2006.01) |
| A61K 51/12 | (2006.01) |
| C07K 16/18 | (2006.01) |
| C07K 16/44 | (2006.01) |
| A61K 47/42 | (2006.01) |
| A61K 49/00 | (2006.01) |
| A61N 5/10 | (2006.01) |
| C07K 2/00 | (2006.01) |
| A61K 38/08 | (2006.01) |
| A61K 38/03 | (2006.01) |
| A61K 49/08 | (2006.01) |
| A61K 49/14 | (2006.01) |
| C07K 7/06 | (2006.01) |

(52) U.S. Cl.
CPC . *C07K 7/08* (2013.01); *A61K 38/08* (2013.01); *A61K 41/00* (2013.01); *A61K 41/0038* (2013.01); *A61K 47/42* (2013.01); *A61K 49/0002* (2013.01); *A61K 51/08* (2013.01); *A61K 51/082* (2013.01); *A61K 51/1255* (2013.01); *A61N 5/10* (2013.01); *C07K 2/00* (2013.01); *C07K 16/18* (2013.01); *C07K 16/44* (2013.01); *A61K 38/03* (2013.01); *A61K 49/08* (2013.01); *A61K 49/14* (2013.01); *C07K 7/06* (2013.01); *C07K 2317/622* (2013.01)

(58) Field of Classification Search
CPC ... A61K 41/00; A61K 41/0038; A61K 51/00; A61K 51/08; A61K 51/1255; A61K 51/082; A61K 47/42; A61K 49/0002; A61K 38/00; A61K 38/03; A61K 49/00; A61K 49/08; A61K 49/14; C07K 7/06; C07K 2/00; C07K 2317/622; C07K 16/44; C07K 7/08; A61N 5/10
USPC .......... 424/1.11, 1.65, 1.69, 9.1, 9.3, 9.4, 9.5, 424/9.6; 514/1, 1.1
See application file for complete search history.

(56) References Cited

U.S. PATENT DOCUMENTS

| 4,281,061 A | 7/1981 | Zuk |
|---|---|---|
| 4,515,165 A | 5/1985 | Carroll |
| 4,619,823 A | 10/1986 | Yokoyama et al. |
| 4,670,386 A | 6/1987 | Sugaar |
| 5,093,104 A | 3/1992 | Kaminsky |
| 5,277,892 A | 1/1994 | Rhodes |
| 5,292,524 A | 3/1994 | Male et al. |
| 5,328,840 A | 7/1994 | Coller |
| 5,334,369 A | 8/1994 | Haluska et al. |
| 5,382,680 A | 1/1995 | Abraham et al. |

(Continued)

FOREIGN PATENT DOCUMENTS

| DE | 2621311 A1 | 11/1976 |
|---|---|---|
| EP | 0229718 B1 | 4/1991 |

(Continued)

OTHER PUBLICATIONS

Wong, Y. et al., "Frequent loss of heterozygosity of chromosome 3 short arm detected by PCR-based microsatellite polymorphisms in cervical squamous cell carcinoma," Cancer Letters, 1997, pp. 161-164, vol. 115.

(Continued)

*Primary Examiner* — D L Jones
(74) *Attorney, Agent, or Firm* — Polsinelli PC

(57) ABSTRACT

A method for identifying a molecule that binds an irradiated tumor in a subject and molecules identified thereby. In some embodiments, the method includes the steps of (a) exposing a tumor to ionizing radiation; (b) administering to a subject a library of diverse molecules; and (c) isolating from the tumor one or more molecules of the library of diverse molecules, whereby a molecule that binds an irradiated tumor is identified. Also provided are targeting ligands that bind an irradiated tumor and therapeutic and diagnostic methods that employ the disclosed targeting ligands.

13 Claims, No Drawings

(56) References Cited

U.S. PATENT DOCUMENTS

| | | | |
|---|---|---|---|
| 5,516,881 A | 5/1996 | Lee et al. | |
| 5,614,535 A | 3/1997 | Juraszyk | |
| 5,645,815 A | 7/1997 | Dean | |
| 5,693,627 A | 12/1997 | Schieven | |
| 5,759,542 A | 6/1998 | Gurewich | |
| 5,776,427 A | 7/1998 | Thorpe | |
| 5,830,856 A | 11/1998 | Dean | |
| 5,855,866 A | 1/1999 | Thorpe | |
| 5,863,538 A | 1/1999 | Thorpe | |
| 5,889,169 A | 3/1999 | Beach | |
| 5,962,424 A | 10/1999 | Hallahan et al. | |
| 5,965,132 A | 10/1999 | Thorpe | |
| 5,977,313 A | 11/1999 | Heath | |
| 6,004,554 A | 12/1999 | Thorpe | |
| 6,033,847 A | 3/2000 | Sherr | |
| 6,051,230 A | 4/2000 | Thorpe | |
| 6,068,829 A | 5/2000 | Ruoslahti | |
| 6,156,736 A | 12/2000 | Weichselbaum | |
| 6,159,443 A | 12/2000 | Hallahan | |
| 6,174,687 B1 | 1/2001 | Rajotte | |
| 6,232,287 B1 | 5/2001 | Ruoslahti et al. | |
| 6,261,535 B1 | 7/2001 | Thorpe | |
| 6,277,974 B1 | 8/2001 | Lo et al. | |
| 6,316,208 B1 | 11/2001 | Roberts | |
| 6,383,470 B1 | 5/2002 | Fritzsch | |
| 6,403,383 B1 | 6/2002 | Casterlin | |
| 6,576,239 B1 | 6/2003 | Ruoslahti | |
| 6,605,712 B1 | 8/2003 | Weichselbaum | |
| 6,630,570 B1 | 10/2003 | Licha et al. | |
| 6,673,545 B2 | 1/2004 | Faris et al. | |
| 7,018,615 B2 | 3/2006 | Ruoslahti | |
| 7,018,618 B2 | 3/2006 | Lewis et al. | |
| 7,049,140 B1 * | 5/2006 | Hallahan | A61K 41/00 424/450 |
| 7,056,506 B2 | 6/2006 | Varner | |
| 7,122,361 B2 | 10/2006 | Liu et al. | |
| 7,138,238 B2 | 11/2006 | Vodyanoy | |
| 7,230,083 B2 | 6/2007 | Jonak et al. | |
| 7,230,088 B2 | 6/2007 | Rajagopalan et al. | |
| 7,306,925 B2 * | 12/2007 | Hallahan | A61B 6/508 435/235.1 |
| 7,402,392 B2 * | 7/2008 | Hallahan | A61K 41/0038 435/235.1 |
| 7,875,454 B2 | 1/2011 | Hallahan | |
| 7,906,102 B2 * | 3/2011 | Hallahan | A61K 41/00 424/1.11 |
| 7,968,675 B2 * | 6/2011 | Hallahan | A61K 41/0038 530/300 |
| 8,012,945 B2 | 9/2011 | Hallahan et al. | |
| 8,101,157 B2 * | 1/2012 | Hallahan | A61K 41/0038 424/1.11 |
| 8,388,932 B2 * | 3/2013 | Hallahan | A61K 41/00 424/1.11 |
| 8,617,521 B2 | 12/2013 | Hallahan et al. | |
| 8,765,097 B2 * | 7/2014 | Hallahan | A61K 41/00 424/1.11 |
| 2002/0086288 A1 | 7/2002 | Bird et al. | |
| 2002/0164663 A1 | 11/2002 | Fuqua et al. | |
| 2003/0027159 A1 | 2/2003 | Ward et al. | |
| 2003/0083261 A1 | 5/2003 | Yu et al. | |
| 2003/0130190 A1 | 7/2003 | Hallahan et al. | |
| 2003/0157025 A1 | 8/2003 | Unger et al. | |
| 2003/0157482 A1 | 8/2003 | Keesee | |
| 2004/0191249 A1 | 9/2004 | Hallahan et al. | |
| 2006/0046271 A1 | 3/2006 | Hallahan | |
| 2006/0104898 A1 | 5/2006 | Hallahan | |
| 2006/0188442 A1 | 8/2006 | Hallahan | |
| 2007/0065361 A1 | 3/2007 | Hallahan | |
| 2007/0081993 A1 | 4/2007 | Kufer et al. | |
| 2008/0118978 A1 | 5/2008 | Sato et al. | |
| 2008/0187488 A1 | 8/2008 | Hallahan et al. | |
| 2008/0206130 A1 | 8/2008 | Hallahan et al. | |
| 2008/0305111 A1 | 12/2008 | Evans et al. | |
| 2010/0039023 A1 | 2/2010 | Rogojevic et al. | |
| 2010/0041074 A1 | 2/2010 | Kimura | |
| 2010/0111852 A1 | 5/2010 | Yoshida | |
| 2010/0111959 A1 | 5/2010 | Swanson et al. | |
| 2010/0135905 A1 | 6/2010 | Hallahan et al. | |
| 2011/0213293 A1 | 9/2011 | Hallahan et al. | |
| 2012/0041303 A1 | 2/2012 | Hallahan et al. | |
| 2013/0251628 A1 | 9/2013 | Hallahan et al. | |
| 2014/0088408 A1 | 3/2014 | Hallahan et al. | |

FOREIGN PATENT DOCUMENTS

| | | |
|---|---|---|
| EP | 0723156 A2 | 7/1996 |
| EP | 0723156 A3 | 4/1998 |
| EP | 1217377 B1 | 6/2002 |
| WO | 1986005693 A1 | 10/1986 |
| WO | 1992020796 A2 | 11/1992 |
| WO | 1993006835 A1 | 4/1993 |
| WO | 1993014791 A2 | 8/1993 |
| WO | 1993020229 A1 | 10/1993 |
| WO | 1995033496 A1 | 12/1995 |
| WO | 1995034315 A1 | 12/1995 |
| WO | 1996012956 A1 | 5/1996 |
| WO | 1996025947 A2 | 8/1996 |
| WO | 1998010795 A3 | 3/1998 |
| WO | 1999004238 A2 | 1/1999 |
| WO | 2000066182 A1 | 11/2000 |
| WO | 2001009611 A2 | 2/2001 |
| WO | 2001009611 A3 | 7/2001 |
| WO | 2003028640 A2 | 4/2003 |
| WO | 2005042780 A1 | 5/2005 |
| WO | 2006028993 A2 | 3/2006 |
| WO | 2007011680 A2 | 1/2007 |

OTHER PUBLICATIONS

Wong, Y. et al., "p16INK4 and p15INK4B Alterations in Primary Gynecologic Malignancy," Gynecologic Onco., 1997, pp. 319-324, vol. 65, Article No. GO974669.

Xu, X. et al., "Cell cycle proteins PP5 associated with Rad9 and uses in screening for a bioactive agent," Database HCAPLUS on STN, 2001, Abstract WO01/64913, Accession No. 2001:661624, Registry No. 263887-03-02 for human gene rad9 for SEQ ID No. 8, 1 page.

Yokota, T. et al., "Rapid Tumor Penetration of a Single-Chain Fv and Comparison with Other Immunoglobulin Forms," Can. Res., Jun. 15, 1992, pp. 3402-3408, vol. 52.

Notice of Allowance from related U.S. Appl. No. 14/092,412 dated Aug. 26, 2014, 5 pages.

Notice of Allowance from related U.S. Appl. No. 14/092,412, dated Jul. 25, 2014, 6 pages.

Office Action from related U.S. Appl. No. 14/092,412, dated Jan. 14, 2014, 6 pages.

Office Action (Advisory) from related U.S. Appl. No. 11/592,451, dated Feb. 28, 2011, 3 pages.

Office Action from related European Patent Application No. 00935839.1, dated Feb. 28, 2005, 3 pages.

Office Action from related European Patent Application No. 00935839.1, dated Aug. 13, 2008, 4 pages.

Office Action from related U.S. Appl. No. 09/914,605, dated Apr. 18, 2005, 7 pages.

Office Action from related U.S. Appl. No. 09/914,605, dated Sep. 8, 2004, 7 pages.

Office Action from related U.S. Appl. No. 10/689,006, dated Jan. 19, 2007, 6 pages.

Office Action from related U.S. Appl. No. 11/183,325, dated Jun. 8, 2010, 11 pages.

Office Action from related U.S. Appl. No. 11/413,783, dated Jan. 7, 2010, 9 pages.

Office Action from related U.S. Appl. No. 11/413,783, dated Jan. 28, 2008, 11 pages.

Office Action from related U.S. Appl. No. 11/592,451 dated Mar. 24, 2011, 18 pages.

Office Action from related U.S. Appl. No. 11/592,451, dated May 13, 2010, 11 pages.

Office Action from related U.S. Appl. No. 11/592,451, dated Nov. 18, 2010, 17 pages.

(56) References Cited

OTHER PUBLICATIONS

Office Action from related U.S. Appl. No. 11/953,780, dated Oct. 22, 2010, 6 pages.
Office Action from related U.S. Appl. No. 11/953,780, dated Feb. 19, 2010, 6 pages.
Office Action from related U.S. Appl. No. 12/111,693, dated Aug. 5, 2010, 27 pages.
Office Action from related U.S. Appl. No. 13/195,570, dated Nov. 15, 2012, 5 pages.
Office Action from related U.S. Appl. No. 13/195,570, dated Aug. 1, 2012, 8 pages.
Office Action from related U.S. Appl. No. 13/195,570, dated May 1, 2013, 6 pages.
Office Action from related U.S. Appl. No. 13/766,310, dated Nov. 12, 2013, 8 pages.
Onions, J. et al., "p73 is over-expressed in vulval cancer principally as the A2 isoform," British J. Cancer, 2001, pp. 1551-1556, vol. 85, No. 10.
Pan, X-M. et al., "What is the Minimum Number of Residues to Determine the Secondary Structural State?," J. Protein Chem., 1999, pp. 579-584, vol. 18, No. 5.
Pasqualini, R. et al., "Organ targeting in vivo using phage display peptide libraries," Nature, Mar. 28, 1996, pp. 364-366, vol. 380.
Pastan, I., "Targeted therapy of cancer with recombinant immunotoxins," Biochimica et Biophysica Acta, 1997, pp. C1-C6, vol. 1333.
Pinsky, D. et al., "Hypoxia-induced Exocytosis of Endothelial Cell Weibel-Palade Bodies. A Mechanism for Rapid Neutrophil Recruitment after Cardiac Preservation," J. Clin. Invest, Jan. 1996, pp. 493-500, vol. 97, No. 2.
Plath, T. et al., "A Novel Function for the Tumor Suppressor p16INK4a: Induction of Anoikis via Upregulation of the alpha5beta1 Fibronectin Receptor," J. Cell Bio., Sep. 18, 2000, pp. 1467-1477, vol. 150, No. 6.
Qualtiere, L. et al., "Effects of Ionic and Nonionic Detergents on Antigen-Antibody Reactions," J. Immunol., Nov. 1977, pp. 1645-1651, vol. 119.
Rajotte, D. et al., "Membrane Dipeptidase is he Receptor for a Lung-targeting Peptide Identified by in vivo Phage Display," J. Bio. Chem., Apr. 23, 1999, pp. 11593-11598, vol. 274, No. 17.
Rosenberg, E. et al., "Destruction of Human Lymphoid Tissue-Culture Cell Lines by Human Peripheral Lymphocytes in 51Cr-Release Cellular Cytotoxicity Assays," J. Nat. Cancer Inst, Feb. 1974, pp. 345-352, vol. 52, No. 2.
Ruoslahti, E., "RGD and Other Recognition Sequences for Integrins," Annu. Rev. Cell Dev. Biol., 1996, pp. 697-715, vol. 12.
Ryder, K. et al., "An Enzyme Immunoassay Procedure for Cancer Antigen 125 Evaluated," Clin. Chem., 1988, pp. 2513-2516, vol. 34, No. 12.
Sakamoto, N. et al., "Inhibition of Angiogenesis and Tumor Growth by a Synthetic Laminin Peptide, CDPGYIGSR-NH2," Cancer Res., Feb. 1, 1991, pp. 903-906, vol. 51.
Sano, T. et al., "Immunohistochemical overexpression of p16 protein associated with intact retinoblastoma protein expression in cervical cancer and cervical intraepithelial neoplasia," Pathology Int., 1998, pp. 580-585, vol. 48.
Sano, T. et al., "Overexpression of p16 and p14ARF is associated with human papillomavirus infection in cervical squamous cell carcinoma and dysplasia," Pathology Int., 2002, pp. 375-383, vol. 52.
Sano, T., et al., "Expression Status of p16 Protein is Associated with Human Papillomavirus Oncogenic Potential in Cervical and Genital Lesions," Am. J. Pathol., 1998, pp. 1741-1748, vol. 153, No. 6.
Serrano, M. et al., "A new regulatory motif in cell-cycle control causing specific inhibition of cyclin D/CDK4," Nature, Dec. 16, 1993, pp. 704-707, vol. 366.
Shalaby, M. et al., "Development of Humanized Bispecific Antibodies Reactive with Cytotoxic Lymphocytes and Tumor Cells Overexpressing the HER2 Protooncogene," J. Exp. Med., Jan. 1992, pp. 217-225, vol. 175, The Rockefeller University Press.

Sherr, C., "The INK4a/ARF Network in Tumor Suppression," Nat. Rev. Mol. Cell Bio., Oct. 2001, pp. 731-737, vol. 2.
Shim, C. et al., "Profiling of differentially expressed genes in human primary cervical cancer by complementary DNA expression array," Clin. Cancer Res., Dec. 1998, pp. 3045-3050, vol. 4.
Sivam, G. et al., "Therapeutic Efficacy of a Doxorubicin Immunoconjugate in a Preclinical Model of Spontaneous Metastatic Human Melanoma," Cancer Res., Jun. 1, 1995, pp. 2352-2356, vol. 55.
Song, C. et al., "Combined Cytolytic Effect of X Irradiation and Cell-Mediated Immune Reactions on Tumor Cells in Vitro," Radiology, Apr. 1974, pp. 213-214, vol. 111.
Stratton, J. et al., "Imaging Arterial Thrombosis: Comparison of Technetium-99m-Labeled Monoclonal Antifibrin Antibodies and Indium-111-Platelets," J. Nucl. Med., Nov. 1994, pp. 1731-1737, vol. 35, No. 11.
Sudarsanam, S., "Structural Diversity of Sequentially Identical Subsequences of Proteins: Identical Octapeptides Can Have Different Conformations," Proteins: Structure, Function, and Genetics, 1998, pp. 228-231, vol. 30, Wiley-Liss, Inc.
Suneja, S. et al., "Quantification of a neurotrophin receptor from submilligram quantities of brain tissue using Western blotting," Brain Res. Protocols, 1998, pp. 88-93, vol. 3.
Supplementary European Search Report from European Patent Application No. 00935839.0 dated Mar. 31, 2003, 5 pages.
Takeuchi, H. et al., "Altered p16/MTS1/CDKN2 and cyclin D1/PRAD-1 gene expression is associated with the prognosis of squamous cell carcinoma of the esophagus," Clin. Cancer Res., Dec. 1997, pp. 2229-2236, vol. 3.
Tam, S. et al., "Differential Expression and Cell Cycle Regulation of the Cyclin-dependent Kinase 4 Inhibitor p16Ink4," Cancer Res., Nov. 15, 1994, pp. 5816-5820, vol. 54.
Tsujie, M. et al., "Expression of Tumor Suppressor Gene p16INK4 Products in Primary Gastric Cancer," Oncology, 2000, pp. 126-136, vol. 58.
Wang, H. et al., "TIP-1 Translocation onto the Cell Plasma Membrane is a Molecular Biomarker of Tumor Response to Ionizing Radiation," PLoS One, Aug. 2010, pp. 1-12, vol. 5, No. 8, e12051.
Weichselbaum, R. et al., "Gene Therapy Targeted by Radiation Preferentially Radiosensitizes Tumor Cells," Cancer Res., Aug. 15, 1994, pp. 4266-4269, vol. 54.
Wentzensen, N. et al., "Identification of High-Grade Cervical Dysplasia by the Detection of p16INK4a in Cell Lysates Obtained From Cervical Samples," Cancer, Nov. 1, 2006, pp. 2307-2313, vol. 107, No. 9.
International Preliminary Examination Report from related WIPO Patent Application No. PCT/US04/034719, dated Oct. 14, 2005, 3 pages.
International Preliminary Examination Report from related WIPO Patent Application No. PCT/US2000/011485 dated Jul. 25, 2001, 6 pages.
International Preliminary Report on Patentability from related WIPO Patent Application No. PCT/US2005/031367 dated Oct. 30, 2007, 4 pages.
International Preliminary Report on Patentability from related WIPO Patent Application No. PCT/US2006/027283, dated Jan. 16, 2008, 4 pages.
International Search Report from related WIPO Patent Application No. PCT/US02/030917, dated Feb. 10, 2005, 3 pages.
International Search Report from related WIPO Patent Application No. PCT/US2006/027283, dated Mar. 13, 2007, 2 pages.
International Search Report from related WIPO Patent Application No. PCT/US05/031367 dated Oct. 11, 2007, 1 page.
International Search Report from related WIPO Patent Application No. PCT/US2000/011485 dated Oct. 4, 2000, 4 pages.
International Search Report from related WIPO Patent Application No. PCT/US04/034719 dated Jan. 26, 2005, 1 page.
Interview Summary from related U.S. Appl. No. 11/413,783, dated May 6, 2010, 3 pages.
Interview Summary from related U.S. Appl. No. 12/111,693, dated Dec. 22, 2010, 2 pages.

(56) References Cited

OTHER PUBLICATIONS

Ito, T. et al., "Preclinical Assessments of 90Y-labeled C110 Anti-Carcinoembryonic Antigen Immunotoxin: A Therapeutic Immunoconjugate for Human Colon Cancer," Cancer Res., Jan. 1, 1991, pp. 255-260, vol. 51.
Jahroudi, N. et al., "Ionizing irradiation increases transcription of the von Willebrand factor gene in endothelial cells," Blood, Nov. 15, Jan. 1996, pp. 3801-3814, vol. 88, No. 10.
Jain, R., "Barriers to Drug Delivery in Solid Tumors," Scientific American, Jul. 1994, pp. 58-65, vol. 271.
Johnson, T. et al., "Therapy of B-cell lymphomas with monoclonal antibodies and radioimmunoconjugates: the Seattle experience," Ann. Hematol., 2000 pp. 175-182, vol. 79.
Kastan, M. et al., "ATM kinase modulation for screening and therapies," Database HCAPLUS on STN, 2000, Abstract WO00/47760, Accession No. 2000:573954, Registry No. 288259-02-9 for SEQ ID No. 8 and SEQ ID No. 10 and Registry No. 288259-18-7 for SEQ ID No. 13, 1 page.
Kelley, M. et al., "CDKN2 in HPV-Positive and HPV-Negative Cervical-Carcinoma Cell Lines," Int. J. Cancer, 1995 pp. 226-230, vol. 63.
Khleif, S. et al., "Inhibition of cyclin D-CDK4/CDK6 activity is associated with an E2F-mediated induction of cyclin kinase inhibitor activity," PNAS, Apr. 1996, pp. 4350-4354, vol. 93.
Kim, J. et al., "Absence of p15INK4B and p16INK4A Gene Alterations in Primary Cervical Carcinoma Tissues and Cell Lines with Human Papillomavirus Infection," Gynecologic Oncology, 1998, pp. 75-79, vol. 70, Article No. GO985041.
Kim, Y. et al., "Underexpression of Cyclin-Dependent Kinase (CDK) Inhibitors in Cervical Carcinoma," Gynecologic Oncology, 1998, pp. 38-45, vol. 71, Article No. GO985134.
Klaes, R. et al., "Overexpression of p16INK4A as a Specific Marker for Dysplastic and Neoplastic Epthelial Cells of the Cervis Uteri," Int. J. Cancer, 2001, pp. 276-284, vol. 92.
Koivunen, E. et al., "Isolation of a Highly Specific Ligand for the alpha5beta1 Integrin from a Phage Display Library," J. Cell Biol., 1994, pp. 373-380, vol. 124.
Koivunen, E. et al., "Selection of Peptides Binding to the alpha5beta1 Integrin from Phage Display Library," J. Bio. Chem., Sep. 25, 1993, pp. 20205-20210, vol. 268, No. 27.
Krauer, K. et al., "Antitumor Effect of 2'-Deoxy-5-fluorouridine Conjugates against a Murine Thymoma and Colon Carcinoma Xenografts," Cancer Res., Jan. 1, 1992, pp. 132-137, vol. 52.
Kurnik, B. et al., "Prospective study of atrial natriuretic peptide for the prevention of radio-contrast-induced nephropathy," Database HCAPLUS on STN, Abstract, Am. J. Kidney Disease, 1998, Accession No. 1998:248017, Registry No. 95896-08-5 for atrial natriuetic peptide-25, for SEQ ID No. 11, 1 page.
Lieberman, H. et al., "A human homolog of the Schizosaccharomyces pombe rad9+ checkpoint control gene," PNAS, Nov. 1996, pp. 13890-13895, vol. 93.
Liggett, W. et al., "Role of the p16 Tumor Suppressor Gene in Cancer," J. Clin. Onocl., Mar. 1998, pp. 1197-1206, vol. 16, No. 3.
Llovet, J. et al., "Arterial embolisation or chemoembolisation versus symptomatic treatment in patients with unresectable hepatocellular carcinoma: a randomised controlled trial," Lancet, May 18, 2002, pp. 1734-1739, vol. 359.
Mao, C. et al., "Evaluation of a new p16INK4a ELISA test and a high-risk HPV DNA test for cervical cancer screening: Results from proof-of-concept study," Int. J. Cancer, 2007, pp. 2435-2438, vol. 120.
Martin, F., et al., "Targeted Retroviral Infection of Tumor Cells by Receptor Cooperation," J. Virology, Feb. 2003, pp. 2753-2756, vol. 77, No. 4.
Mauceri, H. et al., "Tumor Necrosis Factor alpha (TNF-alpha) Gene Therapy Targeted by Ionizing Radiation Selectively Damages Tumor Vasculature," Cancer Res., Oct. 1, 1996, pp. 4311-4314, vol. 56.
Milde-Langosch, K. et al., "P16/MTS1 and pRB expression in endometrial carcinomas," Virchows Arch, 1999, pp. 23-28, vol. 434.
Milde-Langosch, K. et al., "p16/MTS1 Inactivation in Ovarian Carcinomas: High Frequency of Reduced Protein Expression Associated With Hyper-Methylation or Mutation in Endometrioid and Mucinous Tumors," Int. J. Cancer (Pred. Oncol.), 1998, pp. 61-65, vol. 79.
Molema, G. et al., "Tumor Vascular Endothelium: Barrier or Target in Tumor Directed Drug Delivery and Immunotherapy," Pharm. Res., 1997, pp. 2-10, vol. 14, No. 1.
Munro, S. et al., "An Hsp70-like Protein in the ER: Identity with the 78 kd Glucose-Regulated Protein and Immunoglobulin Heavy Chain Binding Protein," Cell, Jul. 18, 1986, pp. 291-300, vol. 46, Cell Press.
Myung, N. et al., "Loss of p16 and p27 is associated with progression of human gastric cancer," Cancer Letters, 2000, pp. 129-136, vol. 153.
Nakao, Y. et al., "Induction of p16 during immortalization by HPV 16 and 18 and not during malignant transformation," British J. Cancer, 1997, pp. 1410-1416, vol. 75, No. 10.
Notice of Allowance from related U.S. Appl. No. 09/914,605, dated Dec. 14, 2005, 3 pages.
Notice of Allowance from related U.S. Appl. No. 10/689,006, dated Jul. 24, 2007, 6 pages.
Notice of Allowance from related U.S. Appl. No. 11/413,783, dated May 27, 2010, 4 pages.
Notice of Allowance from related U.S. Appl. No. 11/413,783, dated Sep. 14, 2010, 4 pages.
Notice of Allowance from related U.S. Appl. No. 11/592,451, dated Sep. 12, 2011, 5 pages.
Notice of Allowance from related U.S. Appl. No. 11/953,780, dated Apr. 29, 2011, 5 pages.
Notice of Allowance from related U.S. Appl. No. 13/195,570, dated Aug. 12, 2013, 9 pages.
Notice of Allowance from related U.S. Appl. No. 13/766,310, dated Feb. 19, 2014, 7 pages.
Notice of Allowance, with Examiner-Initiated Interview Summary, from related U.S. Appl. No. 13/018,747, dated Nov. 6, 2012, 8 pages.
Notice of Allowance, with Examiner-Initiated Interview Summary, from related U.S. Appl. No. 11/183,325, dated Oct. 28, 2010, 9 pages.
Notice of Allowance, with Interview Summary, from related U.S. Appl. No. 12/111,693, dated Feb. 22, 2011, 10 pages.
Nuovo, G. et al., "In situ detection of the hypermethylation-induced inactivation of the p16 gene as an early event in oncogenesis," PNAS, Oct. 26, 1999, pp. 12754-12759, vol. 96, No. 22.
O'Brien, P. et al., "Antibody Phage Display: Methods and Protocols," E-Streams, Dec. 2002, pp. 1-2, vol. 5, No. 12.
Campath® Fact Sheet, www.campath.com/medpros/factsheet.html, Aug. 8, 2003, 3 pages.
Hellström, I. et al., "Immunoconjugates and immunotoxins for therapy of solid tumors," Cancer Chemother. Pharmacol., 1996, vol. 38, Suppl:S35-S36.
Herceptin, Mechanism of Action, www.herceptin.com/herceptin/physician/j_profile/mechanism.htm, Genentech, Aug. 6, 2003, 3 pages.
Pasqualini, R. et al., "Tissue Targeting with phage peptide libraries," Molecular Psychiatry, Dec. 1996, p. 423, vol. 1, No. 6.
Rituxan, Mechanism of Action: Targeted Therapy Provides a Unique Profile of Efficacy, www.rituxan.com/rituxan/professional/e_product_info/mode_of_action.htm, Aug. 8, 2003, 3 pages.
Zevalin, First in Radioimmunotherapy: Mechanism of Action, www.zevalin.com/html/HealthcareProfessionals/ProductInformation/productInform . . . , Aug. 8, 2003, 1 page.
Arap, W. et al., "Cancer Treatment by Targeted Drug Delivery to Tumor Vasculature in a Mouse Model," Science, Jan. 16, 1998, pp. 377-380, vol. 279.
Baillie, C.T. et al., "Tumor vasculature—a potential therapeutic agent," British J. Can., 1995, pp. 257-267, vol. 72.
Barry, M. et al., "Toward cell-targeting gene therapy vectors: Selection of cell-binding peptides from random peptide-presenting phage libraries," Nature Medicine, Mar. 3, 1996, pp. 299-305, vol. 2, No. 3.
Bender, H. et al., "Enhancement of Monoclonal Antibody Efficacy: The Effect of External Beam Radiation," Hybridoma, 1995, pp. 129-134, vol. 14, No. 2.
Bender, H. et al., "External Beam Radiation Enhances Antibody Mediated Radiocytotoxicity in Human Glioma Cells in Vitro," Anticancer Res., 1997, pp. 1797-1802, vol. 17.
Bhakdi, S., "Removal of SDS From Proteins for Immunochemical Analyses: A Simple Method Utilizing Ultracentrifugation in Sucrose

(56) References Cited

OTHER PUBLICATIONS

Density Gradients Containing Non-Ionic Detergent," J. Biochem. Biophys. Methods, 1980, pp. 79-90, vol. 2.
Bird, R. et al., "Single-Chain Antigen-Binding Proteins," Science, New Series, Oct. 21, 1988, pp. 423-426, vol. 242, No. 4877.
Boothman, D. et al., "Induction of Tissue-type Plasminogen Activator by Ionizing Radiation in Human Malignant Melanoma Cells," Cancer Res., 1991, pp. 5587-5595, vol. 51.
Brach, M. et al, "Ionizing Radiation Induces Expression of Interleukin 6 by Human Fibroblasts Involving Activation of Nuclear Factor-kB," J. Biolog. Chem., Apr. 25, 1993, pp. 8466-8472, vol. 268, No. 12.
Burg, M. et al., "NG2 Proteoglycan-binding Peptides Target Tumor Neovasculature," Cancer Res., Jun. 15, 1999, pp. 2869-2874, vol. 59.
Cai, X. et al, "Anti-melanoma antibodies from melanoma patients immunized with genetically modified autologous tumor cells: Selection of specific antibodies from single-chain Fv fusion phage libraries," PNAS, Jul. 1995, pp. 6537-6541, vol. 92.
Castellano, M. et al., "CDKN2A/p16 Is Inactivated in Most Melanoma Cell Lines," Cancer Res, 1997, pp. 4868-4875, vol. 57.
Chen, C. et al., "Reactivity of Synthetic Peptide Analogs of Adhesive Proteins in Regard to the Interaction of Human Endothelial Cells With Extracellular Matrix," Blood, May 15, 1991, pp. 2200-2206, vol. 77, No. 10.
Cheresh, D. et al., "Human endothelial cells synthesize and express an Arg-Gly-Asp-directed adhesion receptor involved in attachment to fibrinogen and von Willebrand factor," PNAS, Sep. 1987, pp. 6471-6475, vol. 84.
Croce, C. et al., "Cloning of human RAD54 gene homolog and its diagnostic and therapeutic uses," Database HCAPLUS on STN, 1998, Abstract EP0844305, Accession No. 1998:365000, Registry No. 208601-90-5 for human rad54 for SEQ ID NO:12, 1 page.
Dai, C. et al., "p16INK4a Expression Begins Early in Human Colon Neoplasia and Correlates Inversely With Markers of Cell Proliferation," Gastroenterology, 2000, pp. 929-942, vol. 119.
De Bree, R. et al., "Selection of monoclonal antibody E48 IgG or U36 IgG for adjuvant radioimmunotherapy in head and neck cancer patients," British J. Cancer, 1997, pp. 1049-1060, vol. 75, No. 7.
Dimitriadis, G., "Effect of Detergents on Antibody-Antigen Interaction," Anal. Biochem., 1979, pp. 445-451, vol. 98.
Dolganov, G., "The human RAD50 and Septin-2 genes and their roles in myelodysplastic diseases and their diagnostic and therapeutic uses," Database HCAPLUS on STN, 1997, Abstract WO97/27284, Accession No. 1997:513697, Registry No. 194813-18-8 for human clone B15.2, for SEQ ID NO:8, 1 page.
Edmonds, S., "Antibody-Targeted Chemotherapy with Mylotarg Shows Promise for Many Adults with Deadly Form of Leukemia," American Society of Clinical Oncology 36th Annual Meeting, May 21, 2000, New Orleans, Louisiana.
Ellerby, H. et al., "Anti-cancer activity of targeted pro-apoptotic peptides," Nature Medicine, Sep. 1999, pp. 1032-1038, vol. 5, No. 9.
Evan, G. et al., "Isolation of Monoclonal Antibodies Specific for Human c-myc Proto-Oncogene Product," Mol. Cell Biol., Dec. 1985, pp. 3610-3616, vol. 5, No. 12.
Figini, M. et al., "Panning Phage Antibody Libraries on Cells: Isolation of Human Fab Fragments against Ovarian Carcinoma Using Guided Selection," Cancer Res., Mar. 1, 1998, pp. 991-996, vol. 58.
Fox, S. et al., "Markers of tumor angiogenesis: clinical applications in prognosis and anti-angiogenic therapy," Investigational New Drugs, 1997, pp. 15-28, vol. 15.
Geradts, J. et al., "Frequent Loss of KAI1 Expression in Squamous and Lymphoid Neoplasms," Am. J. Path., Jun. 1999, pp. 1665-1671, vol. 154, No. 6.
Geradts, J. et al., "Immunohistochemical Detection of the Cyclin-dependent Kinase Inhibitor 2/Multiple Tumor Suppressor Gene 1 (CDKN2/MTS1) Product p16INK4A in Archival Human Solid Tumors: Correlation with Retinoblastoma Protein Expression," Cancer Res., 1995, pp. 6006-6011, vol. 55.
Goldman, C. et al., "Targeted Gene Delivery to Kaposi's Sarcoma Cells via the Fibroblast Growth Factor Receptor," Cancer Res., Apr. 15, 1997, pp. 1447-1451, vol. 57.
Gump, J. et al., "Phosphorylation of p16INK4A Correlates with Cdk4 Association," J. Biol. Chem., Feb. 28, 2003, pp. 6619-6622, vol. 278, No. 9.
Hallahan, D. et al., "Ionizing Radiation Mediates Expression of Cell Adhesion Molecules in Distinct Histological Patterns within the Lung," Cancer Res., Jun. 1, 1997, pp. 2096-2099, vol. 57.
Hallahan, D. et al., "Cell Adhesion Molecules Mediate Radiation-induced Leukocyte Adhesion to the Vascular Endothelium," Cancer Res., Nov. 15, 1996, pp. 5150-5155, vol. 56.
Hallahan, D. et al., "c-jun and Egr-1 Participate in DNA Synthesis and Cell Survival in Response to Ionizing Radiation Exposure," J. Bio. Chem., Dec. 22, 1995, pp. 30303-30309, vol. 270, No. 51.
Hallahan, D. et al., "E-selectin gene induction by ionizing radiation is independent of cytokine induction," Biochem. Biophys. Res. Commun., Dec. 26, 1995, pp. 784-795, vol. 217, No. 3.
Hallahan, D. et al., "Integrin-mediated targeting of drug delivery to irradiated tumor blood vessels," Cancer Cell, Jan. 2003, pp. 63-74, vol. 3.
Hallahan, D. et al., "Intercellular adhesion molecule 1 knockout abrogates radiation induced pulmonary inflammation," PNAS, Jun. 1997, pp. 6432-6437, vol. 94.
Hallahan, D. et al., "Nuclear Factor kB Dominant Negative Genetic Constructs Inhibit X-ray Induction of Cell Adhesion Molecules in the Vascular Endothelium," Cancer Res., Dec. 1, 1998, pp. 5484-5488, vol. 58.
Hallahan, D. et al., "Radiation Signaling Mediated by Jun Activation following Dissociation from a Cell Type-specific Repressor," J. Bio. Chem., Mar. 5, 1993, pp. 4903-4907, vol. 268, No. 7.
Hallahan, D. et al., "Spatial and temporal control of gene therapy using ionizing radiation," Nature Medicine, Aug. 1995, pp. 786-791, vol. 1, No. 8.
Hallahan, D. et al., Targeting drug delivery to radiation-induced neoantigens in tumor microvasculature, J. Controlled Release, 2001, pp. 183-191, vol. 74.
Hallahan, D. et al., "X-Ray-induced P-selectin Localization to the Lumen of Tumor Blood Vessels," Cancer Res., Nov. 15, 1998, pp. 5216-5220, vol. 58.
Hallahan, D., "Radiation-Mediated Gene Expression in the Pathogenesis of the Clinical Radiation Response," Seminars Radiat. Oncol., Oct. 1996, pp. 250-267, vol. 6, No. 4.
Hallahan, D., et al., "Radiation-Mediated Control of Drug Delivery," Am. J. Clin. Oncol., 2001, pp. 473-480, vol. 24, No. 5.
Harari, 0. et al., "Targeting an adenoviral gene vector to cytokine-activated vascular endothelium via E-selectin," Gene Therapy, 1999, pp. 801-807, vol. 6, Stockton Press.
Hareyama, M. et al., "The Effect of Radiation on the Expression of Intercellular Adhesion Molecule-1 of Human Adenocarcinoma Cells," Int. J. Rad. Oncol. Biol. Phys., 1998, pp. 691-696, vol. 40, No. 3.
Hariri, G. et al., "Radiation-Guided Drug Delivery to Mouse Models of Lung Cancer," Clin. Cancer Res., Oct. 15, 2010, pp. 4968-4977, vol. 16, No. 20.
He, X-S. et al., "Expression, deleton and mutation of p16 gene in human gastric cancer," World J. Gastroenterol., 2001, pp. 515-521, vol. 7, No. 4.
Hirata, "Fate of Intravenously Injected Human Tumor Cells in the Lung of Nude Mice Following Whole-Body X-Irradiation," Invasion Metastasis, 1985, pp. 61-70, [Abstract Only].
Hirata, H. et al., "Artificial Metastases and Decrease of Fibrinolysis in the Nude Mouse Lung After Hemithoracic Irradiation," Clin. Expl. Metatasis, 1984, pp. 311-319, vol. 2, No. 4, [Abstract Only].
Humira™ (adalimumab) Package Insert, Dec. 20, 2002, 16 pages.
Huston, J., "Protein engineering of antibody binding sites: Recovery of specific activity in an anti-digoxin single-chain Fv analogue produced in *Escherichia coli,* " PNAS, Aug. 1998, pp. 5879-5883, vol. 85.
Ikeda, K. et al., "Extraction and Analysis of Diagnostically Useful Proteins from Formalin-fixed, Paraffin-embedded Tissue Sections," J. Histochem. Cytochem., 1998, pp. 397-403, vol. 46, No. 3.

\* cited by examiner

LIGANDS TO RADIATION-INDUCED MOLECULES

CROSS REFERENCE TO RELATED APPLICATIONS

This application is a continuation of U.S. patent application Ser. No. 13/766,310, filed Feb. 13, 2013, which is a divisional of U.S. patent application Ser. No. 13/018,747, filed Feb. 1, 2011, which is a divisional of U.S. patent application Ser. No. 11/183,325, filed Jul. 15, 2005, which is a continuation-in-part of U.S. patent application Ser. No. 10/259,087, filed Sep. 27, 2002, which is based on and claims priority to U.S. Provisional Patent Application Ser. No. 60/328,123, filed Oct. 3, 2001, each of which is hereby incorporated by reference in their entireties.

GRANT STATEMENT

This work was supported by grants CA58508, CA70937, CA89888, CA89674, and CA90949 from the U.S. National Institute of Health. Thus, the U.S. government has certain rights in the presently disclosed subject matter.

TECHNICAL FIELD

The presently disclosed subject matter generally relates to ligands for radiation guided delivery of an active agent. More particularly, the presently disclosed subject matter provides a method for in vivo panning of diverse molecules for isolation of targeting ligands that specifically bind an irradiated tumor. Also provided are novel targeting ligands, and therapeutic and diagnostic uses of the same.

TABLE OF ABBREVIATIONS

AR—autoradiography
CPM—counts per minute
CT—computerized tomography
HPLC—high performance liquid chromatography
IP—imaging plate
LUER—low energy high resolution
MRI—magnetic resonance imaging
NM—nuclear magnetic
OD—optical density
PCR—Polymerase Chain Reaction
PET—positron emission spectroscopy
PFU—plaque-forming unit
ROI—region of interest
SPECT—single photon emission computed tomography

REFERENCE TO SEQUENCE LISTING

A paper copy of the sequence listing and a computer readable form of the same sequence listing are appended below and herein incorporated by reference. The information recorded in computer readable form is identical to the written sequence listing, according to 37 C.F.R. 1.821(f).

BACKGROUND

Tumor-specific drug delivery has the potential to minimize toxicity to normal tissues and improve the bioavailability of therapeutic agents to tumor cells (Hallahan et al., 1995b; Arap et al., 1998). Targeting ligands include antibodies and peptides that accumulate in tumors by specific binding to target molecules present on tumor vasculature, endothelial cells associated with tumor vasculature, and tumor cells. Effective target molecules are generally cell surface receptors or other molecules present at the exterior of tumor cells such that they are accessible to targeting ligands (Hallahan et al., 2001a).

Existing site-specific drug delivery systems include ligands that recognize a tumor marker such as Her2/neu (v-erb-b2 avian erythroblastic leukemia viral oncogene homologue 2), CEA (carcinoembryonic antigen) (Ito et al., 1991), and breast cancer antigens (Manome et al., 1994; Kirpotin et al., 1997; Becerril et al., 1999). See also PCT International Publication No. WO 98/10795. In an effort to identify ligands that are capable of targeting to multiple tumor types, targeting ligands have been developed that bind to target molecules present on tumor vasculature (Baillie et al., 1995; Pasqualini & Ruoslahti, 1996; Arap et al., 1998; Burg et al., 1999; Ellerby et al., 1999).

Despite these advances, current methods for targeted drug delivery are hindered by targeting ligands that also bind normal tissues and/or a lack of targeting ligands that bind multiple tumor types. Ideally, a targeting molecule should display specific targeting in the absence of substantial binding to normal tissues, and a capacity for targeting to a variety of tumor types and stages. Thus, there exists a long-felt need in the art for methods and compositions to achieve site-specific, tumoral delivery of therapeutic and/or diagnostic agents.

To meet this need, the presently disclosed subject matter provides methods for identifying ligands that bind to irradiated tumors, and ligands that have been bind irradiated tumors and tissues. Such ligands are useful for x-ray guided drug delivery, among other applications.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

The presently disclosed subject matter provides methods for identifying a molecule that binds to an irradiated tumor in a subject. In some embodiments, the method comprises (a) exposing a tumor to ionizing radiation; (b) administering to a subject a library of diverse molecules; and (c) isolating one or more molecules of the library from the tumor, whereby a molecule that binds an irradiated tumor is identified.

The presently disclosed subject matter also provides compositions for guided targeting. In some embodiments, a composition for guided targeting comprises one or more targeting ligands comprising an amino acid sequence as set forth in SEQ ID NOs: 21-55. In some embodiments, the one or more targeting ligands bind to one or more of an irradiated glioma, a melanoma, and a lung carcinoma. In some embodiments, the one or more targeting ligands bind to an irradiated tumor of two or more tumor types, and in some embodiments, the one or more targeting ligands bind to an irradiated tumor of three or more tumor types. In some embodiments, the one or more targeting ligands bind to an irradiated glioma, a melanoma, and a lung carcinoma.

In some embodiments of the presently disclosed subject matter, the composition further comprises a detectable label, a therapeutic agent, a drug carrier, or combinations thereof. In some embodiments, the detectable label is an in vivo detectable label that can be detected using magnetic resonance imaging, scintigraphic imaging, ultrasound, or fluorescence. In some embodiments, the in vivo detectable label comprises a radionuclide label selected from the group consisting of $^{131}$I or $^{99m}$Tc. In some embodiments, the therapeutic agent is selected from the group consisting of a radionuclide, a cytotoxin, a therapeutic gene, and a chemotherapeutic agent. In some embodiments, the drug carrier is selected from the group consisting of a viral vector, a liposome, a plasmid, a microcapsule, and combinations thereof.

The presently disclosed subject matter also provides methods for detecting a tumor in a subject. In some embodiments, the method comprises (a) exposing a suspected tumor to ionizing radiation; (b) administering to the subject a composition comprising one or more targeting ligands comprising an amino acid sequence as set forth in SEQ ID NOs: 21-55; and (c) detecting the detectable label to thereby detect the tumor. In some embodiments, the exposing comprises exposing the tumor to less than about 2 Gy ionizing radiation, in some embodiments the exposing comprises exposing the tumor to at least about 2 Gy ionizing radiation, and in some embodiments the exposing comprises exposing the tumor to about 10 Gy to about 20 Gy ionizing radiation. In some embodiments, the administering comprises administering the targeting ligand by intravascular provision. In some embodiments, the administering comprises administering the targeting ligand subsequent to radiation exposure. In some embodiments, the administering comprises administering the targeting ligand 0 hours to about 24 hours following radiation exposure. In some embodiments, the administering comprises administering the targeting ligand about 4 hours to about 24 hours following radiation exposure. In some embodiments, the detecting comprises detecting the radionuclide label using positron emission tomography, single photon emission computed tomography, gamma camera imaging, or rectilinear scanning. In some embodiments, the disclosed detection methods further comprise simultaneously detecting two or more tumors in the subject. In some embodiments, the two or more tumors in a subject comprise two or more tumor types.

The presently disclosed subject matter also provides methods for guided delivery of a therapeutic composition, a diagnostic composition, or a combination thereof, to a tumor in a subject. In some embodiments, the method comprises (a) exposing the tumor to ionizing radiation; and (b) administering to the subject a therapeutic composition, a diagnostic composition, or a combination thereof, wherein the therapeutic composition, diagnostic composition, or the combination thereof comprises a composition comprising one or more targeting ligands comprising an amino acid sequence as set forth in SEQ ID NOs: 21-55; whereby the therapeutic composition, diagnostic composition, or combination thereof is selectively targeted to the tumor. In some embodiments, the tumor is a primary or a metastasized tumor. In some embodiments, the tumor is selected from a tumor selected from the group consisting of bladder carcinoma, breast carcinoma, cervical carcinoma, cholangiocarcinoma, colorectal carcinoma, gastric sarcoma, glioma, lung carcinoma, lymphoma, melanoma, multiple myeloma, osteosarcoma, ovarian carcinoma, pancreatic carcinoma, prostate carcinoma, stomach carcinoma, a head tumor, a neck tumor, and a solid tumor. In some embodiments, the tumor is selected from the group consisting of a glioma, a melanoma, and a lung carcinoma. In some embodiments, the exposing comprises exposing the tumor to at least about 2 Gy ionizing radiation. In some embodiments, the administering comprises administering the targeting ligand by intravascular provision. In some embodiments, the administering comprises administering the targeting ligand subsequent to radiation exposure. In some embodiments, the administering comprises administering the targeting ligand 0 hours to about 24 hours following radiation exposure. In some embodiments, the subject is a warm-blooded vertebrate (for example, a human).

The presently disclosed subject matter also provides methods for of guided delivery of a therapeutic composition, a diagnostic composition, or a combination thereof, to a nucleus of a cell. In some embodiments, the method comprises (a) exposing the cell to ionizing radiation; and (b) contacting the cell with a therapeutic composition, a diagnostic composition, or a combination thereof, wherein the therapeutic composition, diagnostic composition, or the combination thereof comprises a composition comprising one or more targeting ligands comprising an amino acid sequence as set forth in SEQ ID NOs: 47-55, whereby the therapeutic composition, diagnostic composition, or combination thereof enters the cell and is selectively targeted to the nucleus of the cell. In some embodiments, the exposing comprises exposing the cell to at least about 2 Gy ionizing radiation. In some embodiments, the cell is present within a warm-blooded vertebrate. In some embodiments, the cell is present within a tumor selected from the group consisting of a bladder carcinoma, a breast carcinoma, a cervical carcinoma, a cholangiocarcinoma, a colorectal carcinoma, a gastric sarcoma, a glioma, a lung carcinoma, a lymphoma, a melanoma, a multiple myeloma, an osteosarcoma, an ovarian carcinoma, a pancreatic carcinoma, a prostate carcinoma, a stomach carcinoma, a head tumor, a neck tumor, and a solid tumor. In some embodiments, the contacting comprises administering the targeting ligand to the warm-blooded vertebrate by intravascular provision. In some embodiments, the administering comprises administering the targeting ligand subsequent to radiation exposure. In some embodiments, the administering comprises administering the targeting ligand 0 hours to about 24 hours following radiation exposure.

The methods and compositions of the presently disclosed subject matter can be employed for the treatment and/or detection of a tumor in any subject. In some embodiments, the subject is a warm-blooded vertebrate. In some embodiments, the subject is a human.

The methods and compositions of the presently disclosed subject matter can be employed for the treatment and/or detection of any tumor in a subject. In some embodiments, the tumor comprises a tumor selected from the group consisting of bladder carcinoma, breast carcinoma, cervical carcinoma, cholangiocarcinoma, colorectal carcinoma, gastric sarcoma, glioma, lung carcinoma, lymphoma, melanoma, multiple myeloma, osteosarcoma, ovarian carcinoma, pancreatic carcinoma, prostate carcinoma, stomach carcinoma, a head, a neck tumor, and a solid tumor. In some embodiments, the tumor is selected from the group consisting of a glioma, a melanoma, and a lung carcinoma.

Accordingly, it is an object of the presently disclosed subject matter to provide novel targeting ligands that bind irradiated tumors and therapeutic and/or diagnostic methods using the same. This and others objects are achieved in whole or in part by the presently disclosed subject matter.

An object of the presently disclosed subject matter having been stated above, other objects and advantages of the presently disclosed subject matter will become apparent to those skilled in the art after a study of the following description and non-limiting Examples.

DETAILED DESCRIPTION

I. Definitions

While the following terms are believed to be well understood by one of ordinary skill in the art, the following definitions are set forth to facilitate explanation of the invention.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in this application, including the claims. Thus, for example, reference to "a cell" (e.g., "a PEP") includes a plurality of such cells (e.g., a plurality of PEPS), and so forth.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

As used herein, the term "cell" refers not only to the particular subject cell (e.g., a living biological cell), but also to the progeny or potential progeny of such a cell. Because certain modifications can occur in succeeding generations due to either mutation or environmental influences, such progeny might not, in fact, be identical to the parent cell, but are still included within the scope of the term as used herein.

The term "ligand" as used herein refers to a molecule or other chemical entity having a capacity for binding to a target. A ligand can comprise a peptide, an oligomer, a nucleic acid (e.g., an aptamer), a small molecule (e.g., a chemical compound), an antibody or fragment thereof, a nucleic acid-protein fusion, and/or any other affinity agent.

The term "small molecule" as used herein refers to a compound, for example an organic compound, with a molecular weight in some embodiments of less than about 1,000 daltons, in some embodiments less than about 750 daltons, in some embodiments less than about 600 daltons, and in some embodiments less than about 500 daltons. A small molecule also has a computed log octanol-water partition coefficient in some embodiments in the range of about −4 to about +14, and in some embodiments in the range of about −2 to about +7.5.

The term "target tissue" as used herein refers to an intended site for accumulation of a ligand following administration to a subject. For example, the methods disclosed herein can employ a target tissue comprising an irradiated tumor.

The term "control tissue" as used herein refers to a site suspected to substantially lack binding and/or accumulation of an administered ligand. For example, in accordance with the methods of the presently disclosed subject matter, a non-irradiated tumor and a non-cancerous tissue are control tissues.

The terms "target" or "target molecule" as used herein each refer to any substance that is specifically bound by a ligand. Thus, the term "target molecule" encompasses macromolecules including but not limited to proteins, nucleic acids, carbohydrates, lipids, and complexes thereof.

The terms "radiation-induced target" and "radiation-induced tumor target" as used herein each refer to a target molecule in a tumor whose expression, localization, or ligand-binding capacity is induced by radiation. Such a target molecule can comprise a molecule at the surface of a tumor cell, within a tumor cell, or in the extracellular matrix surrounding a tumor cell. Alternatively, a target molecule can comprise a molecule present at the surface of or within a vascular endothelial cell, or at the surface of or within a blood component such as a platelet or a leukocyte.

The term "induce", as used herein to refer to changes resulting from radiation exposure, encompasses activation of gene transcription or regulated release of proteins from cellular storage reservoirs to vascular endothelium. Alternatively, induction can refer to a process of conformational change, also called activation, such as that displayed by the glycoprotein IIb/IIIa integrin receptor upon radiation exposure (Staba et al., 2000; Hallahan et al., 2001a). See also U.S. Pat. No. 6,159,443. Additional proteins undergo conformational changes in response to radiation or other stimuli (e.g., co-culture with tumor cells), and these conformational change are also intended to be encompassed by the term "induction". An exemplary protein that undergoes conformational changes in response to co-culture with tumor cells and/or exposure to radiation is perlecan (GENBANK® Accession No. P98160; SEQ ID NO: 56).

The terms "targeting" or "homing", as used herein to describe the in vivo activity of a ligand following administration to a subject, each refer to the preferential movement and/or accumulation of a ligand in a target tissue as compared with a control tissue.

The terms "selective targeting" of "selective homing" as used herein each refer to a preferential localization of a ligand that results in an amount of ligand in a target tissue that is in some embodiments about 2-fold greater than an amount of ligand in a control tissue, in some embodiments about 5-fold or greater than an amount of ligand in a control tissue, and in some embodiments an amount that is about 10-fold or greater than an amount of ligand in a control tissue. The terms "selective targeting" and "selective homing" also refer to binding or accumulation of a ligand in a target tissue concomitant with an absence of targeting to a control tissue, in some embodiments the absence of targeting to all control tissues.

The term "absence of targeting" is used herein to describe substantially no binding or accumulation of a ligand in all control tissues where an amount of ligand is detectable.

The terms "targeting ligand", "targeting molecule", "homing ligand", and "homing molecule" as used herein each refer to a ligand that displays targeting activity. In some embodiments, a targeting ligand displays selective targeting.

The term "binding" refers to an affinity between two molecules, for example, a ligand and a target molecule. As used herein, "binding" means a preferential binding of one molecule for another in a mixture of molecules. The binding of a ligand to a target molecule can be considered specific if the binding affinity is in some embodiments about $1 \times 10^4$ $M^{-1}$ to about $1 \times 10^6$ $M^{-1}$ or greater.

The phrase "specifically (or selectively) binds", when referring to the binding capacity of a ligand, refers to a binding reaction which is determinative of the presence of the protein in a heterogeneous population of proteins and other biological materials. The phrase "specifically binds" also refers to selectively targeting, as defined hereinabove.

The phases "substantially lack binding" or "substantially no binding", as used herein to describe binding of a ligand in a control tissue, refers to a level of binding that encompasses non-specific or background binding, but does not include specific binding.

The term "tumor" as used herein refers to both primary and metastasized solid tumors and carcinomas of any tissue in a subject, including but not limited to breast; colon; rectum; lung; oropharynx; hypopharynx; esophagus; stomach; pancreas; liver; gallbladder; bile ducts; small intestine; urinary tract including kidney, bladder and urothelium; female genital tract including cervix, uterus, ovaries (e.g., choriocarcinoma and gestational trophoblastic disease); male genital tract including prostate, seminal vesicles, testes and germ cell tumors; endocrine glands including thyroid, adrenal, and pituitary; skin (e.g., hemangiomas and melanomas), bone or soft tissues; blood vessels (e.g., Kaposi's sarcoma); brain, nerves, eyes, and meninges (e.g., astrocytomas, gliomas, glioblastomas, retinoblastomas, neuromas, neuroblastomas, Schwannomas and meningiomas). The term "tumor" also encompasses solid tumors arising from hematopoietic malignancies such as leukemias, including chloromas, plasmacytomas, plaques and tumors of mycosis fungoides and cutaneous T-cell lymphoma/leukemia, and lymphomas including both Hodgkin's and non-Hodgkin's lymphomas.

The term "subject" as used herein refers to any invertebrate or vertebrate species. The methods and compositions disclosed herein are particularly useful in the treatment and diagnosis of warm-blooded vertebrates. Thus, the presently disclosed subject matter concerns mammals and birds. More particularly contemplated is the treatment and/or diagnosis of mammals such as humans, as well as those mammals of importance due to being endangered (such as Siberian tigers), of economic importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also contemplated is the treatment of birds, including the treatment of those kinds of birds that are endangered, kept in zoos, as well as fowl, and more particularly domesticated fowl, e.g., poultry, such as turkeys, chickens, ducks, geese, guinea fowl, and the like, as they are also of economic importance to humans. Thus, contemplated is the treatment of livestock, including, but not limited to, domesticated swine (pigs and hogs), ruminants, horses, poultry, and the like.

The term "about", as used herein when referring to a measurable value such as an amount of weight, time, dose (e.g. radiation dose), etc. is meant to encompass variations of in some embodiments ±20%, in some embodiments ±10%, in some embodiments ±5%, in some embodiments ±1%, and in some embodiments ±0.1% from the specified amount, as such variations are appropriate to perform the disclosed method.

II. X-Ray Guided Drug Delivery Using Peptide Ligands

Ionizing radiation induces proteins in tumor vascular endothelium through transcriptional induction and/or post-translational modification of cell adhesion molecules such as integrins (Hallahan et al., 1995a; Hallahan et al., 1996; Hallahan et al., 1998; Hallahan & Virudachalam, 1999). For example, radiation induces activation of the integrin $\alpha_{2b}\beta_3$, also called the fibrinogen receptor, on platelets. The induced molecules can serve as binding sites for targeting ligands.

Although several radiation-induced molecules within tumor blood vessels have been identified and characterized, the $\alpha_{2b}\beta_3$ target for drug delivery achieves the greatest site-specific peptide binding within irradiated tumor blood vessels. $^{131}$I-labeled fibrinogen binds specifically to tumors following exposure to ionizing radiation (U.S. Pat. No. 6,159, 443). Peptides within fibrinogen that bind to the radiation-induced $\alpha_{2b}\beta_3$ receptor include HHLGGAKQAGDV (SEQ ID NO: 16) and the RGD peptide (Hallahan et al., 2001a).

The presently disclosed subject matter includes a study of the targeting activity of $\alpha_{2b}\beta_3$ ligands in tumor-bearing subjects. Example 1 describes x-ray-guided drug delivery in animal models using ligand-conjugated liposomes and microspheres. Clinical trials using a radiolabeled $\alpha_{2b}\beta_3$ ligand support the feasibility of x-ray-guided drug delivery in humans, as described in Example 2. See also Hallahan et al., 2001a.

Despite the successes of x-ray-guided drug delivery using $\alpha_{2b}\beta_3$ ligands in experimental models, the clinical application of this approach is limited by nonspecific binding of the targeting ligand at sites other than the tumor (Hallahan et al., 2001b). In addition, previous observations of radiation-inducible molecules have employed radiation doses that are sufficient to limit blood flow, as described in Example 3. Thus, ligands are sought that demonstrate improved tumor specificity and binding to target molecules induced by reduced radiation doses.

III. Identification of Ligands that Bind Irradiated Tumors

Approaches for optimizing peptide binding affinity and specificity have included modification of peptide conformation and addition of flanking amino acids to extend the minimal binding motif. For example, amino acids C-terminal to the RGD sequence are differentially conserved in RGD-containing ligands, and this variation correlates with differences in binding specificity (Cheng et al., 1994; Koivunen et al., 1994). Similarly, cyclization of a prototype RGD peptide to restrict its conformational flexibility improved interaction of the peptide with the vitronectin receptor, yet nearly abolished interaction with the fibronectin receptor (Pierschbacher & Ruoslahti, 1987).

Despite conservation of binding motifs among ligands that bind irradiated tumors and recognition of factors that can influence ligand binding, design of peptide sequences for improved targeting activity is yet unpredictable. Approaches for identifying such peptides have therefore relied on high volume screening methods to select effective motifs from peptide libraries (Koivunen et al., 1993; Healy et al., 1995). However, the utility of in vitro-selected peptides is unpredictable in so far as peptide binding properties are not consistently recapitulated in vivo. To obviate these challenges, the presently disclosed subject matter provides a method for in vivo selection of targeting ligands, described further hereinbelow.

Using the in vivo selection method disclosed herein, novel targeting ligands were identified that can be used for x-ray-guided drug delivery. Representative peptide ligands are set forth as SEQ ID NOs: 1-13 and 21-55. Representative antibody ligands are set forth as SEQ ID NOs: 18 and 20. The novel ligands display improved specificity of binding to irradiated tumors and are effective for targeting using low dose irradiation. The disclosed targeting ligands also offer benefits including moderate cost of preparation and ease of handling.

III. A. Libraries

As used herein, the term "library" means a collection of molecules. A library can contain a few or a large number of different molecules, varying from about ten molecules to several billion molecules or more. A molecule can comprise a naturally occurring molecule, or a synthetic molecule (i.e., a molecule that is not found in nature). Optionally, as described further hereinbelow, a plurality of different libraries can be employed simultaneously for in vivo panning.

Representative libraries include but are not limited to a peptide library (U.S. Pat. Nos. 6,156,511, 6,107,059, 5,922,545, and 5,223,409), an oligomer library (U.S. Pat. Nos. 5,650,489 and 5,858,670), an aptamer library (U.S. Pat. Nos. 6,180,348 and 5,756,291), a small molecule library (U.S. Pat. Nos. 6,168,912 and 5,738,996), a library of antibodies or antibody fragments (U.S. Pat. Nos. 6,174,708, 6,057,098, 5,922,254, 5,840,479, 5,780,225, 5,702,892, and 5,667,988), a library of nucleic acid-protein fusions (U.S. Pat. No. 6,214,553), and a library of any other affinity agent that can potentially bind to an irradiated tumor (e.g., U.S. Pat. Nos. 5,948,635, 5,747,334, and 5,498,538).

The molecules of a library can be produced in vitro, or they can be synthesized in vivo, for example by expression of a molecule in vivo. Also, the molecules of a library can be displayed on any relevant support, for example, on bacterial pili (Lu et al., 1995) or on phage (Smith, 1985).

A library can comprise a random collection of molecules. Alternatively, a library can comprise a collection of molecules having a bias for a particular sequence, structure, or conformation. See e.g., U.S. Pat. Nos. 5,264,563 and 5,824,483. Methods for preparing libraries containing diverse populations of various types of molecules are known in the art, for example as described in U.S. Patents cited hereinabove. Numerous libraries are also commercially available.

A library useful for in vivo panning as disclosed herein can comprise in some embodiments a library of ten or more diverse molecules, in some embodiments a library of one hundred or more diverse molecules, and in some embodiments a library of one billion or more diverse molecules. Representative diverse molecules include peptides, peptide mimetics, proteins, antibodies or fragments thereof, small molecules, nucleic acids, and combinations thereof. In some embodiments, a library of peptides, antibodies, or a combination thereof is used for in vivo panning. A library can further comprise a library of diverse molecules that is recovered following in vitro panning.

In some embodiments of the presently disclosed subject matter, a peptide library can be used to perform the disclosed in vivo panning methods. A peptide library comprises peptides comprising in some embodiments three or more amino acids, in some embodiments at least five, six, seven, or eight amino acids, in some embodiments up to 50 amino acids or 100 amino acids, and in some embodiments up to about 200 to 300 amino acids.

The peptides can be linear, branched, or cyclic, and can include nonpeptidyl moieties. The peptides can comprise naturally occurring amino acids, synthetic amino acids, genetically encoded amino acids, non-genetically encoded amino acids, and combinations thereof.

A biased peptide library can also be used, a biased library comprising peptides wherein one or more (but not all) residues of the peptides are constant. For example, an internal residue can be constant, so that the peptide sequence is represented as:

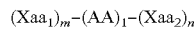

$(Xaa_1)_m-(AA)_1-(Xaa_2)_n$ where $Xaa_1$, and $Xaa_2$ are any amino acid, or any amino acid except cysteine, wherein $Xaa_1$, and $Xaa_2$ are the same or different amino acids, m and n indicate a number Xaa residues, wherein in some embodiments m and n are independently chosen from the range of 2 residues to 20 residues, in some embodiments m and n are chosen from the range of 4 residues to 9 residues, and AA is the same amino acid for all peptides in the library. In some embodiments, AA is located at or near the center of the peptide. More specifically, in some embodiments m and n are not different by more than 2 residues; in some embodiments m and n are equal.

In some embodiments, AA is tryptophan, proline, or tyrosine. In some embodiments, AA is phenylalanine, histidine, arginine, aspartate, leucine, or isoleucine. In some embodiments, AA is asparagine, serine, alanine, or methionine. In some embodiments, AA is cysteine or glycine.

A biased library used for in vivo panning also includes a library comprising molecules previously selected by in vitro panning methods. See Example 8.

In some embodiments of the presently disclosed subject matter, the method for in vivo panning is performed using a phage peptide library. Phage display is a method to discover peptide ligands while minimizing and optimizing the structure and function of proteins. Phage are used as a scaffold to display recombinant libraries of peptides and provide a means to recover and amplify the peptides that bind to putative receptor molecules in vivo. In vivo phage selection simultaneously provides positive and subtractive screens based on the spatial separation of normal tissues and tumors. Phage that specifically bind the vasculature of normal tissues are removed while specific phage that bind target molecules present in irradiated tumors are enriched through serial rounds of biopanning.

The T7 phage has an icosahedral capsid made of 415 proteins encoded by gene 10 during its lytic phase. The T7 phage display system has the capacity to display peptides up to 15 amino acids in size at a high copy number (415 per phage). Unlike filamentous phage display systems, peptides displayed on the surface of T7 phage are not capable of peptide secretion. T7 phage also replicate more rapidly and are extremely robust when compared to other phage. The stability allows for biopanning selection procedures that require persistent phage infectivity. Accordingly, the use of T7-based phage display is an aspect of a preferred embodiment of the presently disclosed subject matter. Example 4 describes a representative method for preparation of a T7 phage peptide library that can be used to perform the in vivo panning methods disclosed herein.

A phage peptide library to be used in accordance with the panning methods of the presently disclosed subject matter can also be constructed in a filamentous phage, for example M13 or M13-derived phage. In some embodiments, the encoded antibodies are displayed at the exterior surface of the phage, for example by fusion to M13 vital protein 8. Methods for preparing M13 libraries can be found in Sambrook & Russell, 2001, among other places.

In some embodiments, the method for in vivo panning is performed using a phage antibody library, as described in Example 8. Such a library can be constructed, for example, in M13 or M13-derived phage. See e.g., U.S. Pat. Nos. 6,225,447; 5,580,717; 5,702,892.

III. B. In Vivo Panning for Ligands that Bind Irradiated Tumors

The presently disclosed subject matter provides a method for in vivo panning for ligands that bind irradiated tumors. As used herein, the term "in vivo panning" refers to a method of screening a library for selection of a ligand that homes to an irradiated tumor.

The term "in vivo", as used herein to describe methods of panning or ligand selection, refers to contacting of one or more ligands to endogenous candidate target molecules, wherein the candidate target molecules are naturally present in a subject or a tumor biopsy from a subject, and the contacting occurs in the subject or in the biopsied tumor. By contrast, "in vitro" panning refers to contacting a library of candidate ligands with one or more isolated or recombinantly produced target molecules.

Thus, in some embodiments a method for in vivo panning as disclosed herein includes the steps of (a) exposing a tumor to ionizing radiation; (b) administering to a subject a library of diverse molecules; (c) procuring the tumor or fraction thereof; and (d) isolating one or more molecules of the library of diverse molecules from the tumor, whereby a molecule that binds an irradiated tumor is identified. When performing the presently disclosed in vivo panning methods, each of the steps of exposing, administering, procuring, and isolating can be repeated one or more times to modify and preferably improve ligand selection.

The term "administering to a subject", when used to describe provision of a library of molecules, is used in its broadest sense to mean that the library is delivered to the irradiated tumor. For example, a library can be provided to the circulation of the subject by injection or cannulization such that the molecules can pass through the tumor.

The in vivo panning methods of the presently disclosed subject matter can further comprise administering the library to isolated tumor cells or to isolated proteins prior to administering the library to a subject or to a tumor. For example, in vitro panning methods can be performed to select ligands that bind to particular tumor neoantigens, followed by performance of the in vivo panning methods as disclosed herein.

Thus, in some embodiments a library can be administered to an isolated tumor or tumor biopsy. Thus, in some embodiments a method for in vivo panning can also comprise: (a) exposing a tumor and a control tissue to ionizing radiation; (b) administering to the tumor and to the control tissue a library of diverse molecules; (c) detecting one or more molecules of the library that bind to the tumor and that substantially lack binding to the control tissue, whereby a molecule that binds an irradiated tumor is identified. In some embodiments, the methods can further comprise (a) isolating the tumor and the control tissue, and (b) administering the library to the tumor and to the control tissue in vitro.

The in vivo panning methods of the presently disclosed subject matter can further comprise administering the library to isolated tumor cells or to isolated proteins prior to administering the library to a subject or to a tumor. For example, in vitro panning methods can be performed to select ligands that bind to particular tumor neoantigens, followed by performance of the in vivo panning methods as disclosed herein.

In some embodiments of the presently disclosed subject matter, the radiation treatment comprises administration of less than about 2 Gy ionizing radiation. In some embodiments, the radiation treatment comprises at least about 2 Gy ionizing radiation, in some embodiments about 2 Gy to about 3 Gy ionizing radiation, and in some embodiments about 2 Gy to about 6 Gy ionizing radiation. In some embodiments, radiation treatment comprises about 10 Gy to about 20 Gy ionizing radiation.

The methods of the presently disclosed subject matter can be performed using any tumor-bearing subject or any subject suspected of having a tumor. In some embodiments, a subject is a warm-blooded vertebrate, in some embodiments a mammal, and in some embodiments a human.

In some embodiments of the presently disclosed subject matter, a library is administered to a tumor-bearing human subject following irradiation of the tumor. Methods and appropriate doses for administration of a library to a human subject are described in PCT International Publication No. WO 01/09611.

Example 5 describes a representative procedure for in vivo panning of phage-displayed peptide ligands that bind to irradiated tumor vessels in accordance with the presently disclosed subject matter. Briefly, peptide binding was studied in tumor blood vessels of 2 distinct tumor models: (1) GL261 glioma, and (2) Lewis lung carcinoma. Tumors were irradiated with 3 Gy to facilitate identification of peptide sequences that bind tumors exposed to a minimal dose of ionizing radiation. Phage were administered by tail vein injection into tumor bearing mice following irradiation. Phage were recovered from the tumor thereafter. Following multiple rounds of sequential in vivo binding to irradiated tumors, phage were recovered and individual phage were randomly picked and sequenced. Recovered phage were additionally tested for targeting activity in an animal model of melanoma, as described in Example 6.

Example 8 describes a representative procedure for in vivo panning of phage-displayed ligands comprising single chain antibodies. The library used for in vivo panning was a biased library in that a pool of antibody ligands that bind to radiation-induced antigens were pre-selected in vitro.

III. C. In Vitro Panning for Nuclear Targeting Ligands

Example 11 describes a representative procedure for in vitro panning of phage-displayed peptide ligands that can be used to target therapeutic and/or diagnostic compositions to the nucleus of tumor cells. After in vitro panning, the ability of identified peptides to target tumor cells in vivo are confirmed using the in vivo panning techniques disclosed herein.

III. D. Recovery of Targeting Ligands

Methods for identifying targeting ligands that bind an irradiated tumor are selected based on one or more characteristics common to the molecules present in the library. For example, mass spectrometry and/or gas chromatography can be used to resolve molecules that home to an irradiated tumor. Thus, where a library comprises diverse molecules based generally on the structure of an organic molecule, determining the presence of a parent peak for the particular molecule can identify a ligand that binds a radiation-induced target molecule.

If desired, a molecule can be linked to a tag, which can facilitate recovery or identification of the molecule. A representative tag is an oligonucleotide or a small molecule such as biotin. See e.g., Brenner & Lerner, 1992 and U.S. Pat. No. 6,068,829. In addition, a tag can be a support or surface to which a molecule can be attached. For example, a support can be a biological tag such as a virus or virus-like particle such as a bacteriophage ("phage"); a bacterium; or a eukaryotic cell such as yeast, an insect cell, or a mammalian cell (e.g., an endothelial progenitor cell or a leukocyte); or can be a physical tag such as a liposome or a microbead. In some embodiments, a support has a diameter less than about 10 µm to about 50 µm in its shortest dimension, such that the support can pass relatively unhindered through the capillary beds present in the subject and not occlude circulation. In addition, a support can be nontoxic and biodegradable, particularly where the subject used for in vivo panning is not sacrificed for isolation of library molecules from the tumor. Where a molecule is linked to a support, the part of the molecule suspected of being able to interact with a target in a cell in the subject is preferably positioned so as be able to participate in the interaction.

III. E. Peptide Ligands

A targeting peptide of the presently disclosed subject matter can be subject to various changes, substitutions, insertions, and deletions where such changes provide for certain advantages in its use. Thus, the term "peptide" encompasses any of a variety of forms of peptide derivatives, that include amides, conjugates with proteins, cyclized peptides, polymerized peptides, conservatively substituted variants, analogs, fragments, peptoids, chemically modified peptides, and peptide mimetics. The terms "targeting peptide" and "peptide ligand" refer to a peptide as defined hereinabove that binds to an irradiated tumor. An exemplary peptide ligand of the presently disclosed subject matter can bind to an irradiated tumor of in some embodiments at least one tumor type, in some embodiments two or more tumor types, and in some embodiments three or more tumor types. In some embodiments, a targeting ligand can bind to an irradiated glioma, melanoma, and/or a Lewis Lung carcinoma.

Peptides of the presently disclosed subject matter can comprise naturally occurring amino acids, synthetic amino acids, genetically encoded amino acids, non-genetically encoded amino acids, and combinations thereof. Peptides can include both L-form and D-form amino acids.

Representative non-genetically encoded amino acids include but are not limited to 2-aminoadipic acid; 3-aminoadipic acid; β-aminopropionic acid; 2-aminobutyric acid; 4-aminobutyric acid (piperidinic acid); 6-aminocaproic acid; 2-aminoheptanoic acid; 2-aminoisobutyric acid; 3-aminoisobutyric acid; 2-aminopimelic acid; 2,4-diaminobutyric acid; desmosine; 2,2'-diaminopimelic acid; 2,3-diaminopropionic acid; N-ethylglycine; N-ethylasparagine; hydroxylysine; allo-hydroxylysine; 3-hydroxyproline; 4-hydroxyproline; isodesmosine; allo-isoleucine; N-methylglycine (sarcosine); N-methylisoleucine; N-methylvaline; norvaline; norleucine; and ornithine.

Representative derivatized amino acids include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine.

The term "conservatively substituted variant" refers to a peptide comprising an amino acid residue sequence to a sequence of a reference ligand of radiation inducible target in which one or more residues have been conservatively substituted with a functionally similar residue and which displays the targeting activity as described herein. The phrase "conservatively substituted variant" also includes peptides wherein a residue is replaced with a chemically derivatized residue, provided that the resulting peptide displays targeting activity as disclosed herein.

Examples of conservative substitutions include the substitution of one non-polar (hydrophobic) residue such as isoleucine, valine, leucine or methionine for another; the substitution of one polar (hydrophilic) residue for another such as between arginine and lysine, between glutamine and asparagine, between glycine and serine; the substitution of one basic residue such as lysine, arginine or histidine for another; or the substitution of one acidic residue, such as aspartic acid or glutamic acid for another.

Peptides of the presently disclosed subject matter also include peptides comprising one or more additions and/or deletions or residues relative to the sequence of a peptide whose sequence is disclosed herein, so long as the requisite targeting activity of the peptide is maintained. The term "fragment" refers to a peptide comprising an amino acid residue sequence shorter than that of a peptide disclosed herein.

Additional residues can also be added at either terminus of a peptide for the purpose of providing a "linker" by which the peptides of the presently disclosed subject matter can be conveniently affixed to a label or solid matrix, or carrier. Amino acid residue linkers are usually at least one residue and can be 40 or more residues, more often 1 to 10 residues, but do alone not constitute radiation inducible target ligands. Typical amino acid residues used for linking are tyrosine, cysteine, lysine, glutamic and aspartic acid, or the like. In addition, a peptide can be modified by terminal-$NH_2$ acylation (e.g., acetylation, or thioglycolic acid amidation) or by terminal-carboxylamidation (e.g., with ammonia, methylamine, and the like terminal modifications). Terminal modifications are useful, as is well known, to reduce susceptibility by proteinase digestion, and therefore serve to prolong half life of the peptides in solutions, particularly biological fluids where proteases can be present.

Peptide cyclization is also a useful terminal modification, and is particularly preferred also because of the stable structures formed by cyclization and in view of the biological activities observed for such cyclic peptides as described herein. An exemplary method for cyclizing peptides is described by Schneider & Eberle, 1993. Typically, tertbutoxycarbonyl protected peptide methyl ester is dissolved in methanol and sodium hydroxide solution are added and the admixture is reacted at 20° C. to hydrolytically remove the methyl ester protecting group. After evaporating the solvent, the tertbutoxycarbonyl protected peptide is extracted with ethyl acetate from acidified aqueous solvent. The tertbutoxycarbonyl protecting group is then removed under mildly acidic conditions in dioxane cosolvent. The unprotected linear peptide with free amino and carboxyl termini so obtained is converted to its corresponding cyclic peptide by reacting a dilute solution of the linear peptide, in a mixture of dichloromethane and dimethylformamide, with dicyclohexylcarbodiimide in the presence of 1-hydroxybenzotriazole and N-methylmorpholine. The resultant cyclic peptide is then purified by chromatography.

The term "peptoid" as used herein refers to a peptide wherein one or more of the peptide bonds are replaced by pseudopeptide bonds including but not limited to a carba bond ($CH_2$—$CH_2$), a depsi bond (CO—O), a hydroxyethylene bond (CHOH—$CH_2$), a ketomethylene bond (CO—$CH_2$), a methylene-oxy bond ($CH_2$—O), a reduced bond ($CH_2$—NH), a thiomethylene bond ($CH_2$—S), a thiopeptide bond (CS—NH), and an N-modified bond (—NRCO—). See e.g. Corringer et al., 1993; Garbay-Jaureguiberry et al., 1992; Tung et al., 1992; Urge et al., 1992; Pavone et al., 1993.

Peptides of the presently disclosed subject matter, including peptoids, can be synthesized by any of the techniques that are known to those skilled in the art of peptide synthesis. Synthetic chemistry techniques, such as a solid-phase Merrifield-type synthesis, are preferred for reasons of purity, antigenic specificity, freedom from undesired side products, ease of production and the like. A summary of representative techniques can be found in Stewart & Young, 1969; Merrifield, 1969; Fields & Noble, 1990; and Bodanszky, 1993. Solid phase synthesis techniques can be found in Andersson et al., 2000, references cited therein, and in U.S. Pat. Nos. 6,015,561, 6,015,881, 6,031,071, and 4,244,946. Peptide synthesis in solution is described by Schröder & Lütke, 1965. Appropriate protective groups usable in such synthesis are described in the above texts and in McOmie, 1973. Peptides that include naturally occurring amino acids can also be produced using recombinant DNA technology. In addition, peptides comprising a specified amino acid sequence can be purchased from commercial sources (e.g., Biopeptide Co., LLC of San Diego, Calif., United States of America, and PeptidoGenics of Livermore, Calif., United States of America).

The term "peptide mimetic" as used herein refers to a ligand that mimics the biological activity of a reference peptide, by substantially duplicating the targeting activity of the reference peptide, but it is not a peptide or peptoid. In some embodiments, a peptide mimetic has a molecular weight of less than about 700 daltons.

In some embodiments, a peptide mimetic can be designed by (a) identifying the pharmacophoric groups responsible for the targeting activity of a peptide; (b) determining the spatial arrangements of the pharmacophoric groups in the active conformation of the peptide; and (c) selecting a pharmaceutically acceptable template upon which to mount the pharmacophoric groups in a manner that allows them to retain their spatial arrangement in the active conformation of the peptide. For identification of pharmacophoric groups responsible for targeting activity, mutant variants of the peptide can be prepared and assayed for targeting activity.

Alternatively or in addition, the three-dimensional structure of a complex of the peptide and its target molecule can be examined for evidence of interactions, for example the fit of a peptide side chain into a cleft of the target molecule, potential sites for hydrogen bonding, etc. The spatial arrangements of the pharmacophoric groups can be determined by NMR spectroscopy or X-ray diffraction studies. An initial three-dimensional model can be refined by energy minimization and molecular dynamics simulation. A template for modeling can be selected by reference to a template database and will typically allow the mounting of 2-8 pharmacophores. A peptide mimetic is identified wherein addition of the pharmacophoric groups to the template maintains their spatial arrangement as in the peptide.

A peptide mimetic can also be identified by assigning a hashed bitmap structural fingerprint to the peptide based on its chemical structure, and determining the similarity of that fingerprint to that of each compound in a broad chemical database. The fingerprints can be determined using fingerprinting software commercially distributed for that purpose by Daylight Chemical Information Systems, Inc. (Mission Viejo, Calif., United States of America) according to the vendor's instructions. Representative databases include but are not limited to SPREI'95 (InfoChem GmbH of München, Germany), Index Chemicus (ISI of Philadelphia, Pa., United States of America), World Drug Index (Derwent of London, United Kingdom), TSCA93 (United States Envrionmental Protection Agency), MedChem (Biobyte of Claremont, Calif., United States of America), Maybridge Organic Chemical Catalog (Maybridge of Cornwall, United Kingdom), Available Chemicals Directory (MDL Information Systems of San Leandro, Calif., United States of America), NCI96 (United States National Cancer Institute), Asinex Catalog of Organic Compounds (Asinex Ltd. of Moscow, Russia), and NP (InterBioScreen Ltd. of Moscow, Russia). A peptide mimetic of a reference peptide is selected as comprising a fingerprint with a similarity (Tanamoto coefficient) of at least 0.85 relative to the fingerprint of the reference peptide. Such peptide mimetics can be tested for bonding to an irradiated tumor using the methods disclosed herein.

Additional techniques for the design and preparation of peptide mimetics can be found in U.S. Pat. Nos. 5,811,392; 5,811,512; 5,578,629; 5,817,879; 5,817,757; and 5,811,515.

Any peptide or peptide mimetic of the presently disclosed subject matter can be used in the form of a pharmaceutically acceptable salt. Suitable acids which are capable of the peptides with the peptides of the presently disclosed subject matter include inorganic acids such as trifluoroacetic acid (TFA), hydrochloric acid (HCl), hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like. HCl and TFA salts are particularly preferred.

Suitable bases capable of forming salts with the peptides of the presently disclosed subject matter include inorganic bases such as sodium hydroxide, ammonium hydroxide, potassium hydroxide and the like; and organic bases such as mono-di- and tri-alkyl and aryl amines (e.g. triethylamine, diisopropyl amine, methyl amine, dimethyl amine and the like), and optionally substituted ethanolamines (e.g. ethanolamine, diethanolamine and the like).

III. F. Antibody Ligands

A targeting antibody of the presently disclosed subject matter comprises an antibody identified by the in vivo panning methods disclosed herein. In some embodiments, an antibody targeting ligand comprises (a) a polypeptide comprising an amino acid sequence of SEQ ID NO: 18 or 20; (b) a polypeptide substantially identical to SEQ ID NO: 18 or 20; (c) a polypeptide encoded by SEQ ID NO: 17 or 19; or (d) a polypeptide substantially identical to SEQ ID NO: 17 or 19. Thus, the presently disclosed subject matter also provides in some embodiments an isolated nucleic acid that encodes an antibody targeting ligand comprising (a) a nucleic acid molecule comprising the nucleotide sequence of SEQ ID NO: 17 or 19; or (b) a nucleic acid molecule substantially identical to SEQ ID NO: 17 or 19.

The term "isolated", as used in the context of a nucleic acid or polypeptide, indicates that the nucleic acid or polypeptide exists apart from its native environment and is not a product of nature. An isolated nucleic acid or polypeptide can exist in a purified form or can exist in a non-native environment such as a transgenic host cell.

Nucleic Acids Encoding Targeting Antibodies.

The terms "nucleic acid molecule" or "nucleic acid" each refer to deoxyribonucleotides or ribonucleotides and polymers thereof in single-stranded or double-stranded. Unless specifically limited, the term encompasses nucleic acids containing known analogues of natural nucleotides that have similar properties as the reference natural nucleic acid. The terms "nucleic acid molecule" or "nucleic acid" can also be used in place of "gene", "cDNA", or "mRNA". Nucleic acids can be synthesized, or can be derived from any biological source, including any organism.

The term "substantially identical", as used herein to describe a degree of similarity between nucleotide sequences, refers to two or more sequences that have in some embodiments at least about least 60%, in some embodiments at least about least 65%, in some embodiments at least about 70%, in some embodiments at least about least 75%, in some embodiments at least about 80%, in some embodiments at least about least 85%, in some embodiments at least about 90%, in some embodiments at least about least 93%, in some embodiments at least about least 95%, in some embodiments at least about least 97%, and in some embodiments about 99% nucleotide identity, as measured using one of the following sequence comparison algorithms (described hereinbelow) or by visual inspection. The substantial identity exists in nucleotide sequences of in some embodiments at least about 100 residues, in some embodiments at least about 150 residues, and in some embodiments in nucleotide sequences comprising a full length coding sequence.

Thus, substantially identical sequences can comprise mutagenized sequences, including sequences comprising silent mutations, or variably synthesized sequences. A mutation or variant sequence can comprise a single base change.

Another indication that two nucleotide sequences are substantially identical is that the two molecules specifically or substantially hybridize to each other under stringent conditions. In the context of nucleic acid hybridization, two nucleic acid sequences being compared can be designated a "probe" and a "target". A "probe" is a reference nucleic acid molecule, and a "target" is a test nucleic acid molecule, often found within a heterogeneous population of nucleic acid molecules. A "target sequence" is synonymous with a "test sequence".

An exemplary nucleotide sequence that can be employed for hybridization studies or assays includes probe sequences that are complementary to or mimic at least an about 14 to 40 nucleotide sequence of a nucleic acid molecule of the presently disclosed subject matter. For this purpose, a probe comprises a region of the nucleic acid molecule other than a sequence encoding a common immunoglobulin region. Thus, a probe comprises in some embodiments a sequence encoding a domain of the antibody that comprises an antigen-binding site. In some embodiments, probes comprise 14 to 20 nucleotides, or even longer where desired, such as 30, 40, 50, 60, 100, 200, 300 nucleotides or up to the full length of a region of SEQ ID NO: 17 or 19 that encodes an antigen binding site. Such fragments can be readily prepared by, for example, chemical synthesis of the fragment, by application of nucleic acid amplification technology, or by introducing selected sequences into recombinant vectors for recombinant production.

The phrase "hybridizing specifically to" refers to the binding, duplexing, or hybridizing of a molecule only to a particular nucleotide sequence under stringent conditions when that sequence is present in a complex nucleic acid mixture (e.g., total cellular DNA or RNA).

The phrase "hybridizing substantially to" refers to complementary hybridization between a probe nucleic acid molecule and a target nucleic acid molecule and embraces minor mismatches that can be accommodated by reducing the stringency of the hybridization media to achieve the desired hybridization.

"Stringent hybridization conditions" and "stringent hybridization wash conditions" in the context of nucleic acid hybridization experiments such as Southern and Northern blot analysis are both sequence- and environment-dependent. Longer sequences hybridize specifically at higher temperatures. An extensive guide to the hybridization of nucleic acids is found in Tijssen, 1993. Generally, highly stringent hybridization and wash conditions are selected to be about 5° C. lower than the thermal melting point ($T_m$) for the specific sequence at a defined ionic strength and pH. Typically, under "stringent conditions" a probe will hybridize specifically to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for Southern or Northern Blot analysis of complementary nucleic acids having more than about 100 complementary residues is overnight hybridization in 50% formamide with 1 mg of heparin at 42° C. An example of highly stringent wash conditions is 15 minutes in 0.1×SSC at 65° C. An example of stringent wash conditions is 15 minutes in 0.2×SSC buffer at 65° C. See Sambrook & Russell, 2001 for a description of SSC buffer.

Often, a high stringency wash is preceded by a low stringency wash to remove background probe signal. An example of medium stringency wash conditions for a duplex of more than about 100 nucleotides, is 15 minutes in 1×SSC at 45° C. An example of low stringency wash for a duplex of more than about 100 nucleotides, is 15 minutes in 4× to 6×SSC at 40° C. For short probes (e.g., about 10 to 50 nucleotides), stringent conditions typically involve salt concentrations of less than about 1M Na$^+$ ion, typically about 0.01 to 1M Na$^+$ ion concentration (or other salts) at pH 7.0-8.3, and the temperature is typically at least about 30° C. Stringent conditions can also be achieved with the addition of destabilizing agents such as formamide. In general, a signal to noise ratio of 2-fold (or higher) than that observed for an unrelated probe in the particular hybridization assay indicates detection of a specific hybridization.

The following are examples of hybridization and wash conditions that can be used to identify nucleotide sequences that are substantially identical to reference nucleotide sequences of the presently disclosed subject matter: in some embodiments a probe nucleotide sequence hybridizes to a target nucleotide sequence in 7% sodium dodecyl sulfate (SDS), 0.5 M NaPO$_4$, 1 mM EDTA at 50° C. followed by washing in 2×SSC, 0.1% SDS at 50° C.; in some embodiments a probe and target sequence hybridize in 7% sodium dodecyl sulfate (SDS), 0.5 M NaPO$_4$, 1 mM EDTA at 50° C. followed by washing in 1×SSC, 0.1% SDS at 50° C.; in some embodiments a probe and target sequence hybridize in 7% sodium dodecyl sulfate (SDS), 0.5 M NaPO$_4$, 1 mM EDTA at 50° C. followed by washing in 0.5×SSC, 0.1% SDS at 50° C.; in some embodiments a probe and target sequence hybridize in 7% sodium dodecyl sulfate (SDS), 0.5 M NaPO$_4$, 1 mM EDTA at 50° C. followed by washing in 0.1×SSC, 0.1% SDS at 50° C.; and in some embodiments a probe and target sequence hybridize in 7% sodium dodecyl sulfate (SDS), 0.5 M NaPO$_4$, 1 mM EDTA at 50° C. followed by washing in 0.1×SSC, 0.1% SDS at 65° C.

A further indication that two nucleic acid sequences are substantially identical is that proteins encoded by the nucleic acids are substantially identical, share an overall three-dimensional structure, or are biologically functional equivalents. These terms are defined further hereinbelow. Nucleic acid molecules that do not hybridize to each other under stringent conditions are still substantially identical if the corresponding proteins are substantially identical. This can occur, for example, when two nucleotide sequences are significantly degenerate as permitted by the genetic code.

The term "conservatively substituted variants" refers to nucleic acid sequences having degenerate codon substitutions wherein the third position of one or more selected (or all) codons is substituted with mixed-base and/or deoxyinosine residues. See Batzer et al., 1991; Ohtsuka et al., 1985; Rossolini et al., 1994.

The term "subsequence" refers to a sequence of nucleic acids that comprises a part of a longer nucleic acid sequence. An exemplary subsequence is a probe, described hereinabove, or a primer. The term "primer" as used herein refers to a contiguous sequence comprising in some embodiments about 8 or more deoxyribonucleotides or ribonucleotides, in some embodiments about 10-20 nucleotides, and in some embodiments about 20-30 nucleotides of a selected nucleic acid molecule. The primers of the presently disclosed subject matter encompass oligonucleotides of sufficient length and appropriate sequence so as to provide initiation of polymerization on a nucleic acid molecule of the presently disclosed subject matter.

The term "elongated sequence" refers to an addition of nucleotides (or other analogous molecules) incorporated into the nucleic acid. For example, a polymerase (e.g., a DNA polymerase) can add sequences at the 3' terminus of the nucleic acid molecule. In addition, the nucleotide sequence can be combined with other DNA sequences, such as promoters, promoter regions, enhancers, polyadenylation signals, intronic sequences, additional restriction enzyme sites, multiple cloning sites, and other coding segments.

Nucleic acids of the presently disclosed subject matter can be cloned, synthesized, recombinantly altered, mutagenized, or combinations thereof. Standard recombinant DNA and molecular cloning techniques used to isolate nucleic acids are known in the art. Site-specific mutagenesis to create base pair changes, deletions, or small insertions are also known in the art. See e.g., Sambrook & Russell, 2001; Silhavy et al., 1984; Glover & Hames, 1995; Ausubel, 1995.

Single Chain Antibody Polypeptides.

The term "substantially identical", as used herein to describe a level of similarity between a polypeptide comprising an antibody targeting ligand and a polypeptide to SCN1A, refers to a sequence having in some embodiments at least about 45%, in some embodiments at least about 50%, in some embodiments at least about 60%, in some embodiments at least about 70%, in some embodiments at least about 80%, in some embodiments at least about 90%, in some embodiments at least about 95%, and in some embodiments at least about 99% sequence identity to SEQ ID NO: 17 or 19, when compared over the full length of the single chain polypeptide. The term "full length", as used herein to describe an antibody targeting ligand, comprises an amino acid sequence having 254 amino acids. Methods for determining percent identity are defined hereinbelow.

Substantially identical polypeptides also encompass two or more polypeptides sharing a conserved three-dimensional structure. Computational methods can be used to compare structural representations, and structural models can be generated and easily tuned to identify similarities around important active sites or ligand binding sites. See Saqi et al., 1999; Barton, 1998; Henikoff et al., 2000; Huang et al., 2000.

Substantially identical proteins also include proteins comprising an amino acid sequence comprising amino acids that are functionally equivalent to amino acids of SEQ ID NOs: 18 and 20. The term "functionally equivalent" in the context of amino acid sequences is known in the art and is based on the relative similarity of the amino acid side-chain substituents. See Henikoff & Henikoff, 2000. Relevant factors for consideration include side-chain hydrophobicity, hydrophilicity, charge, and size. For example, arginine, lysine, and histidine are all positively charged residues; that alanine, glycine, and serine are all of similar size; and that phenylalanine, tryptophan, and tyrosine all have a generally similar shape. By this analysis, described further hereinbelow, arginine, lysine, and histidine; alanine, glycine, and serine; and phenylalanine, tryptophan, and tyrosine; are defined herein as biologically functional equivalents.

In making biologically functional equivalent amino acid substitutions, the hydropathic index of amino acids can be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte et al., 1982). It is known that certain amino acids can be substituted for other amino acids having a similar hydropathic index or score and still retain a similar biological activity. In making changes based upon the hydropathic index, amino acids can be substituted whose hydropathic indices are in some embodiments within ±2 of the original value, in some embodiments within ±1 of the original value, and in some embodiments within ±0.5 of the original value.

It is also understood in the art that the substitution of like amino acids can be made effectively on the basis of hydrophilicity. U.S. Pat. No. 4,554,101 describes that the greatest local average hydrophilicity of a protein, as governed by the hydrophilicity of its adjacent amino acids, correlates with its immunogenicity and antigenicity, e.g., with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, amino acids can be substituted whose hydrophilicity values are in some embodiments within ±2 of the original value, in some embodiments within ±1 of the original value, and in some embodiments within ±0.5 of the original value.

The term "substantially identical" also encompasses polypeptides that are biologically functional equivalents. The term "functional", as used herein to describe polypeptides comprising antibody targeting ligands, refers two or more antibodies that are immunoreactive with a same radiation-induced target molecule. In some embodiments, the two or more antibodies specifically bind a same target molecule and substantially lack binding to a control antigen.

The term "specifically binds", when used to describe binding of an antibody to a target molecule, refers to binding to a target molecule in a heterogeneous mixture of other polypeptides.

The phases "substantially lack binding" or "substantially no binding", as used herein to describe binding of an antibody to a control polypeptide or sample, refers to a level of binding that encompasses non-specific or background binding, but does not include specific binding.

Techniques for detecting antibody-target molecule complexes are known in the art and include but are not limited to centrifugation, affinity chromatography and other immunochemical methods. In some embodiments, an antibody-target molecule complex can be detected following administration of an antibody to a subject as described in Examples 6 and 7. In some embodiments, an antibody-target molecule complex can be detected in vivo by performing radiation-guided drug delivery, wherein the drug comprises a targeting antibody of SEQ ID NO: 18 or 20 and a detectable label, as described in Examples 1 and 2. See also, Manson, 1992; Ishikawa, 1999; Law, 1996.

The presently disclosed subject matter also provides functional fragments of an antibody targeting polypeptide. Such functional portion need not comprise all or substantially all of the amino acid sequence of SEQ ID NO: 18 or 20.

The presently disclosed subject matter also includes functional polypeptide sequences that are longer sequences than that of SEQ ID NO: 18 or 20. For example, one or more amino acids can be added to the N-terminus or C-terminus of a antibody targeting ligand. Methods of preparing such proteins are known in the art.

Isolated polypeptides and recombinantly produced polypeptides can be purified and characterized using a variety of standard techniques that are known to the skilled artisan. See e.g., Schröder & Lübke, 1965; Schneider & Eberle, 1993; Bodanszky, 1993; Ausubel, 1995.

Nucleotide and Amino Acid Sequence Comparisons.

The terms "identical" or percent "identity" in the context of two or more nucleotide or polypeptide sequences, refer to two or more sequences or subsequences that are the same or have a specified percentage of amino acid residues or nucleotides that are the same, when compared and aligned for maximum correspondence, as measured using one of the sequence comparison algorithms disclosed herein or by visual inspection.

The term "substantially identical" in regards to a nucleotide or polypeptide sequence means that a particular sequence varies from the sequence of a naturally occurring sequence by one or more deletions, substitutions, or additions, the net effect of which is to retain biological activity of a gene, gene product, or sequence of interest.

For sequence comparison, typically one sequence acts as a reference sequence to which test sequences are compared. When using a sequence comparison algorithm, test and reference sequences are entered into a computer program, subsequence coordinates are designated if necessary, and sequence algorithm program parameters are selected. The sequence comparison algorithm then calculates the percent sequence identity for the designated test sequence(s) relative to the reference sequence, based on the selected program parameters.

Optimal alignment of sequences for comparison can be conducted, for example, by the local homology algorithm of Smith & Waterman, 1981, by the homology alignment algorithm of Needleman & Wunsch, 1970, by the search for similarity method of Pearson & Lipman, 1988, by computerized implementations of these algorithms (e.g., programs available in the DISCOVERY STUDIO® package from Accelrys, Inc., San Diego, Calif., United States of America), or by visual inspection. See generally, Ausubel, 1995.

An exemplary algorithm for determining percent sequence identity and sequence similarity is the BLAST algorithm, which is described in Altschul et al., 1990. Software for performing BLAST analyses is publicly available through the website of the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength W=11, an expectation E=10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See Henikoff & Henikoff, 1992.

In addition to calculating percent sequence identity, the BLAST algorithm also performs a statistical analysis of the similarity between two sequences. See e.g., Karlin & Altschul, 1993. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is in some embodiments less than about 0.1, in some embodiments less than about 0.01, and in some embodiments less than about 0.001.

IV. Tumor Diagnosis, Treatment, and Imaging

The presently disclosed subject matter further provides in some embodiments methods and compositions for x-ray guided drug delivery to a tumor in a subject. The term "drug" as used herein refers to any substance having biological or detectable activity. Thus, the term "drug" includes a pharmaceutical agent, a diagnostic agent, or a combination thereof. The term "drug" also includes any substance that is desirably delivered to a tumor.

Thus, in some embodiments, a composition is prepared, the composition comprising a targeting ligand as disclosed herein and a diagnostic agent. In some embodiments, the composition can be used for the detection of a tumor in a subject by (a) exposing a suspected tumor to ionizing radiation; (b) administering to the subject a targeting ligand of the invention, wherein the ligand comprises a detectable label; and (c) detecting the detectable label, whereby a tumor is diagnosed. In some embodiments, a method for detecting a tumor can comprise (a) exposing a suspected tumor to ionizing radiation; (b) biopsing a suspected tumor; (c) contacting a targeting ligand of the invention with the suspected tumor in vitro, wherein the ligand comprises a detectable label; and (d) detecting the detectable label, whereby a tumor is diagnosed.

A therapeutic composition of the presently disclosed subject matter can comprise one or more targeting ligands and a therapeutic agent, such that the therapeutic agent can be selectively targeted to an irradiated tumor. Representative therapeutic agents include a radionuclide, a cytotoxin, a therapeutic gene, and a chemotherapeutic agent. The one or more targeting ligands can comprise ligands having diverse molecular features. For example, one or more targeting ligands can comprise both peptide and antibody targeting ligands.

In some embodiments, a therapeutic composition can additionally comprise a detectable label, in some embodiments a label that can be detected in vivo. The biodistribution of the therapeutic composition so prepared can be monitored following administration to a subject.

Methods for preparation, labeling, and x-ray guided drug delivery using targeting ligands of the presently disclosed subject matter are described further hereinbelow. See also Examples 1 and 2.

IV. A. Therapeutic Agents

The novel targeting ligands disclosed here are used to target a therapeutic agent to an irradiated tumor. Representative therapeutic agents include but are not limited to a nucleic acid (e.g., a therapeutic gene) and a small molecule. In some embodiments of the presently disclosed subject matter, an inactive drug is administered, which is subsequently activated by irradiation (Hallahan et al., 1995b). For example, therapeutic gene expression can be regulated by a radiation-inducible promoter (Hallahan et al., 1995b).

Therapeutic Genes.

Angiogenesis and suppressed immune response play a central role in the pathogenesis of malignant disease and tumor growth, invasion, and metastasis. Thus, in some embodiments, a therapeutic gene encodes a polypeptide having an ability to induce an immune response and/or an anti-angiogenic response in vivo.

The term "immune response" is meant to refer to any response to an antigen or antigenic determinant by the immune system of a vertebrate subject. Exemplary immune responses include humoral immune responses (e.g. production of antigen-specific antibodies) and cell-mediated immune responses (e.g. lymphocyte proliferation).

Representative therapeutic proteins with immunostimulatory effects include but are not limited to cytokines (e.g., IL-2, IL-4, IL-7, IL-12, interferons, granulocyte-macrophage colony-stimulating factor (GM-CSF), tumor necrosis factor alpha (TNF-α)), immunomodulatory cell surface proteins (e.g., human leukocyte antigen (HLA proteins), co-stimulatory molecules, and tumor-associated antigens. See Kirk & Mule, 2000; Mackensen et al., 1997; Walther & Stein, 1999; and references cited therein.

The term "angiogenesis" refers to the process by which new blood vessels are formed. The term "anti-angiogenic response" and "anti-angiogenic activity" as used herein, each refer to a biological process wherein the formation of new blood vessels is inhibited.

Representative proteins with anti-angiogenic activities that can be used in accordance with the presently disclosed subject matter include: thrombospondin I (Kosfeld & Frazier, 1993; Tolsma et al., 1993; Dameron et al., 1994), metallospondin proteins (Carpizo & Iruela-Arispe, 2000), class I interferons (Albini et al., 2000), ID 2 (Voest et al., 1995), protamine (Ingber et al., 1990), angiostatin (O'Reilly et al., 1994), laminin (Sakamoto et al., 1991), endostatin (O'Reilly et al., 1997), and a prolactin fragment (Clapp et al., 1993). In addition, several anti-angiogenic peptides have been isolated from these proteins (Maione et al., 1990; Eijan et al., 1991; Woltering et al., 1991).

A gene therapy construct used in accordance with the methods of the presently disclosed subject matter can also encode a therapeutic gene that displays both immunostimulatory and anti-angiogenic activities, for example, IL-12 (see Dias et al., 1998; and references cited hereinbelow), interferon-α (O'Byrne et al., 2000, and references cited therein), or a chemokine (Nomura & Hasegawa, 2000, and references cited therein). In addition, a gene therapy construct can encode a gene product with immunostimulatory activity and a gene product having anti-angiogenic activity. See e.g. Narvaiza et al., 2000.

Additional compositions useful for cancer therapy include but are not limited to genes encoding tumor suppressor gene products/antigens, apoptosis-inducing polypeptides, antimetabolites, suicide gene products, and combinations thereof. See Kirk & Mule, 2000; Mackensen et al., 1997; Walther & Stein, 1999; and references cited therein.

Therapeutic Compounds.

In accordance with the methods of the presently disclosed subject matter, a therapeutic agent can also comprise a cytotoxic agent, a chemotherapeutic agent, a radionuclide, or any other anti-tumor molecule. Studies using ligand/drug conjugates have demonstrated that a chemotherapeutic agent can be linked to a ligand to produce a conjugate that maintains the binding specificity of the ligand and the therapeutic function of the agent. For example, doxorubicin has been linked to antibodies or peptides and the ligand/doxorubicin conjugates display cytotoxic activity (Shih et al., 1994; Lau et al., 1995; Sivam et al., 1995), PCT International Publication No. WO 98/10795). Similarly, other anthracyclines, including idarubicin and daunorubocin, have been chemically conjugated to antibodies, which have facilitated delivery of effective doses of the agents to tumors (Aboud-Pirak et al., 1989; Rowland et al., 1993). Other chemotherapeutic agents include cis-platinum (Schechter et al., 1991), methotrexate (Shawler et al., 1988; Fitzpatrick & Garnett, 1995) and mitomycin-C (Dillman et al., 1989).

In some embodiments of the presently disclosed subject matter, a therapeutic agent comprises a radionuclide. Radionuclides can be effectively conjugated to antibodies (Hartmann et al., 1994; Buchsbaum et al., 1995), small molecule ligands (Wilbur, 1992; Fjalling et al., 1996), and peptides (Boerman et al., 2000; Krenning & de Jong, 2000; Kwekkeboom et al., 2000; Virgolini et al., 2001, and references cited therein), such that administration of the conjugated radionuclide promotes tumor regression. Representative therapeutic radionuclides and methods for preparing a radionuclide-labeled agent are described further hereinbelow under the heading *Scinitgraphic Imaging*. For therapeutic methods of the presently disclosed subject matter, a preferred radionuclide comprises $^{131}$I.

Additional anti-tumor agents that can be conjugated to the targeting ligands disclosed herein and used in accordance with the therapeutic methods of the presently disclosed subject matter include but are not limited to alkylating agents such as melphalan and chlorambucil (Smyth et al., 1987; Aboud-Pirak et al., 1989; Rowland et al., 1993), vinca alkaloids such as vindesine and vinblastine (Aboud-Pirak et al., 1989; Starling et al., 1992), antimetabolites such as 5-fluorouracil, 5-fluorouridine and derivatives thereof (Krauer et al., 1992; Henn et al., 1993).

Nuclear Targeting.

In some embodiments, the therapeutic and/or diagnostic compositions of disclosed herein are targeted to the nucleus of a cell (e.g., the nucleus of a tumor cell). Targeting to the cell nucleus can be accomplished using targeting peptides comprising, in some embodiments, any of SEQ ID NOs: 47-55. In some embodiments, the targeting is to the nucleus of a tumor cell. Targeting to the nucleus of a tumor cell can be accomplished using a targeting ligand that comprises, in some embodiments, a peptide comprising any of SEQ ID NOs: 47-55. Targeting to the nucleus of a tumor cell can be accomplished using a targeting ligand that comprises, in some embodiments, a peptide comprising any of SEQ ID NOs: 47-55 in addition to a tumor-targeting peptide as disclosed herein (e.g., SEQ ID NOs: 1-13 and 20-46).

The therapeutic and/or diagnostic compositions that are targeted to the nucleus can comprise any of the therapeutic and/or diagnostic entities disclosed herein, including therapeutic agents and diagnostic agents disclosed herein. In some embodiments the nuclear targeting composition can be used to deliver additional therapeutic and diagnostic agents that are therapeutically effective when delivered to the nucleus. Such agents include, but are not limited to polypeptides associated with apoptosis induction, as well as the nucleotide sequences encoding such polypeptides. Exemplary apoptosis-inducing genes and gene products include, but are not limited to bax, bak, and DP5.

IV. B. Preparation of a Therapeutic and/or Diagnostic Composition

The presently disclosed subject matter also provides a method for preparing a composition for x-ray-guided drug delivery. In some embodiments, the method comprises (a) performing in vivo panning, whereby a ligand that binds a radiation-inducible tumor molecule is identified; and (b) conjugating the ligand to a drug, whereby a composition for x-ray-guided drug delivery is prepared. A drug can further comprise a drug carrier and can be formulated in any manner suitable for administration to a subject. In some embodiments, the method employs a targeting ligand comprising any one of SEQ ID NOs: 1-13, 18, and 20-55.

Drug Carriers.

The compositions of the presently disclosed subject matter can further comprise a drug carrier to facilitate drug preparation and administration. Any suitable drug delivery vehicle or carrier can be used, including but not limited to a gene therapy vector (e.g., a viral vector or a plasmid), a microcapsule, for example a microsphere or a nanosphere (Manome et al., 1994; Hallahan, 2001a; Saltzman & Fung, 1997), a peptide (U.S. Pat. Nos. 6,127,339 and 5,574,172), a glycosaminoglycan (U.S. Pat. No. 6,106,866), a fatty acid (U.S. Pat. No. 5,994,392), a fatty emulsion (U.S. Pat. No. 5,651,991), a lipid or lipid derivative (U.S. Pat. No. 5,786,387), collagen (U.S. Pat. No. 5,922,356), a polysaccharide or derivative thereof (U.S. Pat. No. 5,688,931), a nanosuspension (U.S. Pat. No. 5,858,410), a polymeric micelle or conjugate (Goldman et al., 1997 and U.S. Pat. Nos. 4,551,482, 5,714,166, 5,510,103, 5,490,840, and 5,855,900), and a polysome (U.S. Pat. No. 5,922,545).

Conjugation of Targeting Ligands.

Antibodies, peptides, or other ligands can be coupled to drugs or drug carriers using methods known in the art, including but not limited to carbodiimide conjugation, esterification, sodium periodate oxidation followed by reductive alkylation, and glutaraldehyde crosslinking. See Goldman et al., 1997; Cheng, 1996; Neri et al., 1997; Nabel, 1997; Park et al., 1997; Pasqualini et al., 1997; Bauminger & Wilchek, 1980; U.S. Pat. No. 6,071,890; and European Patent No. 0 439 095.

In addition, a targeting peptide or antibody can be recombinantly expressed. For example, a nucleotide sequence encoding a targeting peptide or ligand can be cloned into adenovirus DNA encoding the H1 loop fiber, such that the targeting peptide or ligand is extracellularly presented. An adenovirus vector so prepared can be used for x-ray-guided delivery of a gene therapy construct as disclosed herein. A modified adenovirus vector encoding the RGD peptide was observed to transduce the endothelium in tumor blood vessels.

Formulation.

A therapeutic composition, a diagnostic composition, or a combination thereof, of the presently disclosed subject matter comprises in some embodiments a pharmaceutical composition that includes a pharmaceutically acceptable carrier. Suitable formulations include aqueous and non-aqueous sterile injection solutions which can contain anti-oxidants, buffers, bacteriostats, bactericidal antibiotics and solutes which render the formulation isotonic with the bodily fluids of the intended recipient; and aqueous and non-aqueous sterile suspensions which can include suspending agents and thickening agents. The formulations can be presented in unit-dose or multi-dose containers, for example sealed ampoules and vials, and can be stored in a frozen or freeze-dried (lyophilized) condition requiring only the addition of sterile liquid carrier, for example water for injections, immediately prior to use. Some exemplary ingredients are SDS in the range of in some embodiments 0.1 to 10 mg/ml, in some embodiments about 2.0 mg/ml; and/or mannitol or another sugar in the range of in some embodiments 10 to 100 mg/ml, in some embodiments about 30 mg/ml; and/or phosphate-buffered saline (PBS). Any other agents conventional in the art having regard to the type of formulation in question can be used.

The therapeutic regimens and pharmaceutical compositions of the invention can be used with additional adjuvants or biological response modifiers including, but not limited to, the cytokines IFN-α, IFN-γ, IL-2, IL-4, IL-6, TNF, or other cytokine affecting immune cells.

IV. C. Administration

Suitable methods for administration of a therapeutic composition, a diagnostic composition, or combination thereof, of the presently disclosed subject matter include but are not limited to intravascular, subcutaneous, or intratumoral administration. In some embodiments, intravascular administration is employed. For delivery of compositions to pulmonary pathways, compositions can be administered as an aerosol or coarse spray.

For therapeutic applications, a therapeutically effective amount of a composition of the presently disclosed subject matter is administered to a subject. A "therapeutically effective amount" is an amount of the therapeutic composition sufficient to produce a measurable biological tumor response (e.g., an immunostimulatory, an anti-angiogenic response, a cytotoxic response, or tumor regression). Actual dosage levels of active ingredients in a therapeutic composition of the invention can be varied so as to administer an amount of the active compound(s) that is effective to achieve the desired therapeutic response for a particular subject. The selected dosage level will depend upon a variety of factors including the activity of the therapeutic composition, formulation, the route of administration, combination with other drugs or treatments, tumor size and longevity, and the physical condition and prior medical history of the subject being treated. In some embodiments of the presently disclosed subject matter, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine.

For diagnostic applications, a detectable amount of a composition of the invention is administered to a subject. A "detectable amount", as used herein to refer to a diagnostic composition, refers to a dose of such a composition that the presence of the composition can be determined in vivo or in vitro. A detectable amount will vary according to a variety of factors, including but not limited to chemical features of the drug being labeled, the detectable label, labeling methods, the method of imaging and parameters related thereto, metabolism of the labeled drug in the subject, the stability of the label (e.g. the half-life of a radionuclide label), the time elapsed following administration of the drug and/or labeled antibody prior to imaging, the route of drug administration, the physical condition and prior medical history of the subject, and the size and longevity of the tumor or suspected tumor. Thus, a detectable amount can vary and can be tailored to a particular application. After study of the present disclosure, and in particular the Examples, it is within the skill of one in the art to determine such a detectable amount.

IV. D. Radiation Treatment

The disclosed targeting ligands are useful for x-ray guided drug delivery. Targeted drug delivery to a tumor in a subject can be performed by irradiating the tumor prior to, concurrent with, or subsequent to administration of a composition of the presently disclosed subject matter. In accordance with the in vivo panning methods for discovery of the targeting ligands, the tumor is irradiated in some embodiments 0 hours to about 24 hours before administration of the composition, and in some embodiments about 4 hours to about 24 hours before administration of the composition.

Low doses of radiation can be used for selective targeting using the peptide ligands disclosed herein. In some embodiments, the dose of radiation comprises up to about 2 Gy ionizing radiation. Higher radiation doses can also be used, especially in the case of local radiation treatment as described hereinbelow.

Radiation can be localized to a tumor using conformal irradiation, brachytherapy, or stereotactic irradiation. The threshold dose for inductive changes can thereby be exceeded in the target tissue but avoided in surrounding normal tissues. In some embodiments, doses of at least about 2 Gy ionizing radiation can be used, and in some embodiments a dose of about 10 Gy to about 20 Gy ionizing radiation can be used. For treatment of a subject having two or more tumors, local irradiation enables differential drug administration and/or dose at each of the two or more tumors. Alternatively, whole body irradiation can be used, as permitted by the low doses of radiation required for targeting of ligands disclosed herein. Radiotherapy methods suitable for use in the practice of this invention can be found in Leibel & Phillips, 1998, among other sources.

IV. E. Monitoring Distribution In Vivo

In some embodiments of the presently disclosed subject matter, a diagnostic and/or therapeutic composition for x-ray-guided drug delivery comprises a label that can be detected in vivo. The term "in vivo", as used herein to describe imaging or detection methods, refer to generally non-invasive methods such as scintigraphic methods, magnetic resonance imaging, ultrasound, or fluorescence, each described briefly hereinbelow. The term "non-invasive methods" does not exclude methods employing administration of a contrast agent to facilitate in vivo imaging.

The label can be conjugated or otherwise associated with a targeting ligand (e.g., any one of SEQ ID NOs: 1-13, 18, and 20-55), a therapeutic, a diagnostic agent, a drug carrier, or combinations thereof. Following administration of the labeled composition to a subject, and after a time sufficient for binding, the biodistribution of the composition can be visualized. The term "time sufficient for binding" refers to a temporal duration that permits binding of the labeled agent to a radiation-induced target molecule.

Scintigraphic Imaging.

Scintigraphic imaging methods include SPECT (Single Photon Emission Computed Tomography), PET (Positron Emission Tomography), gamma camera imaging, and rectilinear scanning. A gamma camera and a rectilinear scanner each represent instruments that detect radioactivity in a single plane. Most SPECT systems are based on the use of one or more gamma cameras that are rotated about the subject of analysis, and thus integrate radioactivity in more than one dimension. PET systems comprise an array of detectors in a ring that also detect radioactivity in multiple dimensions.

A representative method for SPECT imaging is presented in Example 2. Other imaging instruments suitable for practicing the method of the presently disclosed subject matter, and instruction for using the same, are readily available from commercial sources. Both PET and SPECT systems are offered by ADAC of Milpitas, Calif., United States of America, and Siemens of Hoffman Estates, Ill., United States of America. Related devices for scintigraphic imaging can also be used, such as a radio-imaging device that includes a plurality of sensors with collimating structures having a common source focus.

When scintigraphic imaging is employed, the detectable label comprises in some embodiments a radionuclide label, in some embodiments a radionuclide label selected from the group consisting of $^{18}$-fluorine, $^{64}$copper, $^{65}$copper, $^{67}$gallium, $^{68}$gallium, $^{77}$bromine, $^{80m}$bromine, $^{95}$ruthenium, $^{97}$ruthenium, $^{103}$ruthenium, $^{105}$ruthenium, $^{99m}$technetium, $^{107}$mercury, $^{203}$mercury, $^{123}$iodine, $^{124}$iodine, $^{125}$iodine, $^{126}$iodine, $^{131}$iodine, $^{133}$iodine, $^{111}$indium, $^{113m}$indium, $^{99m}$rhenium, $^{105}$rhenium, $^{101}$rhenium, $^{186}$rhenium, $^{188}$rhenium, $^{121m}$tellurium, $^{122m}$tellurium, $^{125m}$tellurium, $^{165}$thulium, $^{167}$thulium, $^{168}$thulium, and nitride or oxide forms derived there from. In some embodiments, the radionuclide label comprises $^{131}$ iodine or $^{99m}$Tc.

Methods for radionuclide labeling of a molecule so as to be used in accordance with the disclosed methods are known in the art. For example, a targeting molecule can be derivatized so that a radioisotope can be bound directly to it (Yoo et al., 1997). Alternatively, a linker can be added that to enable conjugation. Representative linkers include diethylenetriamine pentaacetate (DTPA)-isothiocyanate, succinimidyl 6-hydrazinium nicotinate hydrochloride (SHNH), and hexamethylpropylene amine oxime (HMPAO) (Chattopadhyay et al., 2001; Sagiuchi et al., 2001; Dewanjee et al., 1994; U.S. Pat. No. 6,024,938). Additional methods can be found in U.S. Pat. No. 6,080,384; Hnatowich et al., 1996; and Tavitian et al., 1998.

When the labeling moiety is a radionuclide, stabilizers to prevent or minimize radiolytic damage, such as ascorbic acid, gentisic acid, or other appropriate antioxidants, can be added to the composition comprising the labeled targeting molecule.

Magnetic Resonance Imaging (MRI).

Magnetic resonance image-based techniques create images based on the relative relaxation rates of water protons in unique chemical environments. As used herein, the term "magnetic resonance imaging" refers to magnetic source techniques including convention magnetic resonance imaging, magnetization transfer imaging (MTI), proton magnetic resonance spectroscopy (MRS), diffusion-weighted imaging (DWI) and functional MR imaging (fMRI). See Rovaris et al., 2001; Pomper & Port, 2000; and references cited therein.

Contrast agents for magnetic source imaging include but are not limited to paramagnetic or superparamagnetic ions, iron oxide particles (Weissleder et al., 1992; Shen et al., 1993), and water-soluble contrast agents. Paramagnetic and superparamagnetic ions can be selected from the group of metals including iron, copper, manganese, chromium, erbium, europium, dysprosium, holmium and gadolinium. Preferred metals are iron, manganese and gadolinium; most preferred is gadolinium.

Those skilled in the art of diagnostic labeling recognize that metal ions can be bound by chelating moieties, which in turn can be conjugated to a therapeutic agent in accordance with the methods of the presently disclosed subject matter. For example, gadolinium ions are chelated by diethylenetriaminepentaacetic acid (DTPA). Lanthanide ions are chelated by tetraazaclododocane compounds. See U.S. Pat. Nos. 5,738,837 and 5,707,605. Alternatively, a contrast agent can be carried in a liposome (Schwendener, 1992).

Images derived using a magnetic source can be acquired using, for example, a superconducting quantum interference device magnetometer (SQUID, available with instruction from Quantum Design of San Diego, Calif., United States of America). See U.S. Pat. No. 5,738,837.

Ultrasound.

Ultrasound imaging can be used to obtain quantitative and structural information of a target tissue, including a tumor. Administration of a contrast agent, such as gas microbubbles, can enhance visualization of the target tissue during an ultrasound examination. Preferably, the contrast agent can be selectively targeted to the target tissue of interest, for example by using a peptide for x-ray guided drug delivery as disclosed herein. Representative agents for providing microbubbles in vivo include but are not limited to gas-filled lipophilic or lipid-based bubbles (e.g., U.S. Pat. Nos. 6,245,318, 6,231,834, 6,221,018, and 5,088,499). In addition, gas or liquid can be entrapped in porous inorganic particles that facilitate microbubble release upon delivery to a subject (U.S. Pat. Nos. 6,254,852 and 5,147,631).

Gases, liquids, and combinations thereof suitable for use with the invention include air; nitrogen; oxygen; is carbon dioxide; hydrogen; nitrous oxide; an inert gas such as helium, argon, xenon or krypton; a sulphur fluoride such as sulphur hexafluoride, disulphur decafluoride or trifluoromethylsulphur pentafluoride; selenium hexafluoride; an optionally halogenated silane such as tetramethylsilane; a low molecular weight hydrocarbon (e.g. containing up to 7 carbon atoms), for example an alkane such as methane, ethane, a propane, a butane or a pentane, a cycloalkane such as cyclobutane or cyclopentane, an alkene such as propene or a butene, or an alkyne such as acetylene; an ether; a ketone; an ester; a halogenated low molecular weight hydrocarbon (e.g. containing up to 7 carbon atoms); or a mixture of any of the foregoing. Halogenated hydrocarbon gases can show extended longevity, and thus are preferred for some applications. Representative gases of this group include decafluorobutane, octafluorocyclobutane, decafluoroisobutane, octafluoropropane, octafluorocyclopropane, dodecafluoropentane, decafluorocyclopentane, decafluoroisopentane, perfluoropexane, perfluorocyclohexane, perfluoroisohexane, sulfur hexafluoride, and perfluorooctaines, perfluororononanes; perfluorodecanes, optionally brominated.

Attachment of targeting ligands to lipophilic bubbles can be accomplished via chemical crosslinking agents in accordance with standard protein-polymer or protein-lipid attachment methods (e.g., via carbodiimide (EDC) or thiopropionate (SPDP)). To improve targeting efficiency, large gas-filled bubbles can be coupled to a targeting ligand using a flexible spacer arm, such as a branched or linear synthetic polymer (U.S. Pat. No. 6,245,318). A targeting ligand can be attached to the porous inorganic particles by coating, adsorbing, layering, or reacting the outside surface of the particle with the targeting ligand (U.S. Pat. No. 6,254,852).

A description of ultrasound equipment and technical methods for acquiring an ultrasound dataset can be found in Coatney, 2001; Lees, 2001; and references cited therein.

Fluorescent Imaging.

Non-invasive imaging methods can also comprise detection of a fluorescent label. A drug comprising a lipophilic component (therapeutic agent, diagnostic agent, vector, or drug carrier) can be labeled with any one of a variety of lipophilic dyes that are suitable for in vivo imaging. See e.g. Fraser, 1996; Ragnarson et al., 1992; and Heredia et al., 1991.

Representative labels include but are not limited to carbocyanine and aminostyryl dyes, preferably long chain dialkyl carbocyanines (e.g., DiI, DiO, and DiD available from Molecular Probes Inc. of Eugene, Oreg., United States of America) and dialkylaminostyryl dyes. Lipophilic fluorescent labels can be incorporated using methods known to one of skill in the art. For example VYBRANT™ cell labeling solutions are effective for labeling of cultured cells of other lipophilic components (Molecular Probes Inc. of Eugene, Oreg., United States of America). Preparation of liposomes comprising a targeting ligand and a DiI detectable label are described in Example 1.

A fluorescent label can also comprise sulfonated cyanine dyes, including Cy5.5 and Cy5 (available from Amersham of Arlington Heights, Ill., United States of America), IRD41 and IRD700 (available from Li-Cor, Inc. of Lincoln, Nebr.), NIR-1 (available from Dejindo of Kumamoto, Japan), and LaJolla Blue (available from Diatron of Miami, Fla., United States of America). See also Licha et al., 2000; Weissleder et al., 1999; and Vinogradov et al., 1996.

In addition, a fluorescent label can comprise an organic chelate derived from lanthanide ions, for example fluorescent chelates of terbium and europium (U.S. Pat. No. 5,928,627). Such labels can be conjugated or covalently linked to a drug as disclosed therein.

For in vivo detection of a fluorescent label, an image is created using emission and absorbance spectra that are appropriate for the particular label used. The image can be visualized, for example, by diffuse optical spectroscopy. Additional methods and imaging systems are described in U.S. Pat. Nos. 5,865,754; 6,083,486; and 6,246,901, among other places.

IV. F. In Vitro Detection

The presently disclosed subject matter further provides methods for diagnosing a tumor, wherein a tumor sample or biopsy is evaluated in vitro. In some embodiments, a targeting ligand of the presently disclosed subject matter comprises a detectable label such as a fluorescent, epitope, or radioactive label, each described briefly hereinbelow.

Fluorescence.

Any detectable fluorescent dye can be used, including but not limited to FITC (fluorescein isothiocyanate), FLUOR X™, ALEXA FLUOR®, OREGON GREEN®, TMR (tetramethylrhodamine), ROX (X-rhodamine), TEXAS RED®, BODIPY® 630/650, and Cy5 (available from Amersham Pharmacia Biotech of Piscataway, N.J., United States of America, or from Molecular Probes Inc. of Eugene, Oreg., United States of America).

A fluorescent label can be detected directly using emission and absorbance spectra that are appropriate for the particular label used. Common research equipment has been developed for in vitro detection of fluorescence, including instruments available from GSI Lumonics (Watertown, Mass., United States of America) and Genetic MicroSystems Inc. (Woburn, Mass., United States of America). Most of the commercial systems use some form of scanning technology with photomultiplier tube detection. Criteria for consideration when analyzing fluorescent samples are summarized by Alexay et al., 1996.

Detection of an Epitope.

If an epitope label has been used, a protein or compound that binds the epitope can be used to detect the epitope. A representative epitope label is biotin, which can be detected by binding of an avidin-conjugated fluorophore, for example avidin-FITC, as described in Example 7. Alternatively, the label can be detected by binding of an avidin-horseradish peroxidase (HRP) streptavidin conjugate, followed by colorimetric detection of an HRP enzymatic product. The production of a colorimetric or luminescent product/conjugate is measurable using a spectrophotometer or luminometer, respectively.

Autoradiographic Detection.

In the case of a radioactive label (e.g., $^{131}$I or $^{99m}$Tc) detection can be accomplished by conventional autoradiography or by using a phosphorimager as is known to one of skill in the art. A preferred autoradiographic method employs photostimulable luminescence imaging plates (Fuji Medical Systems of Stamford, Conn., United States of America). Briefly, photostimulable luminescence is the quantity of light emitted from irradiated phosphorous plates following stimulation with a laser during scanning. The luminescent response of the plates is linearly proportional to the activity (Amemiya et al., 1988; Hallahan et al., 2001b).

V. Identification of a Radiation-Induced Target Molecule

Targeting ligands obtained using the methods disclosed herein can be used to identify and/or isolate a target molecule that is recognized by the targeting ligand. Representative methods include affinity chromatography, biotin trapping, and two-hybrid analysis, each described briefly hereinbelow.

Affinity Chromatography.

A representative method for identification of a radiation-induced target molecule is affinity chromatography. For example, a targeting ligand as disclosed herein can be linked to a solid support such as a chromatography matrix. A sample derived from an irradiated tumor is prepared according to known methods in the art, and such sample is provided to the column to permit binding of a target molecule. The target molecule, which forms a complex with the targeting ligand, is eluted from the column and collected in a substantially isolated form. The substantially isolated target molecule is then characterized using standard methods in the art. See Deutscher, 1990.

Biotin Trapping.

A related method employs a biotin-labeled targeting ligand such that a complex comprising the biotin-labeled targeting ligand bound to a target molecule can be purified based on affinity to avidin, which is provided on a support (e.g., beads, a column). A targeting ligand comprising a biotin label can be prepared by any one of several methods, including binding of biotin maleimide [3-(N-maleimidylpropionyl)biocytin] to cysteine residues of a peptide ligand (Tang & Casey, 1999), binding of biotin to a biotin acceptor domain, for example that described in *K. pneumoniae* oxaloacetate decarboxylase, in the presence of biotin ligase (Julien et al., 2000), attachment of biotin amine to reduced sulfhydryl groups (U.S. Pat. No. 5,168,037), and chemical introduction of a biotin group into a nucleic acid ligand, (Carninci et al., 1996). In some embodiments, a biotin-labeled targeting ligand and the unlabeled same target ligand show substantially similar binding to a target molecule.

Two-Hybrid Analysis.

As another example, targeting ligands can be used to identify a target molecule using a two-hybrid assay, for example a yeast two-hybrid or mammalian two-hybrid assay. In one embodiment of the method, a targeting ligand is fused to a DNA binding domain from a transcription factor (this fusion protein is called the "bait"). Representative DNA-binding domains include those derived from GAL4, LEXA, and mutant forms thereof. One or more candidate target molecules is fused to a transactivation domain of a transcription factor (this fusion protein is called the "prey"). Representative transactivation domains include those derived from *E. coli* B42, GAL4 activation domain II, herpes simplex virus VP16, and mutant forms thereof. The fusion proteins can also include a nuclear localization signal.

The transactivation domain should be complementary to the DNA-binding domain, meaning that it should interact with the DNA-binding domain so as to activate transcription of a reporter gene comprising a binding site for the DNA-binding domain. Representative reporter genes enable genetic selection for prototrophy (e.g. LEU2, HIS3, or LYS2 reporters) or by screening with chromogenic substrates (lacZ reporter).

The fusion proteins can be expressed from a same vector or different vectors. The reporter gene can be expressed from a same vector as either fusion protein (or both proteins), or from a different vector. The bait, prey, and reporter genes are co-transfected into an assay cell, for example a microbial cell (e.g., a bacterial or yeast cell), an invertebrate cell (e.g., an insect cell), or a vertebrate cell (e.g., a mammalian cell, including a human cell). Cells that display activity of the encoded reporter are indicative of a binding interaction between the peptide and the candidate target molecule. The protein encoded by such a clone is identified using standard protocols known to one of skill in the art.

Additional methods for yeast two-hybrid analysis can be found in Brent & Finley, 1997; Allen et al., 1995; Lecrenier et al., 1998; Yang et al., 1995; Bendixen et al., 1994; Fuller et al., 1998; Cohen et al., 1998; Kolonin & Finley, 1998; Vasavada et al., 1991; Rehrauer et al., 1996; and Fields & Song, 1989.

EXAMPLES

The following Examples have been included to illustrate modes of the presently disclosed subject matter. These Examples illustrate standard laboratory practices of the co-inventors. In light of the present disclosure and the general level of skill in the art, those of skill will appreciate that the following Examples are intended to be exemplary only and that numerous changes, modifications, and alterations can be employed without departing from the scope of the presently disclosed subject matter.

Example 1

X-Ray Guided Delivery of Fibrinogen-Conjugated Liposomes and Microspheres

Preparation of Radiolabeled Microspheres.

Albumin microspheres (Martodam et al., 1979) were resuspended using 10 ml of sterile normal saline (0.9% NaCl). One-half milliliter of the reconstituted microsphere was added to a 1.5 ml conical polypropylene tube previously coated with lodgen (Pierce of Rockford, Ill.). To this, 11.3 mCi (418 megabecquerel (MBq)) of $^{131}$I (DuPont Pharmaceuticals of Wilmington, Del., United States of America) was added in approximately 11 µl of saline and allowed to incubate at room temperature for 30 minutes. Following incubation, the microspheres were transferred to a 15 ml sterile centrifuge tube, diluted to 10 ml with normal saline and centrifuged at 1,500 g for seven minutes. The supernatant was removed and discarded. The microspheres were washed one additional time with 10 ml of normal saline and centrifuged. The microspheres were suspended in 2 ml of normal saline for injection. Final yield was 4.8 mCi (177.6 MBq) of radioiodinated microspheres in 2 ml saline. Radiochemical yield was 42.4%.

Preparation of Fibrinogen-Conjugated Liposomes

The lipophilic SH reactive reagent with a long spacing arm was synthesized from maleimide-PEG 2000-NSH ester (Prochem Chemicals of High Point, N.C., United States of America), dioleoylphosphatidylethanolanime (DOPE, available from AVANTI® Polar Lipids, Inc. of Alabaster, Ala., United States of America) and triethylamine in chloroform (1:1:1.5). Resulting maleimide-PEG 2000-DOPE was purified by flash column. Under stirring, to a solution of fibrinogen (2 mg/ml) in 0.01 M HEPES 0.15 NaCl buffer pH7.9, containing 10 mM EDTA and 0.08% NaN$_3$ was added in 5-fold excess of freshly prepared Traut's reagent (2-iminothiolane hydrochloride) in the same buffer. The reaction was allowed to proceed for 30 minutes at 0° C.

SH-fibrinogen was purified using a PD-10 desalting and buffer exchange column (Amersham Pharmacia Biotech of Piscataway, N.J.). PEG 2000-PE, cholesterol, Dipalmitoyl phosphocholine (AVANTI® Polar Lipids, Inc. of Alabaster, Ala., United States of America), DiI (lipid fluorescent marker available from Molecular Probes of Eugene, Oreg., United States of America), and maleimide-PEG-2000-DOPE were dissolved in chloroform and mixed at a molar ratio of 10:43:43:2:2, respectively, in a round bottom flask. The organic solvent was removed by evaporation followed by desiccation under vacuum for 2 hours. Liposomes were prepared by hydrating the dried lipid film in PBS at a lipid concentration of 10 mM. The suspension was then sonicated 3×5 minutes, or until the solution appeared clear, to form unilamellar liposomes of 100 nM in diameter. To conjugate thiolated fibrinogen to maleimide containing liposomes, prepared vesicles and thiolated protein were mixed in 10 mm Hepes, 0.15 M NaCl and EDTA pH 6.5. The final concentrations for proteins and liposomes were 0.25 g/L and 2.5 mM, respectively. The peptide/liposome mixture was incubated for 18 hours at room temperature. Vesicles were then separated from unconjugated peptide using a SEPHAROSE™ 4B-CL filtration column (Amersham Pharmacia Biotech of Piscataway, N.J., United States of America).

Liposomes were fluorescently labeled with DiI fluorescent marker (Molecular Probes, Inc.) according to the manufacturer's instructions. Labeled liposomes were administered by tail vein injection to tumor bearing mice. Tumors were treated with 4 Gy either prior to administration or after administration of fibrinogen-liposome conjugates. Tumors were fixed and sectioned at 24 hours following irradiation. Fluorescence was imaged by ultraviolet microscopy (100×).

Image Analysis.

Tumor bearing mice were imaged at one hour and 24 hours post-administration of radiolabeled proteins. Planar pinhole gamma camera imaging was performed on a single-head gamma camera (HELIX® model from General Electric Medical Systems of Milwaukee, Wis., United States of America) using a cone-shaped pinhole collimator with a 4 mm diameter Tungsten aperture. Pinhole collimation offers the advantage of improved photon detection efficiency (sensitivity) and spatial resolution when compared with conventional, parallel multi-hole collimators. Pinhole planar imaging with a small source-aperture separation can provide high-resolution images combined with large magnification. Each scan consisted of a 180 second acquisition (256×256 acquisition matrix) with a 10% energy window centered on 364 keV. The source-aperture separation was 6.0 cm.

Prior to imaging analysis in animals, a uniform $^{131}$I disk source was imaged in order to measure the angular dependence of the pinhole collimator—gamma camera system detection efficiency with distance from the center of the pinhole. Angular sensitivity, normalized to 1.0 at the center of the pinhole, was then used to scale the mouse data in order to correct image counts for this geometrical effect. A calibration source of known $^{131}$I activity was also scanned at a 6.0 cm source-aperture separation distance in order to measure system sensitivity along the center of the pinhole.

Peptide biodistribution data was assessed using two measures: (1) tumor-to-background ratio (T/B) of observed activity; and (2) tumor uptake activity in µCi. Both types of data were obtained using region-of-interest (ROI) analysis. For both measurements an 11×11 ROI was used to determine mean counts within the tumor ($\sigma_T$) and at five different locations within the mouse background ($\sigma_B$). These readings were scaled to account for geometric sensitivity and the ratio of tumor uptake to total animal uptake (R) was computed according to the relation, $$R = \frac{\sigma_T}{(\sigma_T + \sigma_B)}.$$

Activity uptake in the tumor was then approximated by the product of the amount of activity administered into the animal multiplied by the value obtained for R above. Tumor-background ratios were determined according to the general expression:

$$\left(\frac{T}{B}\right) = \frac{\sigma_T}{\sigma_B}.$$

Fibrinogen Coated Microsphere Localize to Irradiated Tumors.

Fibrinogen-coated microspheres were radiolabeled with $^{131}$I and administered by tail vein injection into tumor bearing mice, and tumors were irradiated with 6 Gy. The specificity of fibrinogen-coated albumin was determined by measuring the intensity of gamma detection within regions of interest (ROI) and well counts of tumor and other tissues. In animals receiving localized radiation at the tumor site, 90% of the measured radioactivity was localized to the tumor, and 10% of the radioactivity was diffusely distributed throughout the entire animal model. In untreated controls, 10% of radioactive counts were localized to the tumor (p<0.001).

During optimization studies, tumors were irradiated immediately before or immediately after tail vein injection. Both schedules were effective in achieving $^{131}$I-fibrinogen-coated microsphere binding. However, tumor irradiation subsequent to microsphere administration achieved increased targeting specificity when compared to tumors irradiated prior to microsphere administration. Microspheres lacking the fibrinogen ligand did not bind irradiated tumors.

To quantify a level of preferential binding of fibrinogen-coated microspheres in irradiated tumors, data were normalized based on background levels of radiation. Fibrinogen-coated microspheres were 100-fold more abundant in irradiated tumors compared to non-tumor control tissues. By contrast, microspheres lacking the fibrinogen ligand were detected at similar levels in tumor and non-tumor control tissues.

To determine whether fibrinogen-conjugated microspheres bind irradiated non-tumor control tissues, the entire hind quarters of mice bearing hind limb tumors were irradiated, and radiolabeled fibrinogen-coated microspheres were administered immediately after irradiation. Well counts of all tissues were performed at 24 hours after irradiation. 90% of radioactive counts were detected in the tumor. By contrast, 2% of radioactive counts were detected in irradiated non-tumor control tissue, demonstrating selective targeting of fibrinogen-coated microspheres to irradiated tumors.

Fibrinogen-Liposome Conjugates Localize to Irradiated Tumors.

Fibrinogen-conjugated, fluorescently labeled liposomes were administered by tail vein into mice bearing tumors on both hind limbs. The right tumor was treated with radiation and the left tumor served as the untreated control. Untreated control tumors showed no fibrinogen-liposome conjugate binding whereas tumors irradiated immediately before or immediately after tail vein injection showed fibrinogen adhesion in blood vessels. The fluorescent marker was observed within the vascular lumen of tumor microvasculature.

Studies using radiolabeled fibrinogen-conjugated liposomes gave similar results. When liposomes were administered after tumor irradiation, 89% of fibrinogen-coated liposomes localized to tumors. When liposomes were administered immediately prior to tumor irradiation, 69% of liposomes showed tumor localization. By contrast, in untreated controls, a background level of 9% of fibrinogen-coated liposomes localized to the tumor.

Example 2

Clinical Trials of X-Ray-Guided Delivery Using a Peptide Ligand Ligand Preparation and Administration Biapcitide (ACUTECT® available from Diatide, Inc. of Londonderry, N.H., United States of America) is a synthetic peptide that binds to GP-IIb/IIIa receptors on activated platelets (Hawiger et al., 1989; Hawiger & Timmons, 1992). Biapcitide was labeled with $^{99m}$Tc in accordance with a protocol provided by Diatide Inc.

Reconstituted $^{99m}$Tc-labeled biapcitide was administered to patients at a dose of 100 mcg of biapcitide radiolabeled with 10 mCi of $^{99m}$Tc. Patients received $^{99m}$Tc-labeled biapcitide intravenously immediately prior to irradiation. Patients were then treated with 10 Gy or more. Patients underwent gamma camera imaging prior to irradiation and 24 hours following irradiation. Following planar image acquisition, those patients showing uptake in irradiated tumors underwent tomographic imaging using SPECT and repeat imaging at 24 hours. Patients showing no uptake on planer images during this 24-hour time frame had no further imaging. Each patient had an internal control, which consisted of a baseline scan immediately following administration of $^{99m}$Tc-labeled biapcitide.

Patients were treated with X-irradiation ranging from 4 to 18 MV photon using external beam linear accelerator at Vanderbilt University. Appropriate blocks, wedges, and bolus to deliver adequate dose to the planned target volume was utilized. The site of irradiation, treatment intent and normal tissue considerations determined the radiation dosage and volume. When stereotactic radiosurgery was used, the dose was prescribed to the tumor periphery.

Image Analysis.

Image acquisition consisted of both planar and single photon emission computed tomography (SPECT) studies. Planar studies were performed on a dual-head gamma camera (Millenium VG—Variable Geometry model available from General Electric Medical Systems of Milwaukee, Wis., United States of America) equipped with low energy high-resolution (LEUR) collimators. This type of collimator represents a compromise between sensitivity (photon counting efficiency) and image resolution. Planar nuclear medicine images were acquired with a 256×256 acquisition matrix (pixel size approximately 0.178 cm/pixel) for 10 minutes. In order to maximize collimator-gamma camera system sensitivity the source-to-detector surface distance was minimized to the extent that patient geometry allows. The spatial distribution of fibrinogen within the planar image was measured using region-of-interest (ROI) analysis. Two different size ROI's (5×5 pixel, and 15×15 pixel) was used in both the tumor and surrounding organs and tissues in the patient. The rationale for using ROIs with different dimensions is to be able to quantify image counts while at the same time isolating any possible influence of ROI size on the results. Tumor-to-background ratios were computed as the ratio of average counts in the tumor region divided by average counts in surrounding organs and tissues, each corrected for background. Background counts was determined based on ROI analysis of a separate planar acquisition performed in the absence of a radioactive source.

Three-dimensional nuclear medicine SPECT examinations were performed using the same dual-head gamma camera system. Each SPECT study comprised a 360 scan acquired with a step-and-shoot approach utilizing the following acquisition parameters: three increments between views, a 256×256×64 acquisition matrix, LEUR collimation and 60 seconds per view. Images were reconstructed using analytical filtered back-projection and statistical maximum likelihood techniques with photon attenuation correction and post-reconstruction deconvolution filtering for approximate detector response compensation. In this case, correction for background consisted of subtracting counts acquired in a single 60-second planar view from all views of the SPECT projection data prior to image reconstruction. SPECT tumor-to-background ratios were computed using quantitative ROI techniques identical to the planar studies.

Results.

Administration of a $^{99m}$Tc-labeled biapcitide, an RGD peptide mimetic, immediately prior to radiation resulted in tumor binding in 4 of 4 patients (Hallahan et al., 2001a). Two patients among this group had second neoplasms that were not treated with radiation, and binding of $^{99m}$Tc-labeled biapcitide was not observed in the untreated tumor. Administration of the $^{99m}$Tc-labeled biapcitide within one hour following radiation also failed to show localization of the targeting molecule to the tumor (Hallahan et al., 2001a).

Example 3

Response of Tumor Blood Vessels to Ionizing Radiation

To determine the response of tumor blood vessels to ionizing radiation, a tumor vascular window and Doppler sonography were used to measure the change in tumor blood vessels (Donnelly et al., 2001; Geng et al., 2001). Tumors implanted into the window model developed blood vessels within 1 week. Tumors were then treated with radiation and the response of blood vessels was imaged by use of light microscopy. Radiation doses in the range of 2-3 Gy increased the vascularity within tumors. In contrast, larger doses of radiation such as 6 Gy reduced tumor vascularity.

Established tumors were studied to determine whether there is a dose-dependent change in blood flow following irradiation. Tumors in the hind limb were grown to approximately 1 cm in diameter. Blood flow within tumors was measured by use of power Doppler (Donnelly et al., 2001). Tumors were treated with 3 Gy or 6 Gy ionizing radiation, and changes in tumor blood flow were measured using power Doppler sonography. A radiation dose of 3 Gy achieved an increase in tumor blood flow. In contrast, radiation doses of 6 Gy or higher markedly reduced tumor blood flow.

Example 4

Preparation of a Recombinant Peptide Library in Phage

A population of DNA fragments encoding recombinant peptide sequences was cloned into the T7 SELECT™ vector (Novagen of Madison, Wis., United States of America). Cloning at the EcoR I restriction enzyme recognition site places the recombinant peptide in-frame with the 10B protein such that the peptide is displayed on the capsid protein. The resulting reading frame requires an AAT initial codon followed by a TCX codon.

The molar ratio between insert and vector was 1:1. Size-fractionated cDNA inserts were prepared by gel filtration on sepharose 4B and ranged from 27 base pairs to 33 base pairs. cDNAs were ligated by use of the DNA ligation kit (Novagen). Recombinant T7 DNA was packaged according to the manufacturer's instructions and amplified prior to biopanning in animal tumor models. The diversity of the library was $10^7$.

Example 5

In Vivo Panning for Peptide Ligands to Radiation-Induced Molecules

GL261 murine glioma cells and Lewis lung carcinoma cells were implanted into the hind limb of C57BL6 mice (Hallahan et al., 1995b; Hallahan et al., 1998; Hallahan & Virudachalam, 1999).

To determine the optimal time at which peptides bind within tumors, phage were administered at 1 hour before, at 1 hour after, and at 4 hours after irradiation of both LLC and GL261 tumors. Phage were recovered from tumors when administered 4 hours after irradiation. Phage administered 1 hour before or 1 hour after irradiation were not recovered from tumors. These data indicate that the optimal time of administration is beyond 1 hour after irradiation.

For in vivo panning, tumors were irradiated with 3 Gy and approximately $10^{10}$ phage (prepared as described in Example 4) were administered by tail vein injection into each of the tumor bearing mice at 4 hours following irradiation. Tumors were recovered at one hour following injection and amplified in BL21 bacteria. Amplified phage were pooled and re-administered to a tumor-bearing mouse following tumor irradiation. The phage pool was sequentially administered to a total of 6 animals. As a control, wild type phage lacking synthetic peptide inserts were identically administered to a second experimental group of animals.

To determine the titer of phage binding in a tumor or in normal tissue, recovered phage were amplified in BL21 bacteria. Bacteria were plated and the number of plaques present were counted. To determine the total phage output per organ, the number of plaque forming units (PFU) on each plate was divided by the volume of phage plated and the weight of each organ. Normal variation was observed as a 2-fold difference in PFU.

In the present study, background binding within tumor blood vessels was approximately $10^4$ phage. Phage that bound to the vasculature within irradiated tumors show enrichment in the tumor relative to other organs and enrichment in the irradiated tumor relative to the control phage without DNA insert. Phage that home to irradiated tumors showed a background level of binding in control organs that was lower than control phage without DNA insert.

Following 6 rounds of in vivo panning, fifty recombinant phage peptides that bound within irradiated tumors were randomly selected for further analysis. The nucleic acid sequence encoding recombinant phage was amplified by PCR using primers set forth as SEQ ID NOs: 14-15 (available from Novagen of Madison, Wis., United States of America). An individual phage suspension was used as template. Amplified peptides were sequenced using an ABI PRISM® 377 sequencer (Applied Biosystems of Foster City, Calif., United States of America). The sequences of the encoded peptides are listed in Table 1. Several conserved subsequences were deduced from the recovered peptides and are presented in Table 2.

Peptide sequences recovered from both tumor types include NHVGGSSV (SEQ ID NO: 1), NSLRGDGSSV (SEQ ID NO: 2), and NSVGSRV (SEQ ID NO: 4). Of the peptide sequences recovered from 6 irradiated tumors, 56% had the subsequence GSSV (SEQ ID NO: 5), 18% had the sequence RGDGSSV (SEQ ID NO: 6), and 4% had the sequence GSRV (SEQ ID NO: 7). Approximately 22-40 of $10^6$ injected phage were recovered from irradiated tumors having a peptide insert comprising the subsequence GSSV (SEQ ID NO: 5). By contrast, no phage were from irradiated tumors following administration of $10^6$ wild type phage.

TABLE 1

Peptides Identified by In Vivo Panning of LLC and GL261 Tumors

| Peptide Sequence | Number of Phage Recovered from LLC tumors (Frequency) | Number of Phage Recovered from GL261 tumors (Frequency) |
|---|---|---|
| NHVGGSSV (SEQ ID NO: 1) | 7 (28%) | 12 (48%) |
| NSLRGDGSSV (SEQ ID NO: 2) | 7 (28%) | 2 (8%) |
| NSVRGSGSGV (SEQ ID NO: 3) | 7 (28%) | 0 |
| NSVGSRV (SEQ ID NO: 4) | 1 (4%) | 3 (12%) |
| Unique Sequences | 3 (12%) | 8 (32%) |

TABLE 2

Conserved Motifs within Peptides Identified by In Vivo Panning

| Conserved Sequence | Frequency of Recovery |
|---|---|
| GSSV (SEQ ID NO: 13) | 56% |
| GSXV (SEQ ID NO: 8) | 78% |
| NSXRGXGS (SEQ ID NO: 9) | 32% |
| NSV (SEQ ID NO: 10) | 22% |
| NSXR (SEQ ID NO: 11) | 32% |
| NXVG (SEQ ID NO: 12) | 46% |

Example 6

Peptide Targeting in Additional Tumors

The binding properties of phage encoding NHVGGSSV (SEQ ID NO: 1), NSLRGDGSSV (SEQ ID NO: 2), NSVRGSGSGV (SEQ ID NO: 3), and NSVGSRV (SEQ ID NO: 4) were additionally characterized in a B16F0 melanoma model. Peptides set forth as SEQ ID NOs: 1 and 2 bound within the melanoma, lung carcinoma, and glioma tumor models. SEQ ID NO: 3 bound within glioma and melanoma, and SEQ ID NO: 4 bound within lung carcinoma and glioma.

Example 7

Characterization of Peptide Binding to Irradiated Tumors

To determine where recombinant peptides bind in tumor blood vessels, the biodistribution of biotinylated peptides was assessed. Tumors were treated with 3 Gy and biotinylated peptides were administered by tail vein at 4 hours following irradiation. Tumors were recovered 30 minutes following administration of biotinylated peptides. Tumors were snap frozen and sectioned on a cryostat. Frozen sections were then incubated with Avidin-FITC (fluorescein isothiocyante) and imaged by fluorescent microscopy. Recombinant peptides (for example, those set forth in Table 1) were observed to bind the vascular endothelium within tumor blood vessels.

The anti-$\alpha_{2b}\beta_3$ monoclonal antibody was administered by tail vein to determine whether this receptor is required for recombinant phage binding in irradiated tumors. Phage encoding SLRGDSSV (SEQ ID NO: 5) on the capsid protein were injected immediately after blocking antibody or control antibody. Phage were recovered from the tumor and controls organs and quantified by plaque formation. Radiation induced a 4-fold increase in phage binding in tumor. Blocking antibody eliminated induction of phage binding, while control antibody to P-selectin (on activated platelets) did not reduce phage binding. Thus, the tumor binding activity of targeting peptide SLRGDSSV (SEQ ID NO: 5) is dependent on its interaction with the $\alpha_{2b}\beta_3$ receptor.

Example 8

In Vivo Panning for Antibody Ligands to Radiation-Induced Molecules

A phage library comprising diverse single chain antibodies was prepared in M13 phage. The phage library was exposed to the radiation-induced neoantigens P-selectin (also called CD62P; GENBANK® Accession No. P98109) and/or platelet membrane glycoprotein IIB (also called CD41; GENBANK® Accession No. P08514) immobilized on glass slides. Phage were selected based on antigen binding, and selected phage were pooled as a biased library. For representative in vitro panning methods, see Fowlkes et al., 1992; Haaparanta & Huse, 1995; Jung & Pluckthun, 1997; Peter et al., 2000; Holzem et al., 2001; Chiu et al., 2000.

Phage identified by in vitro panning were tested on Western immunoblots to confirm binding to the P-selectin and platelet membrane glycoprotein IIB neoantigens. Phage that specifically bound P-selectin and platelet membrane glycoprotein IIB were subsequently used for in vivo panning to irradiated tumors as described in Example 5. Wild type phage were used as internal controls. Antibodies having substantial affinity for irradiated tumors were identified by observing an increased number of phage in the irradiated tumor when compared to a number of phage in a control organ (e.g., liver and lung). Phage antibodies with the greatest affinity for tumors were identified using the formula: number of phage in irradiated tumor/number of phage in each organ. Eight antibodies that bound P-selectin and fifteen antibodies that bound platelet membrane glycoprotein IIB were recovered following in vivo panning to irradiated tumors. Representative targeting antibodies identified by this method include the single chain antibodies set forth as SEQ ID NOs: 18 and 20 (encoded by SEQ ID NOs: 17 and 19, respectively), which recognize the radiation-induced neoantigens P-selectin and platelet membrane glycoprotein IIB, respectively.

Example 9

Conformational Changes Induced in Perlecan

Mass spectrometry analysis of the samples revealed that co-culturing HMVEC cells with H460 tumor cells induced several proteins' expression on the HMVEC cells. Among them, CYR61 and perlecan had been demonstrated to be important for tumor growth and angiogenesis. Most importantly, several proteins underwent conformational changes, by exposing some new biotinylation sites as well as hiding some other sites for biotinylation.

One such protein was the perlecan precursor (GENBANK® Accession No. P98160; SEQ ID NO: 56). Several subsequences of the perlecan precursor were found to undergo conformational changes upon co-culture as evidenced by the blocking of existing biotinylation sites. These subsequences are presented in Table 3.

TABLE 3

Conformational Changes Induced in Perlecan by Co-Culture

| Subsequence | Amino acids of SEQ ID NO: 56 | Biotinylation Site Blocked? |
|---|---|---|
| RPEEVCGPTQFR | 363-374 | Yes |
| LRFDQPDDF | 542-550 | No |
| NVRYELAR | 617-624 | Yes |
| GMLEPVQRPDVVLVGAGY | 625-642 | Yes |
| AHSVEECRCPIGY | 725-737 | Yes |
| SGLSCESCDAHF | 738-749 | No |
| ATATSCRPCPCPY | 806-818 | Yes |
| RFSDTCFLDTDGQATCDACAPGYTGR | 824-849 | Yes |
| RCESCAPGYEGNPIQPGGK | 850-868 | Yes |
| CRPVNQEIVR | 869-878 | No |
| RPVNQEIVR | 870-878 | Yes |
| TCESLGAGGYR | 1627-1637 | No |
| AVTLECVSAGEPR | 3129-3141 | No |
| CSATGSPAPTIHWSK | 3233-3247 | Yes |
| IAHVELADAGQYR | 3542-3554 | Yes |
| IAHVELADAGQY | 3542-3553 | Yes |

TABLE 3 -continued

Conformational Changes Induced in Perlecan by Co-Culture

| Subsequence | Amino acids of SEQ ID NO: 56 | Biotinylation Site Blocked? |
|---|---|---|
| IAHVELADAGQYRCTATN | 3542-3559 | Yes |
| AHLQVPER | 3654-3661 | Yes |
| VVPYFTQTPY | 3662-3671 | Yes |
| NGQKRVPGSPTNL | 3704-3716 | No |
| VCVCPAGFTGSR | 3868-3879 | Yes |
| SAEPLALGR | 4004-4012 | Yes |
| CLCLPGFSGPR | 4164-4174 | Yes |

Additional conformational changes were identified when the co-cultured cells were irradiated with 2 Gy, as new biotinylation sites were induced. These changes are summarized in Table 4.

TABLE 4

Conformational Changes Induced in Perlecan by Co-Culture and Irradiation

| Subsequence | Amino acids of SEQ ID NO: 56 | New Biotinylation Site Induced? |
|---|---|---|
| LRFDQPDDF | 542-550 | No |
| GHTPTQPGALNQR | 648-660 | Yes |
| SGLSCESCDAHF | 738-749 | No |
| CRPVNQEIVR | 869-878 | No |
| TCESLGAGGYR | 1627-1637 | No |
| AVTLECVSAGEPR | 3129-3141 | No |
| NGQKRVPGSPTNL | 3704-3716 | No |
| AGLSSGFIGCVR | 3810-3821 | Yes |
| GCVGEVSVNGK | 4075-4085 | Yes |
| CQQGSGHGIAESDW | 4175-4188 | Yes |

Example 10

Identification of Additional Targeting Peptides by in Vivo Panning

Tumors (Lewis Lung Carcinoma, LLC) were implanted into both sides of hind limbs of C57 mice, and one side of tumor was treated with 2 Gy of radiation when the tumors reached a size of 1 cm in diameter. Six T7 phage-based random peptide libraries were screened separately by injection through tail veins at 18 hours after the radiation, and phages were circulated for 1 hour before the mice were sacrificed to recover phages from the radiated tumor. The recovered phages were amplified by infecting a bacterial host as described hereinabove, and used as input for the next round of biopanning.

After five rounds of in vivo biopanning, single phage clones were isolated and the peptide sequence was deduced by sequenced the relevant fragment in the phage genome. Dozens of peptides were recovered from the irradiated tumors, with several enriched to be dominant after the final round of biopanning. The isolated phage were purified and injected into tumor-bearing mice. Phages in tissues were visualized using an anti-T7 phage antibody in conjunction with a FITC-conjugated secondary antibody. DAPI staining was used to localize the cell nucleus.

Representative data indicated that the isolated phage targeted the irradiated tumor cells by the peptide displayed on its surface. Certain of these peptide sequences are presented in SEQ ID NOs: 21-46.

Example 11

In Vitro Panning for Nuclear Targeting Peptides

T7-based linear peptides (x12, 16 and 20) were subjected for biopanning on HUVEC monolayers. After 20 hours incubation at 37° C., phages recovered from nuclei were amplified and used for the following round of selection. Titration result for phages recovered from nuclei and cytoplasm in all the rounds of screening showed that some nucleus-homing phages had been enriched in the biopanning process. Phages from the third round nucleus extraction were sequenced and are presented in SEQ ID NOs: 47-55.

A BLAST search indicated that the isolated sequence is close to a well-studied sequence motif which was characterized as nucleus-exporting signature (NES). However, the cy3-labeled phage were located in HUVEC nuclei, compared with localization of the control phage without the peptide insert on cell membrane or in cytoplasm. Other proteins that contain a Nucleus-Export Sequence (NES) are as follows:

HIV-1 Rev
LPPLERLTLD

HTLV-1 Rex
LSAQLYSSLSLD

HSV-1 ICP27
IDMLIDLGLDLD

EBV Sm
LPSPL-ASLTL

HSV-VP13/14 NES1
LGRVL-DVLAVM

HSV-VP13/14 NES2
LHTAL-ATVTLK

HSV-VP13/14 NES3
LAAGLVLQRLLG

MVM NS2
MTKKFGTLTI

PKI
LALKLAGLDI

MAPKK
LQKKLEELEL

NMD3
LAEMLEDLHI

An3
LDQQFAGLDL

-continued

```
IκBα
MVKELQEIRL

Cyclin B1
LCQAFSDVIL

TFIIIA
LPVLENLTL

Consensus
φX₂₋₃φX₂₋₃φXφ
φ = L, I, V, F or M, residues with large
hydrophobic side chain.
X = any amino acid
```

Engelsma et al., 2004 reported two phage-displayed peptides isolated from an M13 library, S0 and P0, which contained NES-like sequences and localized to the nuclear membrane.

```
S0
LARLFSALSV

P0
LSSLFSGLSV

Consensus
LX2LFX2LSV

Peptide from T7 library
FTHALDPGQLAL
```

REFERENCES

The references listed below as well as all references cited in the specification are incorporated herein by reference to the extent that they supplement, explain, provide a background for or teach methodology, techniques and/or compositions employed herein.

Aboud-Pirak et al. (1989) Biochem Pharmacol 38:641-648.
Albini et al. (2000) Am J Pathol 156:1381-1393.
Alexay et al. (1996) The PCT International Society of Optical Engineering 2705/63
Allen et al. (1995) Trends Biochem Sci 20:511-516.
Altschul et al. (1990) J Mol Biol 215:403-410.
Amemiya et al. (1988) Topics Curr Chem 147:121-144.
Andersson et al. (2000) Biopolymers 55:227-250.
Arap et al. (1998) Science 279:377-380.
Ausubel (1995) *Short Protocols in Molecular Biology*, 3rd ed. Wiley, New York.
Baillie et al. (1995) Br J Cancer 72:257-267.
Barton (1998) Acta Crystallogr D Biol Crystallogr 54:1139-1146.
Batzer et al. (1991) Nucleic Acids Res 19:5081.
Bauminger & Wilchek (1980) Methods Enzymol 70:151-159.
Becerril et al. (Biochem Biophys Res Commun 255:386-393.
Bendixen et al. (1994) Nucleic Acids Res 22:1778-1779.
Bodanszky (1993) *Principles of Peptide Synthesis*, 2nd rev. ed. Springer-Verlag, Berlin/N.Y.
Boerman et al. (2000) Semin Nucl Med 30:195-208.
Brenner & Lerner (1992) Proc Natl Acad Sci USA 89:5381-5383.
Brent & Finley (1997) Annu Rev Genet. 31:663-704.
Buchsbaum et al. (1995) Cancer Res 55:5881s-5887s.
Burg et al. (1999) Cancer Res 59:2869-2874.
Carninci et al. (1996) Genomics 37:327-336.
Carpizo & Iruela-Arispe (2000) Cancer Metastasis Rev 19:159-165.
Chattopadhyay et al. (2001) Nucl Med Biol 28:741-744.
Cheng (1996) Hum Gene Ther 7:275-282.
Cheng et al. (1994) J Med Chem 37:1-8.
Chiu et al. (2000) J Agric Food Chem 48:2614-2624.
Clapp et al. (1993) Endocrinology 133:1292-1299.
Coatney (2001) Ilar J 42:233-247.
Cohen et al. (1998) Proc Natl Acad Sci USA 95:14272-14277.
Corringer et al. (1993) J Med Chem 36:166-172.
Dameron et al. (1994) Science 265:1582-1584.
Deutscher (1990) *Guide to Protein Purification*, Academic Press, San Diego.
Dewanjee et al. (1994) J Nucl Med 35:1054-1063.
Dias et al. (1998) Int J Cancer 75:151-157.
Dillman et al. (1989) Mol Biother 1:250-255.
Donnelly et al. (2001) Radiology 219:166-170.
Eijan et al. (1991) Mol Biother 3:38-40.
Ellerby et al. (1999) Nat Med 5:1032-1038.
Engelsma et al. (2004) EMBO J. 23:3643-52.
European Patent No. 0 439 095
Fields & Noble (1990) Int J Pept Protein Res 35:161-214.
Fjalling et al. (1996) J Nucl Med 37:1519-1521.
Fields & Song (1989) Nature 340:245-246.
Fitzpatrick & Garnett (1995) Anticancer Drug Des 10:1-9.
Fowlkes et al. (1992) Biotechniques 13:422-428.
Fraser (1996) Methods Cell Biol 51:147-160.
Fuller et al. (1998) Biotechniques 25:85-88, 90-82.
Garbay-Jaureguiberry et al. (1992) Int J Pept Protein Res 39:523-527.
Geng et al. (2001) Cancer Res 61:2413-2419.
Glover & Hames (1995) *DNA Cloning: A Practical Approach*, 2nd ed. IRL Press at Oxford University Press, Oxford/N.Y.
Goldman et al. (1997) Cancer Res 57:1447-1451.
Haaparanta & Huse (1995) Mol Divers 1:39-52.
Hallahan & Virudachalam (1999) Radiat Res 152:6-13.
Hallahan et al. (1995a) Biochem Biophys Res Commun 217:784-795.
Hallahan et al. (1995b) Nat Med 1:786-791.
Hallahan et al. (1996) Cancer Res 56:5150-5155.
Hallahan et al. (1998) Cancer Res 58:5216-5220.
Hallahan et al. (2001a) J Control Release 74:183-191.
Hallahan et al. (2001b) Am J Clin Oncol 24:473-480.
Hartmann et al. (1994) Cancer Res 54:4362-4370.
Hawiger & Timmons (1992) Meth Enzymol 215:228-243.
Hawiger et al. (1989) Biochemistry 28:2909-2914.
Healy et al. (1995) Biochemistry 34:3948-3955.
Henikoff et al. (2000) Electrophoresis 21:1700-1706.
Henikoff & Henikoff (1992) Proc Natl Acad Sci USA 89:10915-10919.
Henn et al. (1993) J Med Chem 36:1570-1579.
Heredia et al. (1991) J Neurosci Methods 36:17-25.
Hnatowich et al. (1996) J Pharmacol Exp Ther 276:326-334.
Holzem et al. (2001) J Gen Virol 82:9-15.
Huang et al. (2000) Pac Symp Biocomput: 230-241.
Ingber et al. (1990) Nature 348:555-557.
Ishikawa (1999) *Ultrasensitive and rapid enzyme immunoassay*. Elsevier, Amsterdam/N.Y.
Ito et al. (1991) Cancer Res 51:255-260.
Julien et al. (2000) Biochemistry 39:75-85.
Jung & Pluckthun (1997) Protein Eng 10:959-966.
Karlin & Altschul (1993) Proc Natl Acad Sci USA 90:5873-5877.
Kirk & Mule (2000) Hum Gene Ther 11:797-806.
Kirpotin et al. (1997) Biochemistry 36:66-75.
Koivunen et al. (1993) J Biol Chem 268:20205-20210.
Koivunen et al. (1994) J Cell Biol 124:373-380.

Kolonin & Finley (1998) Proc Natl Acad Sci USA 95:14266-14271.
Kosfeld & Frazier (1993) J Biol Chem 268:8808-8814.
Krauer et al. (1992) Cancer Res 52:132-137.
Krenning & de Jong (2000) Ann Oncol 11:267-271.
Kwekkeboom et al. (2000) J Nucl Med 41:1704-1713.
Kyte & Doolittle (1982) J Mol Biol 157:105-132.
Law (1996) *Immunoassay: A Practical Guide*. Taylor & Francis, London/Bristol, Pa.
Lau et al. (1995) Bioorg Med Chem 3:1299-1304.
Lecrenier et al. (1998) Bioessays 20:1-5.
Lees (2001) Semin Ultrasound CT MR 22:85-105.
Leibel & Phillips (1998) *Textbook of Radiation Oncology*. Saunders, Philadelphia.
Licha et al. (2000) Photochem Photobiol 72:392-398.
Lu et al. (1995) Biotechnology (NY) 13:366-372.
Mackensen et al. (1997) Cytokine Growth Factor Rev 8:119-128.
Maione et al. (1990) Science 247:77-79.
Manome et al. (1994) Cancer Res 54:5408-5413.
Manson (1992) *Immunochemical Protocols*. Humana Press, Totowa, N. J.
Martodam et al. (1979) Proc Natl Acad Sci USA 76:2128-2132.
McOmie (1973) *Protective Groups in Organic Chemistry*, Plenum Press, London, N.Y.
Merrifield (1969) Adv Enzymol Relat Areas Mol Biol 32:221-296.
Nabel (1997) Vectors for Gene Therapy. In: *Current Protocols in Human Genetics*, John Wiley & Sons, New York.
Narvaiza et al. (2000) J Immunol 164:3112-3122.
Needleman & Wunsch (1970) J Mol Biol 48:443-453.
Neri et al. (1997) Nat Biotechnol 15:1271-1275.
Nomura & Hasegawa (2000) Anticancer Res 20:4073-4080.
O'Byrne et al. (2000) Eur J Cancer 36:151-169.
O'Reilly et al. (1994) Cell 79:315-328.
O'Reilly et al. (1997) Cell 88:277-285.
Ohtsuka et al. (1985) J Biol Chem 260:2605-2608.
Park et al. (1997) Adv Pharmacol 40:399-435.
Pasqualini & Ruoslahti (1996) Nature 380:364-366.
Pasqualini et al. (1997) Nat Biotechnol 15:542-546.
Pavone et al. (1993) Int J Pept Protein Res 41:15-20.
PCT International Patent Application Publications WO 93/25521; WO 98/10795; WO 99/54728; and WO 01/09611
Pearson & Lipman (1988) Proc Natl Acad Sci USA 85:2444-2448.
Peter et al. (2000) Circulation 101:1158-1164.
Pierschbacher & Ruoslahti (1987) J Biol Chem 262:17294-17298.
Pomper & Port (2000) Magn Reson Imaging Clin N Am 8:691-713.
Ragnarson et al. (1992) Histochemistry 97:329-333.
Rehrauer et al. (1996) J Biol Chem 271:23865-23873.
Rossolini et al. (1994) Mol Cell Probes 8:91-98.
Rovaris et al. (J Neurol Sci 186 Suppl 1:S3-9.
Rowland et al. (1993) Cancer Immunol Immunother 37:195-202.
Sagiuchi et al. (2001) Ann Nucl Med 15:267-270.
Sakamoto et al. (1991) Cancer Res 51:903-906.
Saltzman & Fung (1997) Adv Drug Deliv Rev 26:209-230.
Sambrook & Russell (2001) *Molecular Cloning: a Laboratory Manual*, 3rd ed. Cold Spring Harbor Laboratory Press, Cold Spring Harbor, N.Y.
Saqi et al. (1999) Bioinformatics 15:521-522.
Schechter et al. (1991) Int J Cancer 48:167-172.
Schneider & Eberle (1993) Peptides, 1992: Proceedings of the Twenty-Second European Peptide Symposium, Sep. 13-19, 1992, Interlaken, Switzerland, Escom, Leiden.
Schröder & Lübke (1965) *The Peptides*, Academic Press, New York.
Schwendener (1992) Chimia 46:69-77.
Shawler et al. (1988) J Biol Response Mod 7:608-618.
Shen et al. (1993) Magn Reson Med 29:599-604.
Shih et al. (1994) Cancer Immunol Immunother 38:92-98.
Silhavy et al. (1984) *Experiments with Gene Fusions*. Cold Spring Harbor Laboratory, Cold Spring Harbor, N. Y.
Sivam et al. (1995) Cancer Res 55:2352-2356.
Smith (1985) Science 228:1315-1317.
Smith & Waterman (1981) Adv Appl Math 2:482-489.
Smyth et al. (1987) Immunol Cell Biol 65:315-321.
Staba et al. (2000) Cancer Gene Ther 7:13-19.
Starling et al. (1992) Bioconjug Chem 3:315-322.
Stewart & Young (1969) *Solid Phase Peptide Synthesis*, Freeman, San Francisco.
Tang & Casey (1999) Biochemistry 38:14565-14572.
Tavitian et al. (1998) Nat Med 4:467-471.
Tijssen (1993) Laboratory Techniques in Biochemistry and Molecular Biology—Hybridization with Nucleic Acid Probes. Elsevier, New York.
Tolsma et al. (1993) J Cell Biol 122:497-511.
Tung et al. (1992) Pept Res 5:115-118.
Urge et al. (1992) Carbohydr Res 235:83-93
U.S. Pat. Nos. 4,235,871; 4,244,946; 4,551,482; 4,554,101; 5,011,634; 5,088,499; 5,147,631; 5,168,037; 5,223,409; 5,234,933; 5,264,563; 5,326,902; 5,490,840; 5,498,538; 5,508,020; 5,510,103; 5,645,815; 5,578,629; 5,574,172; 5,650, 489; 5,651,991; 5,667,988; 5,688,931; 5,702,892; 5,707,605; 5,714,166; 5,738,837; 5,738,996; 5,747,334; 5,756,291; 5,780,225; 5,786,387; 5,811,392; 5,811,512; 5,811,515; 5,817,757; 5,817,879; 5,824,483; 5,830,856; 5,840,479; 5,580,717; 5,851,818; 5,855,900; 5,858,410; 5,858,670; 5,858,784; 5,865,754; 5,922,356; 5,948,635; 5,922,545; 5,928,627; 5,948,767; 5,994,392; 6,013,638; 6,015,561; 6,015,881; 6,022,737; 6,024,938; 6,031,071; 6,083,486; 6,056,938; 6,057,098; 6,068,829; 6,071,890; 6,080,384; 6,106,866; 6,107,059; 6,132,766; 6,136,295; 6,156,511; 6,159,443; 6,168,912; 6,174,708; 6,180,348; 6,197,333; 6,200,598; 6,210,707; 6,214,553; 6,217,886; 6,221,018; 6,225,447; 6,231,834; 6,245,318; 6,246,901; and 6,254,852
Vasavada et al. (1991) Proc Natl Acad Sci USA 88:10686-10690.
Vinogradov et al. (1996) Biophys J 70:1609-1617.
Virgolini et al. (2001) Q J Nucl Med 45:153-159.
Voest et al. (1995) J Natl Cancer Inst 87:581-586.
Walther & Stein (1999) Mol Biotechnol 13:21-28.
Weissleder et al. (1992) Magn Reson Q 8:55-63.
Weissleder et al. (1999) Nat Biotechnol 17:375-378.
Wickham et al. (1995) Gene Ther 2:750-756.
Wilbur (1992) Bioconjug Chem 3:433-470
Woltering et al. (1991) J Surg Res 50:245-251.
Yang et al. (1995) Nucleic Acids Res 23:1152-1156.
Yoo et al. (1997) J Nucl Med 38:294-300.

It will be understood that various details of the presently disclosed subject matter can be changed without departing from the scope of the present disclosure. Furthermore, the foregoing description is for the purpose of illustration only, and not for the purpose of limitation.

What is claimed is:

1. A composition comprising an amino acid sequence Thr-Phe-Phe-Val-Ser-Thr-Arg-His-Asp-Leu-Val-Ile-Cys-Leu (SEQ ID NO 52).

2. The composition of claim 1, wherein the composition further comprises a detectable label, a therapeutic agent, a drug carrier, or combinations thereof.

3. The composition of claim 1, wherein the detectable label is an in vivo detectable label.

4. The composition of claim 3, wherein the in vivo detectable label comprises a radionuclide label selected from the group consisting of $^{131}$I or $^{99m}$Tc.

5. The composition of claim 2, wherein the therapeutic agent is selected from the group consisting of a radionuclide, a cytotoxin, a therapeutic gene, and a chemotherapeutic agent.

6. The composition of claim 2, wherein the drug carrier is selected from the group consisting of a viral vector, a liposome, a plasmid, a microcapsule, and combinations thereof.

7. A method for guided delivery of a therapeutic composition, a diagnostic composition, or a combination thereof, to a tumor in a subject, the method comprising:
   a. exposing the tumor to ionizing radiation; and
   b. administering to the subject a therapeutic composition, a diagnostic composition, or a combination thereof, wherein the therapeutic composition, diagnostic composition, or the combination thereof comprises a composition comprising an amino acid sequence Thr-Phe-Phe-Val-Ser-Thr-Arg-His-Asp-Leu-Val-Ile-Cys-Leu (SEQ ID NO:52); whereby the therapeutic composition, diagnostic composition, or combination thereof is selectively targeted to the tumor.

8. The method of claim 7, wherein the tumor is a primary or a metastasized tumor.

9. The method of claim 7, wherein the tumor is selected from a tumor selected from the group consisting of bladder carcinoma, breast carcinoma, cervical carcinoma, cholangiocarcinoma, colorectal carcinoma, gastric sarcoma, glioma, lung carcinoma, lymphoma, melanoma, multiple myeloma, osteosarcoma, ovarian carcinoma, pancreatic carcinoma, prostate carcinoma, stomach carcinoma, a head tumor, a neck tumor, and a solid tumor.

10. The method of claim 7, wherein the exposing comprises exposing the tumor to at least about 2 Gy ionizing radiation.

11. The method of claim 7, wherein the administering comprises administering the targeting ligand by intravascular provision.

12. The method of claim 7, wherein the administering comprises administering the targeting ligand subsequent to radiation exposure.

13. A method of guided delivery of a therapeutic composition, a diagnostic composition, or a combination thereof, to a nucleus of a cell, the method comprising:
   a. exposing the cell to ionizing radiation; and
   b. contacting the cell with a therapeutic composition, a diagnostic composition, or a combination thereof, wherein the therapeutic composition, diagnostic composition, or the combination thereof comprises a composition comprising an amino acid sequence Thr-Phe-Phe-Val-Ser-Thr-Arg-His-Asp-Leu-Val-Ile-Cys-Leu (SEQ ID NO:52);

whereby the therapeutic composition, diagnostic composition, or combination thereof enters the cell and is selectively targeted to the nucleus of the cell.

* * * * *

SEQUENCE LISTING

<160> NUMBER OF SEQ ID NOS: 56

<210> SEQ ID NO 1
<211> LENGTH: 8
<212> TYPE: PRT
<213> ORGANISM: Artificial Sequence
<220> FEATURE:
<223> OTHER INFORMATION: Artificial peptide ligand number 1

<400> SEQUENCE: 1

Asn His Val Gly Gly Ser Ser Val
1               5

<210> SEQ ID NO 2
<211> LENGTH: 10
<212> TYPE: PRT
<213> ORGANISM: Artificial Sequence
<220> FEATURE:
<223> OTHER INFORMATION: Artificial peptide ligand number 2

<400> SEQUENCE: 2

Asn Ser Leu Arg Gly Asp Gly Ser Ser Val
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Artificial peptide ligand number 3

<400> SEQUENCE: 3

Asn Ser Val Arg Gly Ser Gly Ser Gly Val
1               5                   10

<210> SEQ ID NO 4
<211> LENGTH: 7
<212> TYPE: PRT
<213> ORGANISM: Artificial Sequence
<220> FEATURE:
<223> OTHER INFORMATION: Artificial peptide ligand number 4

<400> SEQUENCE: 4

Asn Ser Val Gly Ser Arg Val
1               5

<210> SEQ ID NO 5
<211> LENGTH: 9
<212> TYPE: PRT
<213> ORGANISM: Artificial Sequence
<220> FEATURE:
<223> OTHER INFORMATION: Artificial peptide ligand number 5

<400> SEQUENCE: 5

Ser Leu Arg Gly Asp Gly Ser Ser Val
1               5

<210> SEQ ID NO 6
<211> LENGTH: 7
<212> TYPE: PRT
<213> ORGANISM: Artificial Sequence
<220> FEATURE:
<223> OTHER INFORMATION: Artificial peptide ligand number 6

<400> SEQUENCE: 6

Arg Gly Asp Gly Ser Ser Val
1               5

```
<210> SEQ ID NO 7
<211> LENGTH: 4
<212> TYPE: PRT
<213> ORGANISM: Artificial Sequence
<220> FEATURE:
<223> OTHER INFORMATION: Artificial peptide ligand number 7

<400> SEQUENCE: 7

Gly Ser Arg Val
1

<210> SEQ ID NO 8
<211> LENGTH: 4
<212> TYPE: PRT
<213> ORGANISM: Artificial Sequence
<220> FEATURE:
<223> OTHER INFORMATION: Artificial peptide ligand number 8
<220> FEATURE:
<221> NAME/KEY: MISC_FEATURE
<222> LOCATION: (3)..(3)
<223> OTHER INFORMATION: Xaa can be any naturally occurring amino acid

<400> SEQUENCE: 8

Gly Ser Xaa Val
1

<210> SEQ ID NO 9
<211> LENGTH: 8
<212> TYPE: PRT
<213> ORGANISM: Artificial Sequence
<220> FEATURE:
<223> OTHER INFORMATION: Artificial peptide ligand number 9
<220> FEATURE:
<221> NAME/KEY: MISC_FEATURE
<222> LOCATION: (3)..(6)
<223> OTHER INFORMATION: Xaa can be any naturally occurring amino acid

<400> SEQUENCE: 9

Asn Ser Xaa Arg Gly Xaa Gly Ser
1               5

<210> SEQ ID NO 10
<211> LENGTH: 3
<212> TYPE: PRT
<213> ORGANISM: Artificial Sequence
<220> FEATURE:
<223> OTHER INFORMATION: Artificial peptide ligand number 10

<400> SEQUENCE: 10

Asn Ser Val
1

<210> SEQ ID NO 11
<211> LENGTH: 4
<212> TYPE: PRT
<213> ORGANISM: Artificial Sequence
<220> FEATURE:
<223> OTHER INFORMATION: Artificial peptide ligand number 11
<220> FEATURE:
<221> NAME/KEY: MISC_FEATURE
<222> LOCATION: (3)..(3)
<223> OTHER INFORMATION: Xaa can be any naturally occurring amino acid

<400> SEQUENCE: 11

Asn Ser Xaa Arg
1
```

```
<210> SEQ ID NO 12
<211> LENGTH: 4
<212> TYPE: PRT
<213> ORGANISM: Artificial Sequence
<220> FEATURE:
<223> OTHER INFORMATION: Artificial peptide ligand number 12
<220> FEATURE:
<221> NAME/KEY: MISC_FEATURE
<222> LOCATION: (2)..(2)
<223> OTHER INFORMATION: Xaa can be any naturally occurring amino acid

<400> SEQUENCE: 12

Asn Xaa Val Gly
1

<210> SEQ ID NO 13
<211> LENGTH: 4
<212> TYPE: PRT
<213> ORGANISM: Artificial Sequence
<220> FEATURE:
<223> OTHER INFORMATION: Artificial peptide ligand number 13

<400> SEQUENCE: 13

Gly Ser Ser Val
1

<210> SEQ ID NO 14
<211> LENGTH: 20
<212> TYPE: DNA
<213> ORGANISM: T7 bacteriophage

<400> SEQUENCE: 14
agcggaccag attatcgcta                                                 20

<210> SEQ ID NO 15
<211> LENGTH: 19
<212> TYPE: DNA
<213> ORGANISM: T7 bacteriophage

<400> SEQUENCE: 15
aaccctcaag acccgttta                                                  19

<210> SEQ ID NO 16
<211> LENGTH: 12
<212> TYPE: PRT
<213> ORGANISM: Artificial Sequence
<220> FEATURE:
<223> OTHER INFORMATION: Artificial peptide ligand number 16

<400> SEQUENCE: 16

His His Cys Gly Gly Ala Lys Gln Ala Gly Asp Val
1               5                   10

<210> SEQ ID NO 17
<211> LENGTH: 726
<212> TYPE: DNA
<213> ORGANISM: Artificial Sequence
<220> FEATURE:
<223> OTHER INFORMATION: Artificial antibody ligand number 1
<220> FEATURE:
<221> NAME/KEY: CDS
<222> LOCATION: (1)..(726)

<400> SEQUENCE: 17 atg gcc cag gtg aaa ctg cag cag tct ggg gct gag ctt gtg atg cct      48
Met Ala Gln Val Lys Leu Gln Gln Ser Gly Ala Glu Leu Val Met Pro
1               5                   10                  15
```

```
ggg gct tca gtg aag atg tcc tgc aag gct tct ggc tac aca ttc act      96
Gly Ala Ser Val Lys Met Ser Cys Lys Ala Ser Gly Tyr Thr Phe Thr
            20                  25                  30 gac tac tgg atg cac tgg gtg aag cag agg cct gga caa ggc ctt gag     144
Asp Tyr Trp Met His Trp Val Lys Gln Arg Pro Gly Gln Gly Leu Glu
        35                  40                  45 tgg atc gga gcg att gat act tct gat agt tat act agc tac aat caa     192
Trp Ile Gly Ala Ile Asp Thr Ser Asp Ser Tyr Thr Ser Tyr Asn Gln
50                  55                  60 aag ttc aag ggc aag gcc aca ttg act gta gac gaa tcc tcc agc aca     240
Lys Phe Lys Gly Lys Ala Thr Leu Thr Val Asp Glu Ser Ser Ser Thr
65                  70                  75                  80 gcc tac atg cag ctc agc agc ctg aca tct gag gac tct gcg gtc tat     288
Ala Tyr Met Gln Leu Ser Ser Leu Thr Ser Glu Asp Ser Ala Val Tyr
                85                  90                  95 tac tgt gca aga aga ggc tac tat agc gca ttt gat tac tgg ggc caa     336
Tyr Cys Ala Arg Arg Gly Tyr Tyr Ser Ala Phe Asp Tyr Trp Gly Gln
            100                 105                 110 ggg act acg gtc acc gtc tcc tca ggt gga ggc ggt tca ggc gga ggt     384
Gly Thr Thr Val Thr Val Ser Ser Gly Gly Gly Gly Ser Gly Gly Gly
        115                 120                 125 ggc tct ggc ggt ggc gga tcg gac att gag ctc acc cag tct cca aca     432
Gly Ser Gly Gly Gly Gly Ser Asp Ile Glu Leu Thr Gln Ser Pro Thr
130                 135                 140 acc atg gct gca tct cca gga gag aag gtc acc atc acc tgc cgt gcc     480
Thr Met Ala Ala Ser Pro Gly Glu Lys Val Thr Ile Thr Cys Arg Ala
145                 150                 155                 160 agc tca agt gta agc tac atg cac tgg ttc cag cag aag tca ggc acc     528
Ser Ser Ser Val Ser Tyr Met His Trp Phe Gln Gln Lys Ser Gly Thr
                165                 170                 175 tcc ccc aaa ccc tgg att tat gac aca tcc aag ctg gct tct gga gtc     576
Ser Pro Lys Pro Trp Ile Tyr Asp Thr Ser Lys Leu Ala Ser Gly Val
            180                 185                 190 cca gat cgc ttc agt ggc agt ggg tct ggg acc tct tat tct ctc aca     624
Pro Asp Arg Phe Ser Gly Ser Gly Ser Gly Thr Ser Tyr Ser Leu Thr
        195                 200                 205 atc agc tcc atg gag gct gaa gat gct gct act tat tac tgt ctg cag     672
Ile Ser Ser Met Glu Ala Glu Asp Ala Ala Thr Tyr Tyr Cys Leu Gln
210                 215                 220 agg agt agt tac ccg tac acg ttt gga gct ggc acc aag ctg gaa atc     720
Arg Ser Ser Tyr Pro Tyr Thr Phe Gly Ala Gly Thr Lys Leu Glu Ile
225                 230                 235                 240 aaa cgg                                                             726
Lys Arg

<210> SEQ ID NO 18
<211> LENGTH: 242
<212> TYPE: PRT
<213> ORGANISM: Artificial Sequence
<220> FEATURE:
<223> OTHER INFORMATION: Synthetic Construct

<400> SEQUENCE: 18

Met Ala Gln Val Lys Leu Gln Gln Ser Gly Ala Glu Leu Val Met Pro
1               5                   10                  15

Gly Ala Ser Val Lys Met Ser Cys Lys Ala Ser Gly Tyr Thr Phe Thr
            20                  25                  30

Asp Tyr Trp Met His Trp Val Lys Gln Arg Pro Gly Gln Gly Leu Glu
        35                  40                  45

Trp Ile Gly Ala Ile Asp Thr Ser Asp Ser Tyr Thr Ser Tyr Asn Gln
```

```
                    50                  55                  60
Lys Phe Lys Gly Lys Ala Thr Leu Thr Val Asp Glu Ser Ser Thr
 65                  70                  75                  80

Ala Tyr Met Gln Leu Ser Ser Leu Thr Ser Glu Asp Ser Ala Val Tyr
                 85                  90                  95

Tyr Cys Ala Arg Arg Gly Tyr Tyr Ser Ala Phe Asp Tyr Trp Gly Gln
            100                 105                 110

Gly Thr Thr Val Thr Val Ser Ser Gly Gly Gly Gly Ser Gly Gly Gly
                115                 120                 125

Gly Ser Gly Gly Gly Ser Asp Ile Glu Leu Thr Gln Ser Pro Thr
        130                 135                 140

Thr Met Ala Ala Ser Pro Gly Glu Lys Val Thr Ile Thr Cys Arg Ala
145                 150                 155                 160

Ser Ser Ser Val Ser Tyr Met His Trp Phe Gln Gln Lys Ser Gly Thr
                165                 170                 175

Ser Pro Lys Pro Trp Ile Tyr Asp Thr Ser Lys Leu Ala Ser Gly Val
            180                 185                 190

Pro Asp Arg Phe Ser Gly Ser Gly Ser Gly Thr Ser Tyr Ser Leu Thr
            195                 200                 205

Ile Ser Ser Met Glu Ala Glu Asp Ala Ala Thr Tyr Tyr Cys Leu Gln
        210                 215                 220

Arg Ser Ser Tyr Pro Tyr Thr Phe Gly Ala Gly Thr Lys Leu Glu Ile
225                 230                 235                 240

Lys Arg

<210> SEQ ID NO 19
<211> LENGTH: 726
<212> TYPE: DNA
<213> ORGANISM: Artificial Sequence
<220> FEATURE:
<223> OTHER INFORMATION: Artificial antibody ligand number 2
<220> FEATURE:
<221> NAME/KEY: CDS
<222> LOCATION: (1)..(726)

<400> SEQUENCE: 19 atg gcc cag gtc aag ctg cag cag tca gga cct gag ctg gta aag cct      48
Met Ala Gln Val Lys Leu Gln Gln Ser Gly Pro Glu Leu Val Lys Pro
  1               5                  10                  15 ggg gct tca gtg aag atg tcc tgc aag gct tct gga tac aca ttc act      96
Gly Ala Ser Val Lys Met Ser Cys Lys Ala Ser Gly Tyr Thr Phe Thr
                 20                  25                  30 agc tat gtt atg cac tgg gtg aag cag aag cct ggg cag ggc ctt gag     144
Ser Tyr Val Met His Trp Val Lys Gln Lys Pro Gly Gln Gly Leu Glu
             35                  40                  45 tgg att gga tat att aat cct tac aat gat ggt act aag tac aat gag     192
Trp Ile Gly Tyr Ile Asn Pro Tyr Asn Asp Gly Thr Lys Tyr Asn Glu
         50                  55                  60 aag ttc aaa ggc aag gcc gca ctg act tca gac aaa tcc tcc agc aca     240
Lys Phe Lys Gly Lys Ala Ala Leu Thr Ser Asp Lys Ser Ser Ser Thr
 65                  70                  75                  80 gcc tac atg gag ctc agc agc ctg acc tct gag gac tct gcg gtc tat     288
Ala Tyr Met Glu Leu Ser Ser Leu Thr Ser Glu Asp Ser Ala Val Tyr
                 85                  90                  95 tac tgt gca aga ttt ggt aac tac ggt gct ttg gac tac tgg ggc caa     336
Tyr Cys Ala Arg Phe Gly Asn Tyr Gly Ala Leu Asp Tyr Trp Gly Gln
            100                 105                 110 ggg acc acg gtc acc gtc tcc tca ggt gga ggc ggt tca ggc gga ggt     384
Gly Thr Thr Val Thr Val Ser Ser Gly Gly Gly Gly Ser Gly Gly Gly
```

```
Gly Thr Thr Val Thr Val Ser Gly Gly Gly Ser Gly Gly Gly
            115                 120                 125 ggc tct ggc ggt ggc gga tcg gac att gag ctc acc cag tct cca aca       432
Gly Ser Gly Gly Gly Gly Ser Asp Ile Glu Leu Thr Gln Ser Pro Thr
        130                 135                 140 atc atg tct gca tct cca ggg gag aag gtc acc ata acc tgc agt gcc       480
Ile Met Ser Ala Ser Pro Gly Glu Lys Val Thr Ile Thr Cys Ser Ala
145                 150                 155                 160 agc tca agt gta agt tac atg cac tgg ttc cag cag aag cca ggc act       528
Ser Ser Ser Val Ser Tyr Met His Trp Phe Gln Gln Lys Pro Gly Thr
                165                 170                 175 tct ccc aaa ccc tgg att tat ggc aca tcc aac ctg gct tct gga gtc       576
Ser Pro Lys Pro Trp Ile Tyr Gly Thr Ser Asn Leu Ala Ser Gly Val
            180                 185                 190 cct gtt cgc ttc agt ggc agt gga tct ggg acc tct tat tct ctc aca       624
Pro Val Arg Phe Ser Gly Ser Gly Ser Gly Thr Ser Tyr Ser Leu Thr
        195                 200                 205 atc agc agc atg gag gct gaa gat gct gcc act tat tac tgt caa cag       672
Ile Ser Ser Met Glu Ala Glu Asp Ala Ala Thr Tyr Tyr Cys Gln Gln
210                 215                 220 tgg agt agt tac cca ctc acg ttc gga ggg ggg acc aag ctg gaa ata       720
Trp Ser Ser Tyr Pro Leu Thr Phe Gly Gly Gly Thr Lys Leu Glu Ile
225                 230                 235                 240 aaa cgg                                                                726
Lys Arg <210> SEQ ID NO 20
<211> LENGTH: 242
<212> TYPE: PRT
<213> ORGANISM: Artificial Sequence
<220> FEATURE:
<223> OTHER INFORMATION: Synthetic Construct

<400> SEQUENCE: 20

Met Ala Gln Val Lys Leu Gln Gln Ser Gly Pro Glu Leu Val Lys Pro
1               5                   10                  15

Gly Ala Ser Val Lys Met Ser Cys Lys Ala Ser Gly Tyr Thr Phe Thr
            20                  25                  30

Ser Tyr Val Met His Trp Val Lys Gln Lys Pro Gly Gln Gly Leu Glu
        35                  40                  45

Trp Ile Gly Tyr Ile Asn Pro Tyr Asn Asp Gly Thr Lys Tyr Asn Glu
    50                  55                  60

Lys Phe Lys Gly Lys Ala Ala Leu Thr Ser Asp Lys Ser Ser Ser Thr
65                  70                  75                  80

Ala Tyr Met Glu Leu Ser Ser Leu Thr Ser Glu Asp Ser Ala Val Tyr
                85                  90                  95

Tyr Cys Ala Arg Phe Gly Asn Tyr Gly Ala Leu Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Asp Ile Glu Leu Thr Gln Ser Pro Thr
    130                 135                 140

Ile Met Ser Ala Ser Pro Gly Glu Lys Val Thr Ile Thr Cys Ser Ala
145                 150                 155                 160

Ser Ser Ser Val Ser Tyr Met His Trp Phe Gln Gln Lys Pro Gly Thr
                165                 170                 175

Ser Pro Lys Pro Trp Ile Tyr Gly Thr Ser Asn Leu Ala Ser Gly Val
            180                 185                 190
```

```
Pro Val Arg Phe Ser Gly Ser Gly Ser Gly Thr Ser Tyr Ser Leu Thr
        195                 200                 205

Ile Ser Ser Met Glu Ala Glu Asp Ala Ala Thr Tyr Tyr Cys Gln Gln
    210                 215                 220

Trp Ser Ser Tyr Pro Leu Thr Phe Gly Gly Gly Thr Lys Leu Glu Ile
225                 230                 235                 240

Lys Arg

<210> SEQ ID NO 21
<211> LENGTH: 7
<212> TYPE: PRT
<213> ORGANISM: Artificial Sequence
<220> FEATURE:
<223> OTHER INFORMATION: Artifical peptide ligand 2.1

<400> SEQUENCE: 21

His Val Gly Gly Ser Ser Val
1               5

<210> SEQ ID NO 22
<211> LENGTH: 9
<212> TYPE: PRT
<213> ORGANISM: Artificial Sequence
<220> FEATURE:
<223> OTHER INFORMATION: Artificial peptide ligand 2.2

<400> SEQUENCE: 22

Ser Val Arg Gly Ser Gly Ser Gly Val
1               5

<210> SEQ ID NO 23
<211> LENGTH: 9
<212> TYPE: PRT
<213> ORGANISM: Artificial Sequence
<220> FEATURE:
<223> OTHER INFORMATION: Artificial peptide ligand 2.3

<400> SEQUENCE: 23

Ser Val Val Arg Asp Gly Ser Glu Val
1               5

<210> SEQ ID NO 24
<211> LENGTH: 11
<212> TYPE: PRT
<213> ORGANISM: Artificial Sequence
<220> FEATURE:
<223> OTHER INFORMATION: Artificial peptide ligand 2.4

<400> SEQUENCE: 24

Ser Gly Arg Lys Val Gly Ser Gly Ser Ser Val
1               5                   10

<210> SEQ ID NO 25
<211> LENGTH: 9
<212> TYPE: PRT
<213> ORGANISM: Artificial Sequence
<220> FEATURE:
<223> OTHER INFORMATION: Artificial peptide ligand 2.5

<400> SEQUENCE: 25

Ser Leu Arg Gly Asp Gly Ser Ser Val
1               5

<210> SEQ ID NO 26
```

```
<211> LENGTH: 6
<212> TYPE: PRT
<213> ORGANISM: Artificial Sequence
<220> FEATURE:
<223> OTHER INFORMATION: Artificial peptide ligand 2.6

<400> SEQUENCE: 26

Ser Val Gly Ser Arg Val
1               5

<210> SEQ ID NO 27
<211> LENGTH: 20
<212> TYPE: PRT
<213> ORGANISM: Artificial Sequence
<220> FEATURE:
<223> OTHER INFORMATION: Artificial peptide ligand 2.7

<400> SEQUENCE: 27

Thr Arg Arg Ser Tyr Ser Pro Arg His Asn Phe Asn Trp Leu Arg Ile
1               5                   10                  15

Gly Asp Phe Thr
            20

<210> SEQ ID NO 28
<211> LENGTH: 12
<212> TYPE: PRT
<213> ORGANISM: Artificial Sequence
<220> FEATURE:
<223> OTHER INFORMATION: Artificial peptide ligand 2.8

<400> SEQUENCE: 28

Arg Lys Phe Leu Met Thr Thr Arg Tyr Ser Arg Val
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Artificial peptide ligand 2.9

<400> SEQUENCE: 29

His Arg Gly Cys Gly Phe Phe Lys Val Leu
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Artificial peptide ligand 2.10

<400> SEQUENCE: 30

Cys Asp Tyr Gln Ile Tyr Gln Asn Val Phe Asn Phe
1               5                   10

<210> SEQ ID NO 31
<211> LENGTH: 16
<212> TYPE: PRT
<213> ORGANISM: Artificial Sequence
<220> FEATURE:
<223> OTHER INFORMATION: Artificial peptide ligand 2.11

<400> SEQUENCE: 31

His Leu Ala Arg Asp Ser Gly Leu Cys Ser Ala Val Pro Asp Pro Asp
1               5                   10                  15
```

```
<210> SEQ ID NO 32
<211> LENGTH: 12
<212> TYPE: PRT
<213> ORGANISM: Artificial Sequence
<220> FEATURE:
<223> OTHER INFORMATION: Artificial peptide ligand 2.12

<400> SEQUENCE: 32

Leu Thr Pro Pro Gly Asp Asn Ala Leu Leu Leu Ala
1               5                   10

<210> SEQ ID NO 33
<211> LENGTH: 20
<212> TYPE: PRT
<213> ORGANISM: Artificial Sequence
<220> FEATURE:
<223> OTHER INFORMATION: Artificial peptide ligand 2.13
<220> FEATURE:
<221> NAME/KEY: misc_feature
<222> LOCATION: (6)..(6)
<223> OTHER INFORMATION: Xaa can be any naturally occurring amino acid

<400> SEQUENCE: 33

Tyr Ser Thr Leu Pro Xaa Thr Asn Phe Cys Ala Trp Glu Tyr Thr Ala
1               5                   10                  15

Tyr His His Val
            20

<210> SEQ ID NO 34
<211> LENGTH: 18
<212> TYPE: PRT
<213> ORGANISM: Artificial Sequence
<220> FEATURE:
<223> OTHER INFORMATION: Artificial peptide ligand 2.14

<400> SEQUENCE: 34

Lys Phe Leu Arg Ser Ala Gly Val Lys Pro Arg Asn Gly Lys Trp Tyr
1               5                   10                  15

Asp Ser

<210> SEQ ID NO 35
<211> LENGTH: 20
<212> TYPE: PRT
<213> ORGANISM: Artificial Sequence
<220> FEATURE:
<223> OTHER INFORMATION: Artificial peptide ligand 2.15

<400> SEQUENCE: 35

Lys Gly Val Lys Thr Arg Glu Lys Asn Tyr Thr Pro Arg Met Trp Thr
1               5                   10                  15

Glu Arg Ala Asp
            20

<210> SEQ ID NO 36
<211> LENGTH: 12
<212> TYPE: PRT
<213> ORGANISM: Artificial Sequence
<220> FEATURE:
<223> OTHER INFORMATION: Artificial peptide ligand 2.16

<400> SEQUENCE: 36

Lys Thr Ala Lys Lys Asn Val Phe Phe Cys Ser Val
1               5                   10

<210> SEQ ID NO 37
```

```
<211> LENGTH: 20
<212> TYPE: PRT
<213> ORGANISM: Artificial Sequence
<220> FEATURE:
<223> OTHER INFORMATION: Artificial peptide ligand 2.17

<400> SEQUENCE: 37

Pro Pro Ser Cys Val Tyr Pro Ser Arg Lys Cys Ser Pro Thr Ile Ile
1               5                   10                  15
Thr Phe Ser Gln
            20

<210> SEQ ID NO 38
<211> LENGTH: 12
<212> TYPE: PRT
<213> ORGANISM: Artificial Sequence
<220> FEATURE:
<223> OTHER INFORMATION: Artificial peptide ligand 2.18

<400> SEQUENCE: 38

Leu Ser Ile Val Gly Arg Gln Arg Cys Arg His Val
1               5                   10

<210> SEQ ID NO 39
<211> LENGTH: 16
<212> TYPE: PRT
<213> ORGANISM: Artificial Sequence
<220> FEATURE:
<223> OTHER INFORMATION: Artificial peptide ligand 2.19

<400> SEQUENCE: 39

Glu Arg His Val Ser Thr Gln Pro Leu Leu Lys Glu Ala Asn Ile Lys
1               5                   10                  15

<210> SEQ ID NO 40
<211> LENGTH: 11
<212> TYPE: PRT
<213> ORGANISM: Artificial Sequence
<220> FEATURE:
<223> OTHER INFORMATION: Artificial peptide ligand 2.20

<400> SEQUENCE: 40

Arg Gln Pro Cys Thr Tyr Ile Glu Val Arg Pro
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Artificial peptide ligand 2.21

<400> SEQUENCE: 41

Thr Leu Leu Cys Thr Ile Lys Glu Cys Ser
1               5                   10

<210> SEQ ID NO 42
<211> LENGTH: 13
<212> TYPE: PRT
<213> ORGANISM: Artificial Sequence
<220> FEATURE:
<223> OTHER INFORMATION: Artificial peptide ligand 2.22

<400> SEQUENCE: 42

Asp Val Ala Cys Val Thr Ile Asn Leu Pro Asp Val Cys
1               5                   10
```

```
<210> SEQ ID NO 43
<211> LENGTH: 17
<212> TYPE: PRT
<213> ORGANISM: Artificial Sequence
<220> FEATURE:
<223> OTHER INFORMATION: Artificial peptide ligand 2.23

<400> SEQUENCE: 43

Ile Tyr Pro Cys Arg Pro Asn Thr Ala Leu Asn Asp Tyr Cys Ser Leu
1               5                   10                  15

Tyr

<210> SEQ ID NO 44
<211> LENGTH: 15
<212> TYPE: PRT
<213> ORGANISM: Artificial Sequence
<220> FEATURE:
<223> OTHER INFORMATION: Artificial peptide ligand 2.24

<400> SEQUENCE: 44

Thr Phe Pro Cys Lys Pro Leu Arg His Thr Pro Arg Cys Thr Arg
1               5                   10                  15

<210> SEQ ID NO 45
<211> LENGTH: 18
<212> TYPE: PRT
<213> ORGANISM: Artificial Sequence
<220> FEATURE:
<223> OTHER INFORMATION: Artificial peptide ligand 2.25

<400> SEQUENCE: 45

Gly Leu Phe Cys Thr Ala Thr Ser Pro His Val Thr Arg Ala Cys Lys
1               5                   10                  15

Glu Leu

<210> SEQ ID NO 46
<211> LENGTH: 18
<212> TYPE: PRT
<213> ORGANISM: Artificial Sequence
<220> FEATURE:
<223> OTHER INFORMATION: Artificial peptide ligand 2.26

<400> SEQUENCE: 46

Thr Glu Gln Cys Leu Ile His Lys Ser Met Asn Pro Asn Ser Cys Arg
1               5                   10                  15

Gly Phe

<210> SEQ ID NO 47
<211> LENGTH: 12
<212> TYPE: PRT
<213> ORGANISM: Artificial Sequence
<220> FEATURE:
<223> OTHER INFORMATION: Artificial nuclear targeting peptide 1

<400> SEQUENCE: 47

Phe Thr His Ala Leu Asp Pro Gly Gln Leu Ala Leu
1               5                   10

<210> SEQ ID NO 48
<211> LENGTH: 11
<212> TYPE: PRT
<213> ORGANISM: Artificial Sequence
<220> FEATURE:
<223> OTHER INFORMATION: Artificial nuclear targeting peptide 2
```

```
<400> SEQUENCE: 48

His His Leu Ala Ser Leu Tyr His His Ser Tyr
1               5                   10

<210> SEQ ID NO 49
<211> LENGTH: 16
<212> TYPE: PRT
<213> ORGANISM: Artificial Sequence
<220> FEATURE:
<223> OTHER INFORMATION: Artificial nuclear targeting peptide 3

<400> SEQUENCE: 49

Asn Ala Gln Leu Ser Leu Ser Arg Gly His Leu His Gln Met Ile Gln
1               5                   10                  15

<210> SEQ ID NO 50
<211> LENGTH: 20
<212> TYPE: PRT
<213> ORGANISM: Artificial Sequence
<220> FEATURE:
<223> OTHER INFORMATION: Artificial nuclear targeting peptide 4

<400> SEQUENCE: 50

Lys Ala Arg Leu Pro Pro Glu Pro Ser Phe Thr Val Phe Thr Cys Gly
1               5                   10                  15

Arg Ala Ser Ala
            20

<210> SEQ ID NO 51
<211> LENGTH: 20
<212> TYPE: PRT
<213> ORGANISM: Artificial Sequence
<220> FEATURE:
<223> OTHER INFORMATION: Artificial nuclear targeting peptide 5

<400> SEQUENCE: 51

Leu Ser Pro Gln Arg Phe Cys Tyr Gly Tyr Leu Phe Gln Phe Thr Leu
1               5                   10                  15

Val Leu His Leu
            20

<210> SEQ ID NO 52
<211> LENGTH: 14
<212> TYPE: PRT
<213> ORGANISM: Artificial Sequence
<220> FEATURE:
<223> OTHER INFORMATION: Artificial nuclear targeting peptide 6

<400> SEQUENCE: 52

Thr Phe Phe Val Ser Thr Arg His Asp Leu Val Ile Cys Leu
1               5                   10

<210> SEQ ID NO 53
<211> LENGTH: 11
<212> TYPE: PRT
<213> ORGANISM: Artificial Sequence
<220> FEATURE:
<223> OTHER INFORMATION: Artificial nuclear targeting peptide 7

<400> SEQUENCE: 53

Met His Val Glu Arg Val Thr Arg Leu His Thr
1               5                   10

<210> SEQ ID NO 54
<211> LENGTH: 14
```

```
<212> TYPE: PRT
<213> ORGANISM: Artificial Sequence
<220> FEATURE:
<223> OTHER INFORMATION: Artificial nuclear targeting peptide 8

<400> SEQUENCE: 54

Pro His Phe Cys Pro Ala Met Lys Leu Ala Ala Ala Leu Glu
1               5                   10

<210> SEQ ID NO 55
<211> LENGTH: 20
<212> TYPE: PRT
<213> ORGANISM: Artificial Sequence
<220> FEATURE:
<223> OTHER INFORMATION: Artificial nuclear targeting peptide 9

<400> SEQUENCE: 55

His Arg Leu Ser Arg Tyr Arg Pro Arg Leu Gly Pro Tyr Phe Cys Pro
1               5                   10                  15

Ser Pro Glu Val
            20

<210> SEQ ID NO 56
<211> LENGTH: 4391
<212> TYPE: PRT
<213> ORGANISM: Homo sapiens
<300> PUBLICATION INFORMATION:
<308> DATABASE ACCESSION NUMBER: P98160
<309> DATABASE ENTRY DATE: 2003-02-28
<313> RELEVANT RESIDUES IN SEQ ID NO: (1)..(4391)

<400> SEQUENCE: 56

Met Gly Trp Arg Ala Pro Gly Ala Leu Leu Ala Leu Leu Leu His
1               5                   10                  15

Gly Arg Leu Leu Ala Val Thr His Gly Leu Arg Ala Tyr Asp Gly Leu
            20                  25                  30

Ser Leu Pro Glu Asp Ile Glu Thr Val Thr Ala Ser Gln Met Arg Trp
        35                  40                  45

Thr His Ser Tyr Leu Ser Asp Asp Glu Asp Met Leu Ala Asp Ser Ile
    50                  55                  60

Ser Gly Asp Asp Leu Gly Ser Gly Asp Leu Gly Ser Gly Asp Phe Gln
65                  70                  75                  80

Met Val Tyr Phe Arg Ala Leu Val Asn Phe Thr Arg Ser Ile Glu Tyr
                85                  90                  95

Ser Pro Gln Leu Glu Asp Ala Gly Ser Arg Glu Phe Arg Glu Val Ser
            100                 105                 110

Glu Ala Val Val Asp Thr Leu Glu Ser Glu Tyr Leu Lys Ile Pro Gly
        115                 120                 125

Asp Gln Val Val Ser Val Val Phe Ile Lys Glu Leu Asp Gly Trp Val
    130                 135                 140

Phe Val Glu Leu Asp Val Gly Ser Glu Gly Asn Ala Asp Gly Ala Gln
145                 150                 155                 160

Ile Gln Glu Met Leu Leu Arg Val Ile Ser Ser Gly Ser Val Ala Ser
                165                 170                 175

Tyr Val Thr Ser Pro Gln Gly Phe Gln Phe Arg Arg Leu Gly Thr Val
            180                 185                 190

Pro Gln Phe Pro Arg Ala Cys Thr Glu Ala Glu Phe Ala Cys His Ser
        195                 200                 205

Tyr Asn Glu Cys Val Ala Leu Glu Tyr Arg Cys Asp Arg Arg Pro Asp
    210                 215                 220
```

```
Cys Arg Asp Met Ser Asp Glu Leu Asn Cys Glu Glu Pro Val Leu Gly
225                 230                 235                 240

Ile Ser Pro Thr Phe Ser Leu Leu Val Glu Thr Thr Ser Leu Pro Pro
            245                 250                 255

Arg Pro Glu Thr Thr Ile Met Arg Gln Pro Pro Val Thr His Ala Pro
            260                 265                 270

Gln Pro Leu Leu Pro Gly Ser Val Arg Pro Leu Pro Cys Gly Pro Gln
            275                 280                 285

Glu Ala Ala Cys Arg Asn Gly His Cys Ile Pro Arg Asp Tyr Leu Cys
            290                 295                 300

Asp Gly Gln Glu Asp Cys Glu Asp Gly Ser Asp Glu Leu Asp Cys Gly
305                 310                 315                 320

Pro Pro Pro Pro Cys Glu Pro Asn Glu Phe Pro Cys Gly Asn Gly His
                325                 330                 335

Cys Ala Leu Lys Leu Trp Arg Cys Asp Gly Asp Phe Asp Cys Glu Asp
            340                 345                 350

Arg Thr Asp Glu Ala Asn Cys Pro Thr Lys Arg Pro Glu Glu Val Cys
            355                 360                 365

Gly Pro Thr Gln Phe Arg Cys Val Ser Thr Asn Met Cys Ile Pro Ala
370                 375                 380

Ser Phe His Cys Asp Glu Glu Ser Asp Cys Pro Asp Arg Ser Asp Glu
385                 390                 395                 400

Phe Gly Cys Met Pro Pro Gln Val Val Thr Pro Pro Arg Glu Ser Ile
                405                 410                 415

Gln Ala Ser Arg Gly Gln Thr Val Thr Phe Thr Cys Val Ala Ile Gly
            420                 425                 430

Val Pro Thr Pro Ile Ile Asn Trp Arg Leu Asn Trp Gly His Ile Pro
            435                 440                 445

Ser His Pro Arg Val Thr Val Thr Ser Glu Gly Gly Arg Gly Thr Leu
            450                 455                 460

Ile Ile Arg Asp Val Lys Glu Ser Asp Gln Gly Ala Tyr Thr Cys Glu
465                 470                 475                 480

Ala Met Asn Ala Arg Gly Met Val Phe Gly Ile Pro Asp Gly Val Leu
                485                 490                 495

Glu Leu Val Pro Gln Arg Gly Pro Cys Pro Asp Gly His Phe Tyr Leu
            500                 505                 510

Glu His Ser Ala Ala Cys Leu Pro Cys Phe Cys Phe Gly Ile Thr Ser
            515                 520                 525

Val Cys Gln Ser Thr Arg Arg Phe Arg Asp Gln Ile Arg Leu Arg Phe
530                 535                 540

Asp Gln Pro Asp Asp Phe Lys Gly Val Asn Val Thr Met Pro Ala Gln
545                 550                 555                 560

Pro Gly Thr Pro Pro Leu Ser Ser Thr Gln Leu Gln Ile Asp Pro Ser
                565                 570                 575

Leu His Glu Phe Gln Leu Val Asp Leu Ser Arg Arg Phe Leu Val His
            580                 585                 590

Asp Ser Phe Trp Ala Leu Pro Glu Gln Phe Leu Gly Asn Lys Val Asp
            595                 600                 605

Ser Tyr Gly Gly Ser Leu Arg Tyr Asn Val Arg Tyr Glu Leu Ala Arg
            610                 615                 620

Gly Met Leu Glu Pro Val Gln Arg Pro Asp Val Val Leu Val Gly Ala
625                 630                 635                 640
```

-continued

```
Gly Tyr Arg Leu Leu Ser Arg Gly His Thr Pro Thr Gln Pro Gly Ala
                645                 650                 655

Leu Asn Gln Arg Gln Val Gln Phe Ser Glu Glu His Trp Val His Glu
        660                 665                 670

Ser Gly Arg Pro Val Gln Arg Ala Glu Leu Leu Gln Val Leu Gln Ser
    675                 680                 685

Leu Glu Ala Val Leu Ile Gln Thr Val Tyr Asn Thr Lys Met Ala Ser
690                 695                 700

Val Gly Leu Ser Asp Ile Ala Met Asp Thr Val Thr His Ala Thr
705                 710                 715                 720

Ser His Gly Arg Ala His Ser Val Glu Glu Cys Arg Cys Pro Ile Gly
                725                 730                 735

Tyr Ser Gly Leu Ser Cys Glu Ser Cys Asp Ala His Phe Thr Arg Val
            740                 745                 750

Pro Gly Gly Pro Tyr Leu Gly Thr Cys Ser Gly Cys Ser Cys Asn Gly
        755                 760                 765

His Ala Ser Ser Cys Asp Pro Val Tyr Gly His Cys Leu Asn Cys Gln
    770                 775                 780

His Asn Thr Glu Gly Pro Gln Cys Asn Lys Cys Lys Ala Gly Phe Phe
785                 790                 795                 800

Gly Asp Ala Met Lys Ala Thr Ala Thr Ser Cys Arg Pro Cys Pro Cys
                805                 810                 815

Pro Tyr Ile Asp Ala Ser Arg Arg Phe Ser Asp Thr Cys Phe Leu Asp
            820                 825                 830

Thr Asp Gly Gln Ala Thr Cys Asp Ala Cys Ala Pro Gly Tyr Thr Gly
        835                 840                 845

Arg Arg Cys Glu Ser Cys Ala Pro Gly Tyr Glu Gly Asn Pro Ile Gln
    850                 855                 860

Pro Gly Gly Lys Cys Arg Pro Val Asn Gln Glu Ile Val Arg Cys Asp
865                 870                 875                 880

Glu Arg Gly Ser Met Gly Thr Ser Gly Glu Ala Cys Arg Cys Lys Asn
                885                 890                 895

Asn Val Val Gly Arg Leu Cys Asn Glu Cys Ala Asp Gly Ser Phe His
            900                 905                 910

Leu Ser Thr Arg Asn Pro Asp Gly Cys Leu Lys Cys Phe Cys Met Gly
        915                 920                 925

Val Ser Arg His Cys Thr Ser Ser Ser Trp Ser Arg Ala Gln Leu His
    930                 935                 940

Gly Ala Ser Glu Glu Pro Gly His Phe Ser Leu Thr Asn Ala Ala Ser
945                 950                 955                 960

Thr His Thr Thr Asn Glu Gly Ile Phe Ser Pro Thr Pro Gly Glu Leu
                965                 970                 975

Gly Phe Ser Ser Phe His Arg Leu Leu Ser Gly Pro Tyr Phe Trp Ser
            980                 985                 990

Leu Pro Ser Arg Phe Leu Gly Asp Lys Val Thr Ser Tyr Gly Gly Glu
        995                 1000                1005

Leu Arg Phe Thr Val Thr Gln Arg Ser Gln Pro Gly Ser Thr Pro
    1010                1015                1020

Leu His Gly Gln Pro Leu Val Val Leu Gln Gly Asn Asn Ile Ile
    1025                1030                1035

Leu Glu His His Val Ala Gln Glu Pro Ser Pro Gly Gln Pro Ser
    1040                1045                1050

Thr Phe Ile Val Pro Phe Arg Glu Gln Ala Trp Gln Arg Pro Asp
```

-continued

|   |   |   |   |   |   |   |   |   |   |   |   |   |   |   |
|---|---|---|---|---|---|---|---|---|---|---|---|---|---|---|
|   |   |   |   | 1055 |   |   |   |   | 1060 |   |   |   |   | 1065 |
| Gly | Gln | Pro | Ala | Thr | Arg | Glu | His | Leu | Leu | Met | Ala | Leu | Ala | Gly |
|   |   |   | 1070 |   |   |   |   | 1075 |   |   |   |   | 1080 |   |
| Ile | Asp | Thr | Leu | Leu | Ile | Arg | Ala | Ser | Tyr | Ala | Gln | Gln | Pro | Ala |
|   |   | 1085 |   |   |   |   | 1090 |   |   |   |   | 1095 |   |   |
| Glu | Ser | Arg | Val | Ser | Gly | Ile | Ser | Met | Asp | Val | Ala | Val | Pro | Glu |
|   |   | 1100 |   |   |   |   | 1105 |   |   |   |   | 1110 |   |   |
| Glu | Thr | Gly | Gln | Asp | Pro | Ala | Leu | Glu | Val | Glu | Gln | Cys | Ser | Cys |
|   |   | 1115 |   |   |   |   | 1120 |   |   |   |   | 1125 |   |   |
| Pro | Pro | Gly | Tyr | Arg | Gly | Pro | Ser | Cys | Gln | Asp | Cys | Asp | Thr | Gly |
|   |   | 1130 |   |   |   |   | 1135 |   |   |   |   | 1140 |   |   |
| Tyr | Thr | Arg | Thr | Pro | Ser | Gly | Leu | Tyr | Leu | Gly | Thr | Cys | Glu | Arg |
|   |   | 1145 |   |   |   |   | 1150 |   |   |   |   | 1155 |   |   |
| Cys | Ser | Cys | His | Gly | His | Ser | Glu | Ala | Cys | Glu | Pro | Glu | Thr | Gly |
|   |   | 1160 |   |   |   |   | 1165 |   |   |   |   | 1170 |   |   |
| Ala | Cys | Gln | Gly | Cys | Gln | His | His | Thr | Glu | Gly | Pro | Arg | Cys | Glu |
|   |   | 1175 |   |   |   |   | 1180 |   |   |   |   | 1185 |   |   |
| Gln | Cys | Gln | Pro | Gly | Tyr | Tyr | Gly | Asp | Ala | Gln | Arg | Gly | Thr | Pro |
|   |   | 1190 |   |   |   |   | 1195 |   |   |   |   | 1200 |   |   |
| Gln | Asp | Cys | Gln | Leu | Cys | Pro | Cys | Tyr | Gly | Asp | Pro | Ala | Ala | Gly |
|   |   | 1205 |   |   |   |   | 1210 |   |   |   |   | 1215 |   |   |
| Gln | Ala | Ala | His | Thr | Cys | Phe | Leu | Asp | Thr | Asp | Gly | His | Pro | Thr |
|   |   | 1220 |   |   |   |   | 1225 |   |   |   |   | 1230 |   |   |
| Cys | Asp | Ala | Cys | Ser | Pro | Gly | His | Ser | Gly | Arg | His | Cys | Glu | Arg |
|   |   | 1235 |   |   |   |   | 1240 |   |   |   |   | 1245 |   |   |
| Cys | Ala | Pro | Gly | Tyr | Tyr | Gly | Asn | Pro | Ser | Gln | Gly | Gln | Pro | Cys |
|   |   | 1250 |   |   |   |   | 1255 |   |   |   |   | 1260 |   |   |
| Gln | Arg | Asp | Ser | Gln | Val | Pro | Gly | Pro | Ile | Gly | Cys | Asn | Cys | Asp |
|   |   | 1265 |   |   |   |   | 1270 |   |   |   |   | 1275 |   |   |
| Pro | Gln | Gly | Ser | Val | Ser | Ser | Gln | Cys | Asp | Ala | Ala | Gly | Gln | Cys |
|   |   | 1280 |   |   |   |   | 1285 |   |   |   |   | 1290 |   |   |
| Gln | Cys | Lys | Ala | Gln | Val | Glu | Gly | Leu | Thr | Cys | Ser | His | Cys | Arg |
|   |   | 1295 |   |   |   |   | 1300 |   |   |   |   | 1305 |   |   |
| Pro | His | His | Phe | His | Leu | Ser | Ala | Ser | Asn | Pro | Asp | Gly | Cys | Leu |
|   |   | 1310 |   |   |   |   | 1315 |   |   |   |   | 1320 |   |   |
| Pro | Cys | Phe | Cys | Met | Gly | Ile | Thr | Gln | Gln | Cys | Ala | Ser | Ser | Ala |
|   |   | 1325 |   |   |   |   | 1330 |   |   |   |   | 1335 |   |   |
| Tyr | Thr | Arg | His | Leu | Ile | Ser | Thr | His | Phe | Ala | Pro | Gly | Asp | Phe |
|   |   | 1340 |   |   |   |   | 1345 |   |   |   |   | 1350 |   |   |
| Gln | Gly | Phe | Ala | Leu | Val | Asn | Pro | Gln | Arg | Asn | Ser | Arg | Leu | Thr |
|   |   | 1355 |   |   |   |   | 1360 |   |   |   |   | 1365 |   |   |
| Gly | Glu | Phe | Thr | Val | Glu | Pro | Val | Pro | Glu | Gly | Ala | Gln | Leu | Ser |
|   |   | 1370 |   |   |   |   | 1375 |   |   |   |   | 1380 |   |   |
| Phe | Gly | Asn | Phe | Ala | Gln | Leu | Gly | His | Glu | Ser | Phe | Tyr | Trp | Gln |
|   |   | 1385 |   |   |   |   | 1390 |   |   |   |   | 1395 |   |   |
| Leu | Pro | Glu | Thr | Tyr | Gln | Gly | Asp | Lys | Val | Ala | Ala | Tyr | Gly | Gly |
|   |   | 1400 |   |   |   |   | 1405 |   |   |   |   | 1410 |   |   |
| Lys | Leu | Arg | Tyr | Thr | Leu | Ser | Tyr | Thr | Ala | Gly | Pro | Gln | Gly | Ser |
|   |   | 1415 |   |   |   |   | 1420 |   |   |   |   | 1425 |   |   |
| Pro | Leu | Ser | Asp | Pro | Asp | Val | Gln | Ile | Thr | Gly | Asn | Asn | Ile | Met |
|   |   | 1430 |   |   |   |   | 1435 |   |   |   |   | 1440 |   |   |
| Leu | Val | Ala | Ser | Gln | Pro | Ala | Leu | Gln | Gly | Pro | Glu | Arg | Arg | Ser |
|   |   | 1445 |   |   |   |   | 1450 |   |   |   |   | 1455 |   |   |

```
Tyr Glu Ile Met Phe Arg Glu Glu Phe Trp Arg Pro Asp Gly
    1460            1465            1470

Gln Pro Ala Thr Arg Glu His Leu Leu Met Ala Leu Ala Asp Leu
1475            1480            1485

Asp Glu Leu Leu Ile Arg Ala Thr Phe Ser Ser Val Pro Leu Val
    1490            1495            1500

Ala Ser Ile Ser Ala Val Ser Leu Glu Val Ala Gln Pro Gly Pro
1505            1510            1515

Ser Asn Arg Pro Arg Ala Leu Glu Val Glu Glu Cys Arg Cys Pro
    1520            1525            1530

Pro Gly Tyr Ile Gly Leu Ser Cys Gln Asp Cys Ala Pro Gly Tyr
1535            1540            1545

Thr Arg Thr Gly Ser Gly Leu Tyr Leu Gly His Cys Glu Leu Cys
    1550            1555            1560

Glu Cys Asn Gly His Ser Asp Leu Cys His Pro Glu Thr Gly Ala
1565            1570            1575

Cys Ser Gln Cys Gln His Asn Ala Ala Gly Glu Phe Cys Glu Leu
    1580            1585            1590

Cys Ala Pro Gly Tyr Tyr Gly Asp Ala Thr Ala Gly Thr Pro Glu
1595            1600            1605

Asp Cys Gln Pro Cys Ala Cys Pro Leu Thr Asn Pro Glu Asn Met
    1610            1615            1620

Phe Ser Arg Thr Cys Glu Ser Leu Gly Ala Gly Gly Tyr Arg Cys
1625            1630            1635

Thr Ala Cys Glu Pro Gly Tyr Thr Gly Gln Tyr Cys Glu Gln Cys
    1640            1645            1650

Gly Pro Gly Tyr Val Gly Asn Pro Ser Val Gln Gly Gly Gln Cys
1655            1660            1665

Leu Pro Glu Thr Asn Gln Ala Pro Leu Val Val Glu Val His Pro
    1670            1675            1680

Ala Arg Ser Ile Val Pro Gln Gly Gly Ser His Ser Leu Arg Cys
1685            1690            1695

Gln Val Ser Gly Ser Pro Pro His Tyr Phe Tyr Trp Ser Arg Glu
    1700            1705            1710

Asp Gly Arg Pro Val Pro Ser Gly Thr Gln Gln Arg His Gln Gly
    1715            1720            1725

Ser Glu Leu His Phe Pro Ser Val Gln Pro Ser Asp Ala Gly Val
    1730            1735            1740

Tyr Ile Cys Thr Cys Arg Asn Leu His Gln Ser Asn Thr Ser Arg
    1745            1750            1755

Ala Glu Leu Leu Val Thr Glu Ala Pro Ser Lys Pro Ile Thr Val
    1760            1765            1770

Thr Val Glu Glu Gln Arg Ser Gln Ser Val Arg Pro Gly Ala Asp
    1775            1780            1785

Val Thr Phe Ile Cys Thr Ala Lys Ser Lys Ser Pro Ala Tyr Thr
    1790            1795            1800

Leu Val Trp Thr Arg Leu His Asn Gly Lys Leu Pro Thr Arg Ala
    1805            1810            1815

Met Asp Phe Asn Gly Ile Leu Thr Ile Arg Asn Val Gln Leu Ser
    1820            1825            1830

Asp Ala Gly Thr Tyr Val Cys Thr Gly Ser Asn Met Phe Ala Met
    1835            1840            1845
```

```
Asp Gln Gly Thr Ala Thr Leu His Val Gln Ala Ser Gly Thr Leu
1850                1855                1860

Ser Ala Pro Val Val Ser Ile His Pro Pro Gln Leu Thr Val Gln
1865                1870                1875

Pro Gly Gln Leu Ala Glu Phe Arg Cys Ser Ala Thr Gly Ser Pro
1880                1885                1890

Thr Pro Thr Leu Glu Trp Thr Gly Pro Gly Gly Gln Leu Pro
1895                1900                1905

Ala Lys Ala Gln Ile His Gly Gly Ile Leu Arg Leu Pro Ala Val
1910                1915                1920

Glu Pro Thr Asp Gln Ala Gln Tyr Leu Cys Arg Ala His Ser Ser
1925                1930                1935

Ala Gly Gln Gln Val Ala Arg Ala Val Leu His Val His Gly Gly
1940                1945                1950

Gly Gly Pro Arg Val Gln Val Ser Pro Glu Arg Thr Gln Val His
1955                1960                1965

Ala Gly Arg Thr Val Arg Leu Tyr Cys Arg Ala Ala Gly Val Pro
1970                1975                1980

Ser Ala Thr Ile Thr Trp Arg Lys Glu Gly Gly Ser Leu Pro Pro
1985                1990                1995

Gln Ala Arg Ser Glu Arg Thr Asp Ile Ala Thr Leu Leu Ile Pro
2000                2005                2010

Ala Ile Thr Thr Ala Asp Ala Gly Phe Tyr Leu Cys Val Ala Thr
2015                2020                2025

Ser Pro Ala Gly Thr Ala Gln Ala Arg Ile Gln Val Val Val Leu
2030                2035                2040

Ser Ala Ser Asp Ala Ser Pro Pro Val Lys Ile Glu Ser Ser
2045                2050                2055

Ser Pro Ser Val Thr Glu Gly Gln Thr Leu Asp Leu Asn Cys Val
2060                2065                2070

Val Ala Gly Ser Ala His Ala Gln Val Thr Trp Tyr Arg Arg Gly
2075                2080                2085

Gly Ser Leu Pro Pro His Thr Gln Val His Gly Ser Arg Leu Arg
2090                2095                2100

Leu Pro Gln Val Ser Pro Ala Asp Ser Gly Glu Tyr Val Cys Arg
2105                2110                2115

Val Glu Asn Gly Ser Gly Pro Lys Glu Ala Ser Ile Thr Val Ser
2120                2125                2130

Val Leu His Gly Thr His Ser Gly Pro Ser Tyr Thr Pro Val Pro
2135                2140                2145

Gly Ser Thr Arg Pro Ile Arg Ile Glu Pro Ser Ser Ser His Val
2150                2155                2160

Ala Glu Gly Gln Thr Leu Asp Leu Asn Cys Val Val Pro Gly Gln
2165                2170                2175

Ala His Ala Gln Val Thr Trp His Lys Arg Gly Gly Ser Leu Pro
2180                2185                2190

Ala Arg His Gln Thr His Gly Ser Leu Leu Arg Leu His Gln Val
2195                2200                2205

Thr Pro Ala Asp Ser Gly Glu Tyr Val Cys His Val Val Gly Thr
2210                2215                2220

Ser Gly Pro Leu Glu Ala Ser Val Leu Val Thr Ile Glu Ala Ser
2225                2230                2235

Val Ile Pro Gly Pro Ile Pro Pro Val Arg Ile Glu Ser Ser Ser
```

```
                2240                2245                2250
Ser  Thr  Val  Ala  Glu  Gly  Gln  Thr  Leu  Asp  Leu  Ser  Cys  Val  Val
     2255                2260                2265

Ala  Gly  Gln  Ala  His  Ala  Gln  Val  Thr  Trp  Tyr  Lys  Arg  Gly  Gly
     2270                2275                2280

Ser  Leu  Pro  Ala  Arg  His  Gln  Val  Arg  Gly  Ser  Arg  Leu  Tyr  Ile
     2285                2290                2295

Phe  Gln  Ala  Ser  Pro  Ala  Asp  Ala  Gly  Gln  Tyr  Val  Cys  Arg  Ala
     2300                2305                2310

Ser  Asn  Gly  Met  Glu  Ala  Ser  Ile  Thr  Val  Thr  Val  Thr  Gly  Thr
     2315                2320                2325

Gln  Gly  Ala  Asn  Leu  Ala  Tyr  Pro  Ala  Gly  Ser  Thr  Gln  Pro  Ile
     2330                2335                2340

Arg  Ile  Glu  Pro  Ser  Ser  Ser  Gln  Val  Ala  Glu  Gly  Gln  Thr  Leu
     2345                2350                2355

Asp  Leu  Asn  Cys  Val  Val  Pro  Gly  Gln  Ser  His  Ala  Gln  Val  Thr
     2360                2365                2370

Trp  His  Lys  Arg  Gly  Gly  Ser  Leu  Pro  Val  Arg  His  Gln  Thr  His
     2375                2380                2385

Gly  Ser  Leu  Leu  Arg  Leu  Tyr  Gln  Ala  Ser  Pro  Ala  Asp  Ser  Gly
     2390                2395                2400

Glu  Tyr  Val  Cys  Arg  Val  Leu  Gly  Ser  Ser  Val  Pro  Leu  Glu  Ala
     2405                2410                2415

Ser  Val  Leu  Val  Thr  Ile  Glu  Pro  Ala  Gly  Ser  Val  Pro  Ala  Leu
     2420                2425                2430

Gly  Val  Thr  Pro  Thr  Val  Arg  Ile  Glu  Ser  Ser  Ser  Ser  Gln  Val
     2435                2440                2445

Ala  Glu  Gly  Gln  Thr  Leu  Asp  Leu  Asn  Cys  Leu  Val  Ala  Gly  Gln
     2450                2455                2460

Ala  His  Ala  Gln  Val  Thr  Trp  His  Lys  Arg  Gly  Gly  Ser  Leu  Pro
     2465                2470                2475

Ala  Arg  His  Gln  Val  His  Gly  Ser  Arg  Leu  Arg  Leu  Leu  Gln  Val
     2480                2485                2490

Thr  Pro  Ala  Asp  Ser  Gly  Glu  Tyr  Val  Cys  Arg  Val  Val  Gly  Ser
     2495                2500                2505

Ser  Gly  Thr  Gln  Glu  Ala  Ser  Val  Leu  Val  Thr  Ile  Gln  Gln  Arg
     2510                2515                2520

Leu  Ser  Gly  Ser  His  Ser  Gln  Gly  Val  Ala  Tyr  Pro  Val  Arg  Ile
     2525                2530                2535

Glu  Ser  Ser  Ser  Ala  Ser  Leu  Ala  Asn  Gly  His  Thr  Leu  Asp  Leu
     2540                2545                2550

Asn  Cys  Leu  Val  Ala  Ser  Gln  Ala  Pro  His  Thr  Ile  Thr  Trp  Tyr
     2555                2560                2565

Lys  Arg  Gly  Gly  Ser  Leu  Pro  Ser  Arg  His  Gln  Ile  Val  Gly  Ser
     2570                2575                2580

Arg  Leu  Arg  Ile  Pro  Gln  Val  Thr  Pro  Ala  Asp  Ser  Gly  Glu  Tyr
     2585                2590                2595

Val  Cys  His  Val  Ser  Asn  Gly  Ala  Gly  Ser  Arg  Glu  Thr  Ser  Leu
     2600                2605                2610

Ile  Val  Thr  Ile  Gln  Gly  Ser  Gly  Ser  Ser  His  Val  Pro  Ser  Val
     2615                2620                2625

Ser  Pro  Pro  Ile  Arg  Ile  Glu  Ser  Ser  Ser  Pro  Thr  Val  Val  Glu
     2630                2635                2640
```

```
Gly Gln Thr Leu Asp Leu Asn Cys Val Val Ala Arg Gln Pro Gln
2645                2650                2655

Ala Ile Ile Thr Trp Tyr Lys Arg Gly Gly Ser Leu Pro Ser Arg
2660                2665                2670

His Gln Thr His Gly Ser His Leu Arg Leu His Gln Met Ser Val
2675                2680                2685

Ala Asp Ser Gly Glu Tyr Val Cys Arg Ala Asn Asn Asn Ile Asp
2690                2695                2700

Ala Leu Glu Ala Ser Ile Val Ile Ser Val Ser Pro Ser Ala Gly
2705                2710                2715

Ser Pro Ser Ala Pro Gly Ser Ser Met Pro Ile Arg Ile Glu Ser
2720                2725                2730

Ser Ser Ser His Val Ala Glu Gly Glu Thr Leu Asp Leu Asn Cys
2735                2740                2745

Val Val Pro Gly Gln Ala His Ala Gln Val Thr Trp His Lys Arg
2750                2755                2760

Gly Gly Ser Leu Pro Ser His His Gln Thr Arg Gly Ser Arg Leu
2765                2770                2775

Arg Leu His His Val Ser Pro Ala Asp Ser Gly Glu Tyr Val Cys
2780                2785                2790

Arg Val Met Gly Ser Ser Gly Pro Leu Glu Ala Ser Val Leu Val
2795                2800                2805

Thr Ile Glu Ala Ser Gly Ser Ser Ala Val His Val Pro Ala Pro
2810                2815                2820

Gly Gly Ala Pro Pro Ile Arg Ile Glu Pro Ser Ser Ser Arg Val
2825                2830                2835

Ala Glu Gly Gln Thr Leu Asp Leu Lys Cys Val Val Pro Gly Gln
2840                2845                2850

Ala His Ala Gln Val Thr Trp His Lys Arg Gly Gly Asn Leu Pro
2855                2860                2865

Ala Arg His Gln Val His Gly Pro Leu Leu Arg Leu Asn Gln Val
2870                2875                2880

Ser Pro Ala Asp Ser Gly Glu Tyr Ser Cys Gln Val Thr Gly Ser
2885                2890                2895

Ser Gly Thr Leu Glu Ala Ser Val Leu Val Thr Ile Glu Pro Ser
2900                2905                2910

Ser Pro Gly Pro Ile Pro Ala Pro Gly Leu Ala Gln Pro Ile Tyr
2915                2920                2925

Ile Glu Ala Ser Ser Ser His Val Thr Glu Gly Gln Thr Leu Asp
2930                2935                2940

Leu Asn Cys Val Val Pro Gly Gln Ala His Ala Gln Val Thr Trp
2945                2950                2955

Tyr Lys Arg Gly Gly Ser Leu Pro Ala Arg His Gln Thr His Gly
2960                2965                2970

Ser Gln Leu Arg Leu His Leu Val Ser Pro Ala Asp Ser Gly Glu
2975                2980                2985

Tyr Val Cys Arg Ala Ala Ser Gly Pro Gly Pro Glu Gln Glu Ala
2990                2995                3000

Ser Phe Thr Val Thr Val Pro Pro Ser Glu Gly Ser Ser Tyr Arg
3005                3010                3015

Leu Arg Ser Pro Val Ile Ser Ile Asp Pro Pro Ser Ser Thr Val
3020                3025                3030
```

-continued

```
Gln Gln Gly Gln Asp Ala Ser Phe Lys Cys Leu Ile His Asp Gly
    3035                3040                3045

Ala Ala Pro Ile Ser Leu Glu Trp Lys Thr Arg Asn Gln Glu Leu
    3050                3055                3060

Glu Asp Asn Val His Ile Ser Pro Asn Gly Ser Ile Ile Thr Ile
    3065                3070                3075

Val Gly Thr Arg Pro Ser Asn His Gly Thr Tyr Arg Cys Val Ala
    3080                3085                3090

Ser Asn Ala Tyr Gly Val Ala Gln Ser Val Val Asn Leu Ser Val
    3095                3100                3105

His Gly Pro Pro Thr Val Ser Val Leu Pro Glu Gly Pro Val Trp
    3110                3115                3120

Val Lys Val Gly Lys Ala Val Thr Leu Glu Cys Val Ser Ala Gly
    3125                3130                3135

Glu Pro Arg Ser Ser Ala Arg Trp Thr Arg Ile Ser Ser Thr Pro
    3140                3145                3150

Ala Lys Leu Glu Gln Arg Thr Tyr Gly Leu Met Asp Ser His Ala
    3155                3160                3165

Val Leu Gln Ile Ser Ser Ala Lys Pro Ser Asp Ala Gly Thr Tyr
    3170                3175                3180

Val Cys Leu Ala Gln Asn Ala Leu Gly Thr Ala Gln Lys Gln Val
    3185                3190                3195

Glu Val Ile Val Asp Thr Gly Ala Met Ala Pro Gly Ala Pro Gln
    3200                3205                3210

Val Gln Ala Glu Glu Ala Glu Leu Thr Val Glu Ala Gly His Thr
    3215                3220                3225

Ala Thr Leu Arg Cys Ser Ala Thr Gly Ser Pro Ala Pro Thr Ile
    3230                3235                3240

His Trp Ser Lys Leu Arg Ser Pro Leu Pro Trp Gln His Arg Leu
    3245                3250                3255

Glu Gly Asp Thr Leu Ile Ile Pro Arg Val Ala Gln Gln Asp Ser
    3260                3265                3270

Gly Gln Tyr Ile Cys Asn Ala Thr Ser Pro Ala Gly His Ala Glu
    3275                3280                3285

Ala Thr Ile Ile Leu His Val Glu Ser Pro Pro Tyr Ala Thr Thr
    3290                3295                3300

Val Pro Glu His Ala Ser Val Gln Ala Gly Glu Thr Val Gln Leu
    3305                3310                3315

Gln Cys Leu Ala His Gly Thr Pro Pro Leu Thr Phe Gln Trp Ser
    3320                3325                3330

Arg Val Gly Ser Ser Leu Pro Gly Arg Ala Thr Ala Arg Asn Glu
    3335                3340                3345

Leu Leu His Phe Glu Arg Ala Ala Pro Glu Asp Ser Gly Arg Tyr
    3350                3355                3360

Arg Cys Arg Val Thr Asn Lys Val Gly Ser Ala Glu Ala Phe Ala
    3365                3370                3375

Gln Leu Leu Val Gln Gly Pro Pro Gly Ser Leu Pro Ala Thr Ser
    3380                3385                3390

Ile Pro Ala Gly Ser Thr Pro Thr Val Gln Val Thr Pro Gln Leu
    3395                3400                3405

Glu Thr Lys Ser Ile Gly Ala Ser Val Glu Phe His Cys Ala Val
    3410                3415                3420

Pro Ser Asp Arg Gly Thr Gln Leu Arg Trp Phe Lys Glu Gly Gly
```

```
                    3425                3430                3435
Gln Leu Pro Pro Gly His Ser Val Gln Asp Gly Val Leu Arg Ile
    3440                3445                3450
Gln Asn Leu Asp Gln Ser Cys Gln Gly Thr Tyr Ile Cys Gln Ala
    3455                3460                3465
His Gly Pro Trp Gly Lys Ala Gln Ala Ser Ala Gln Leu Val Ile
    3470                3475                3480
Gln Ala Leu Pro Ser Val Leu Ile Asn Ile Arg Thr Ser Val Gln
    3485                3490                3495
Thr Val Val Val Gly His Ala Val Glu Phe Glu Cys Leu Ala Leu
    3500                3505                3510
Gly Asp Pro Lys Pro Gln Val Thr Trp Ser Lys Val Gly Gly His
    3515                3520                3525
Leu Arg Pro Gly Ile Val Gln Ser Gly Gly Val Val Arg Ile Ala
    3530                3535                3540
His Val Glu Leu Ala Asp Ala Gly Gln Tyr Arg Cys Thr Ala Thr
    3545                3550                3555
Asn Ala Ala Gly Thr Thr Gln Ser His Val Leu Leu Leu Val Gln
    3560                3565                3570
Ala Leu Pro Gln Ile Ser Met Pro Gln Glu Val Arg Val Pro Ala
    3575                3580                3585
Gly Ser Ala Ala Val Phe Pro Cys Ile Ala Ser Gly Tyr Pro Thr
    3590                3595                3600
Pro Asp Ile Ser Trp Ser Lys Leu Asp Gly Ser Leu Pro Pro Asp
    3605                3610                3615
Ser Arg Leu Glu Asn Asn Met Leu Met Leu Pro Ser Val Arg Pro
    3620                3625                3630
Gln Asp Ala Gly Thr Tyr Val Cys Thr Ala Thr Asn Arg Gln Gly
    3635                3640                3645
Lys Val Lys Ala Phe Ala His Leu Gln Val Pro Glu Arg Val Val
    3650                3655                3660
Pro Tyr Phe Thr Gln Thr Pro Tyr Ser Phe Leu Pro Leu Pro Thr
    3665                3670                3675
Ile Lys Asp Ala Tyr Arg Lys Phe Glu Ile Lys Ile Thr Phe Arg
    3680                3685                3690
Pro Asp Ser Ala Asp Gly Met Leu Leu Tyr Asn Gly Gln Lys Arg
    3695                3700                3705
Val Pro Gly Ser Pro Thr Asn Leu Ala Asn Arg Gln Pro Asp Phe
    3710                3715                3720
Ile Ser Phe Gly Leu Val Gly Gly Arg Pro Glu Phe Arg Phe Asp
    3725                3730                3735
Ala Gly Ser Gly Met Ala Thr Ile Arg His Pro Thr Pro Leu Ala
    3740                3745                3750
Leu Gly His Phe His Thr Val Thr Leu Leu Arg Ser Leu Thr Gln
    3755                3760                3765
Gly Ser Leu Ile Val Gly Asp Leu Ala Pro Val Asn Gly Thr Ser
    3770                3775                3780
Gln Gly Lys Phe Gln Gly Leu Asp Leu Asn Glu Glu Leu Tyr Leu
    3785                3790                3795
Gly Gly Tyr Pro Asp Tyr Gly Ala Ile Pro Lys Ala Gly Leu Ser
    3800                3805                3810
Ser Gly Phe Ile Gly Cys Val Arg Glu Leu Arg Ile Gln Gly Glu
    3815                3820                3825
```

-continued

Glu Ile Val Phe His Asp Leu Asn Leu Thr Ala His Gly Ile Ser
3830                    3835                3840

His Cys Pro Thr Cys Arg Asp Arg Pro Cys Gln Asn Gly Gly Gln
3845                    3850                3855

Cys His Asp Ser Glu Ser Ser Tyr Val Cys Val Cys Pro Ala
3860                    3865                3870

Gly Phe Thr Gly Ser Arg Cys Glu His Ser Gln Ala Leu His Cys
3875                    3880                3885

His Pro Glu Ala Cys Gly Pro Asp Ala Thr Cys Val Asn Arg Pro
3890                    3895                3900

Asp Gly Arg Gly Tyr Thr Cys Arg Cys His Leu Gly Arg Ser Gly
3905                    3910                3915

Leu Arg Cys Glu Glu Gly Val Thr Val Thr Thr Pro Ser Leu Ser
3920                    3925                3930

Gly Ala Gly Ser Tyr Leu Ala Leu Pro Ala Leu Thr Asn Thr His
3935                    3940                3945

His Glu Leu Arg Leu Asp Val Glu Phe Lys Pro Leu Ala Pro Asp
3950                    3955                3960

Gly Val Leu Leu Phe Ser Gly Gly Lys Ser Gly Pro Val Glu Asp
3965                    3970                3975

Phe Val Ser Leu Ala Met Val Gly Gly His Leu Glu Phe Arg Tyr
3980                    3985                3990

Glu Leu Gly Ser Gly Leu Ala Val Leu Arg Ser Ala Glu Pro Leu
3995                    4000                4005

Ala Leu Gly Arg Trp His Arg Val Ser Ala Glu Arg Leu Asn Lys
4010                    4015                4020

Asp Gly Ser Leu Arg Val Asn Gly Gly Arg Pro Val Leu Arg Ser
4025                    4030                4035

Ser Pro Gly Lys Ser Gln Gly Leu Asn Leu His Thr Leu Leu Tyr
4040                    4045                4050

Leu Gly Gly Val Glu Pro Ser Val Pro Leu Ser Pro Ala Thr Asn
4055                    4060                4065

Met Ser Ala His Phe Arg Gly Cys Val Gly Glu Val Ser Val Asn
4070                    4075                4080

Gly Lys Arg Leu Asp Leu Thr Tyr Ser Phe Leu Gly Ser Gln Gly
4085                    4090                4095

Ile Gly Gln Cys Tyr Asp Ser Ser Pro Cys Glu Arg Gln Pro Cys
4100                    4105                4110

Gln His Gly Ala Thr Cys Met Pro Ala Gly Glu Tyr Glu Phe Gln
4115                    4120                4125

Cys Leu Cys Arg Asp Gly Phe Lys Gly Asp Leu Cys Glu His Glu
4130                    4135                4140

Glu Asn Pro Cys Gln Leu Arg Glu Pro Cys Leu His Gly Gly Thr
4145                    4150                4155

Cys Gln Gly Thr Arg Cys Leu Cys Leu Pro Gly Phe Ser Gly Pro
4160                    4165                4170

Arg Cys Gln Gln Gly Ser Gly His Gly Ile Ala Glu Ser Asp Trp
4175                    4180                4185

His Leu Glu Gly Ser Gly Gly Asn Asp Ala Pro Gly Gln Tyr Gly
4190                    4195                4200

Ala Tyr Phe His Asp Asp Gly Phe Leu Ala Phe Pro Gly His Val
4205                    4210                4215

-continued

```
Phe Ser Arg Ser Leu Pro Glu Val Pro Glu Thr Ile Glu Leu Glu
4220                    4225                4230
Val Arg Thr Ser Thr Ala Ser Gly Leu Leu Leu Trp Gln Gly Val
4235                    4240                4245
Glu Val Gly Glu Ala Gly Gln Gly Lys Asp Phe Ile Ser Leu Gly
4250                    4255                4260
Leu Gln Asp Gly His Leu Val Phe Arg Tyr Gln Leu Gly Ser Gly
4265                    4270                4275
Glu Ala Arg Leu Val Ser Glu Asp Pro Ile Asn Asp Gly Glu Trp
4280                    4285                4290
His Arg Val Thr Ala Leu Arg Glu Gly Arg Arg Gly Ser Ile Gln
4295                    4300                4305
Val Asp Gly Glu Glu Leu Val Ser Gly Arg Ser Pro Gly Pro Asn
4310                    4315                4320
Val Ala Val Asn Ala Lys Gly Ser Val Tyr Ile Gly Gly Ala Pro
4325                    4330                4335
Asp Val Ala Thr Leu Thr Gly Gly Arg Phe Ser Ser Gly Ile Thr
4340                    4345                4350
Gly Cys Val Lys Asn Leu Val Leu His Ser Ala Arg Pro Gly Ala
4355                    4360                4365
Pro Pro Pro Gln Pro Leu Asp Leu Gln His Arg Ala Gln Ala Gly
4370                    4375                4380
Ala Asn Thr Arg Pro Cys Pro Ser
4385                    4390
```